(12) United States Patent
Ehnes et al.

(10) Patent No.: US 11,559,386 B2
(45) Date of Patent: Jan. 24, 2023

(54) ENDOVASCULAR GRAFT SYSTEMS AND METHODS FOR DEPLOYMENT IN MAIN AND BRANCH ARTERIES

(71) Applicant: Endologix LLC, Irvine, CA (US)

(72) Inventors: Dale Ehnes, Forestville, CA (US); Arif Iftekhar, Irvine, CA (US); Craig Welk, Irvine, CA (US); Kevin Knoll, Irvine, CA (US)

(73) Assignee: Endologix LLC, Irvine, CA (US)

( * ) Notice: Subject to any disclaimer, the term of this patent is extended or adjusted under 35 U.S.C. 154(b) by 2 days.

(21) Appl. No.: 16/629,032

(22) PCT Filed: Jul. 6, 2018

(86) PCT No.: PCT/US2018/041152
§ 371 (c)(1),
(2) Date: Jan. 6, 2020

(87) PCT Pub. No.: WO2019/010458
PCT Pub. Date: Jan. 10, 2019

(65) Prior Publication Data
US 2020/0170778 A1 Jun. 4, 2020

Related U.S. Application Data

(60) Provisional application No. 62/529,669, filed on Jul. 7, 2017.

(51) Int. Cl.
*A61F 2/07* (2013.01)
*A61F 2/88* (2006.01)
(Continued)

(52) U.S. Cl.
CPC .............. *A61F 2/07* (2013.01); *A61F 2/848* (2013.01); *A61F 2/88* (2013.01); *A61F 2/89* (2013.01);
(Continued)

(58) Field of Classification Search
None
See application file for complete search history.

(56) References Cited

U.S. PATENT DOCUMENTS 6,558,414 B2 5/2003 Layne
6,592,614 B2 7/2003 Lenker et al.
(Continued)

FOREIGN PATENT DOCUMENTS

CN 201303993 9/2009
JP H10-328216 A 12/1998
(Continued)

OTHER PUBLICATIONS

International Preliminary Report on Patentability dated Jan. 16, 2020, from application No. PCT/US2018/041152.
(Continued)

*Primary Examiner* — Leslie Lopez
(74) *Attorney, Agent, or Firm* — Foley & Lardner LLP

(57) ABSTRACT

Endovascular systems for deployment at branched arteries include a main tubular graft body deployable within a main artery including a proximal end and an opposed distal end. The proximal and distal ends have a tubular graft wall therein between. A plurality of inflatable channels are disposed along the main tubular graft body, and at least one stent segment is disposed along the tubular graft wall of the main tubular graft body. The plurality of inflatable channels are configured to be inflatable with an inflation medium. The at least one stent segment is disposed between two or more adjacent inflatable channels of the plurality of inflatable channels.

8 Claims, 43 Drawing Sheets

(51) Int. Cl.
  *A61F 2/89* (2013.01)
  *A61F 2/06* (2013.01)
  *A61F 2/848* (2013.01)
  *A61F 2/90* (2013.01)
  *A61F 2/82* (2013.01)

(52) U.S. Cl.
  CPC .......... *A61F 2/90* (2013.01); *A61F 2002/061* (2013.01); *A61F 2002/825* (2013.01); *A61F 2250/0003* (2013.01); *A61F 2250/0039* (2013.01); *A61F 2250/0063* (2013.01); *A61F 2250/0098* (2013.01)

(56) References Cited

U.S. PATENT DOCUMENTS

| | | |
|---|---|---|
| 6,860,900 B2 | 3/2005 | Clerc et al. |
| 6,866,805 B2 | 3/2005 | Hong et al. |
| 6,911,040 B2 | 6/2005 | Johnson et al. |
| 7,314,484 B2 | 1/2008 | Deem et al. |
| 7,326,237 B2 | 2/2008 | Depalma et al. |
| 7,438,721 B2 | 10/2008 | Doig et al. |
| 7,666,220 B2 | 2/2010 | Evans et al. |
| 7,678,217 B2 | 3/2010 | Chobotov et al. |
| 7,682,380 B2 | 3/2010 | Thornton et al. |
| 7,803,178 B2 | 9/2010 | Whirley et al. |
| 7,806,922 B2 | 10/2010 | Henderson et al. |
| 8,043,357 B2 | 10/2011 | Hartley |
| 8,048,145 B2 | 11/2011 | Evans et al. |
| 8,092,511 B2 | 1/2012 | Chuter |
| 8,167,926 B2 | 5/2012 | Hartley et al. |
| 8,211,158 B2 | 7/2012 | Wolf |
| 8,267,989 B2 | 9/2012 | Whirley et al. |
| 8,292,949 B2 | 10/2012 | Berra et al. |
| 8,333,800 B2 | 12/2012 | Bruszewski et al. |
| 8,663,310 B2 | 3/2014 | Greenberg et al. |
| 8,672,995 B2 | 3/2014 | Blank et al. |
| 8,945,203 B2 | 2/2015 | Shalev et al. |
| 8,998,972 B2 | 4/2015 | Smirthwaite et al. |
| 9,005,268 B2 | 4/2015 | Hartley et al. |
| 9,066,793 B2 | 6/2015 | Hung et al. |
| 9,095,421 B2 | 8/2015 | Peterson |
| 9,101,456 B2 | 8/2015 | Hartley et al. |
| 9,144,486 B2 | 9/2015 | Vinluan |
| 9,211,183 B2 | 12/2015 | Ivancev et al. |
| 9,402,751 B2 | 8/2016 | Zukowski |
| 2001/0047199 A1 | 11/2001 | Wijay |
| 2004/0243221 A1 | 12/2004 | Fawzi et al. |
| 2005/0010277 A1 | 1/2005 | Chuter |
| 2005/0228484 A1 | 10/2005 | Stephens et al. |
| 2006/0247760 A1 | 11/2006 | Ganesan et al. |
| 2008/0234809 A1 | 9/2008 | Greenan |
| 2009/0048663 A1 | 2/2009 | Greenberg |
| 2010/0161025 A1 | 6/2010 | Kuppurathanam et al. |
| 2010/0280588 A1 | 11/2010 | Schreck |
| 2011/0130819 A1 | 6/2011 | Cragg et al. |
| 2012/0041544 A1 | 2/2012 | Wolf |
| 2012/0191174 A1 | 7/2012 | Vinluan et al. |
| 2012/0296414 A1 | 11/2012 | Hartley |
| 2013/0103135 A1* | 4/2013 | Vinluan .................... A61F 2/07 623/1.13 |
| 2013/0184806 A1 | 7/2013 | Arbefeuille et al. |
| 2013/0253632 A1 | 9/2013 | Schreck |
| 2013/0261734 A1 | 10/2013 | Young et al. |
| 2013/0296998 A1 | 11/2013 | Leotta et al. |
| 2014/0039597 A9 | 2/2014 | Arbefeuille et al. |
| 2014/0100650 A1 | 4/2014 | Chobotov |
| 2014/0296964 A1 | 10/2014 | Huser et al. |
| 2014/0316513 A1 | 10/2014 | Tang |
| 2014/0336749 A1 | 11/2014 | Bogenschuetz et al. |
| 2015/0088244 A1 | 3/2015 | Chobotov |
| 2015/0157448 A1 | 6/2015 | Kelly |
| 2016/0000589 A1 | 1/2016 | Xue |
| 2016/0022409 A1 | 1/2016 | Aharon et al. |
| 2016/0030209 A1 | 2/2016 | Shalev et al. |
| 2016/0067067 A1 | 3/2016 | Roselli |
| 2017/0007263 A1 | 1/2017 | Schreck et al. |

FOREIGN PATENT DOCUMENTS

| | | |
|---|---|---|
| WO | WO-03/053495 A2 | 7/2003 |
| WO | WO-2005/112823 | 12/2005 |
| WO | WO-2009/020653 | 2/2009 |
| WO | WO-2012/095504 | 7/2012 |
| WO | WO-2015/183489 A1 | 12/2015 |

OTHER PUBLICATIONS

Carrafiello et al., "Treatment of abdominal aortic aneurysm with a new type of polymer-filled low profile device," International Journal of Surgery, vol. 11, Supp. 1, Dec. 2013, pp. S24-S29.

Donas et al., "Use of covered chimney stents for pararenal aortic pathologies is safe and feasible with excellent patency and low incidence of endoleaks," Journal of Vascular Surgery, vol. 55, No. 3, Mar. 2012, pp. 659-665.

Minion, D.J., "Molded Parallel Endografts for Branch Vessel Preservation during Endovascular Aneurysm Repair in Challenging Anatomy," The International Journal of Angiology, vol. 21, No. 2, May 28, 2012, pp. 81-83.

International Search Report and Written Opinion dated Sep. 11, 2018, from application No. PCT/US2018/041152.

Extended European Search Report dated Feb. 24, 2021, from application No. 18829157.9.

Chinese Office Action dated Aug. 25, 2021, from application No. 201880057046.3.

Chinese Office Action dated Jan. 24, 2022, from application No. 201880057046.3.

Japanese Office Action dated Aug. 3, 2022, from application No. 2020-500065.

* cited by examiner

Fig. 7C
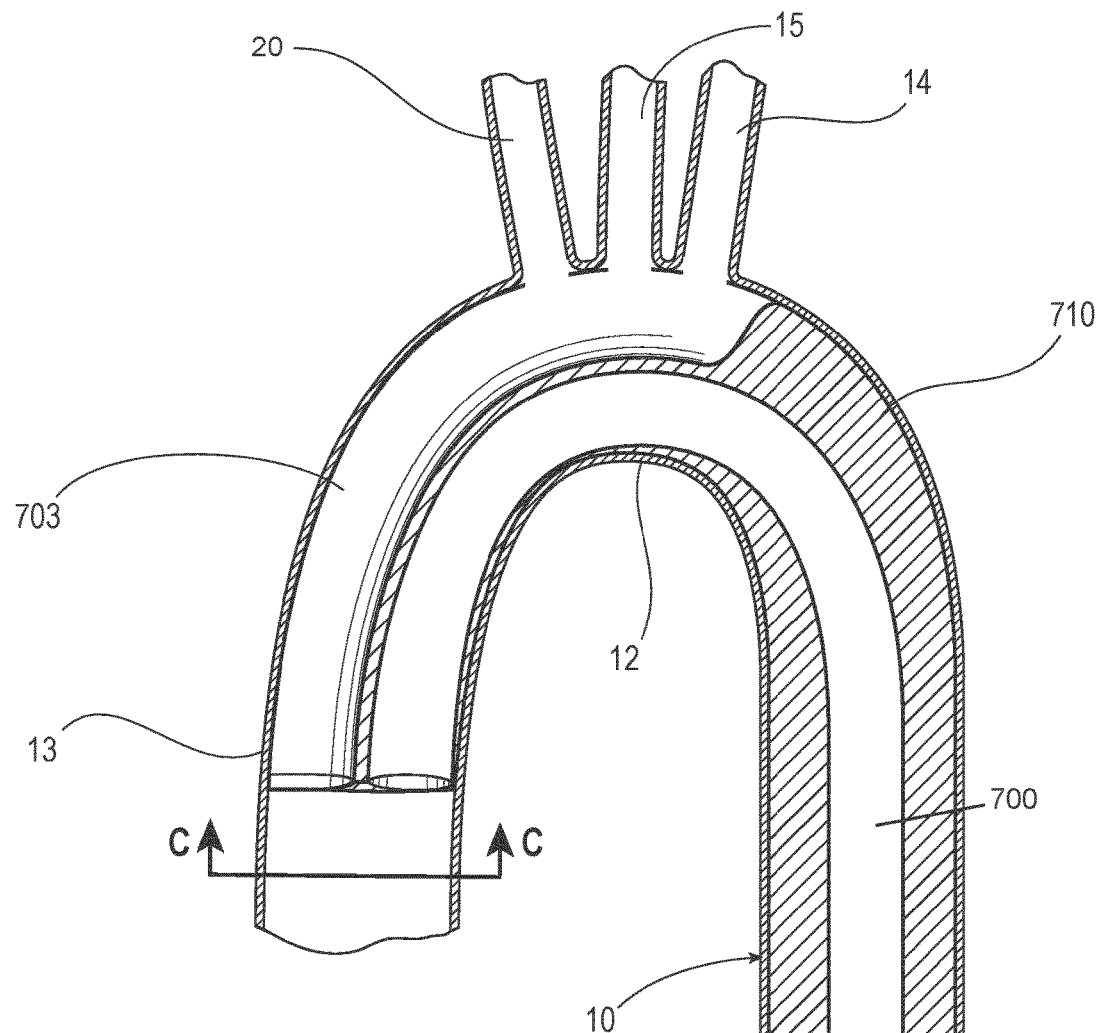
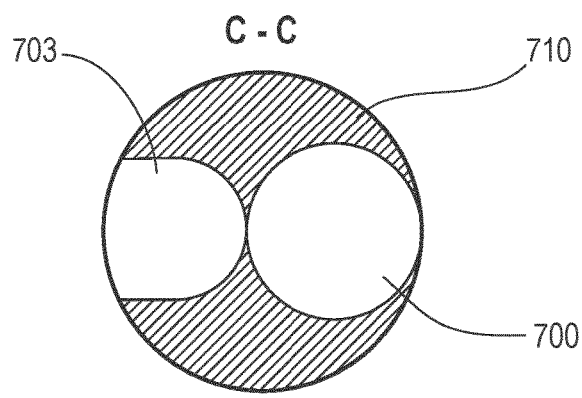
Fig. 7D

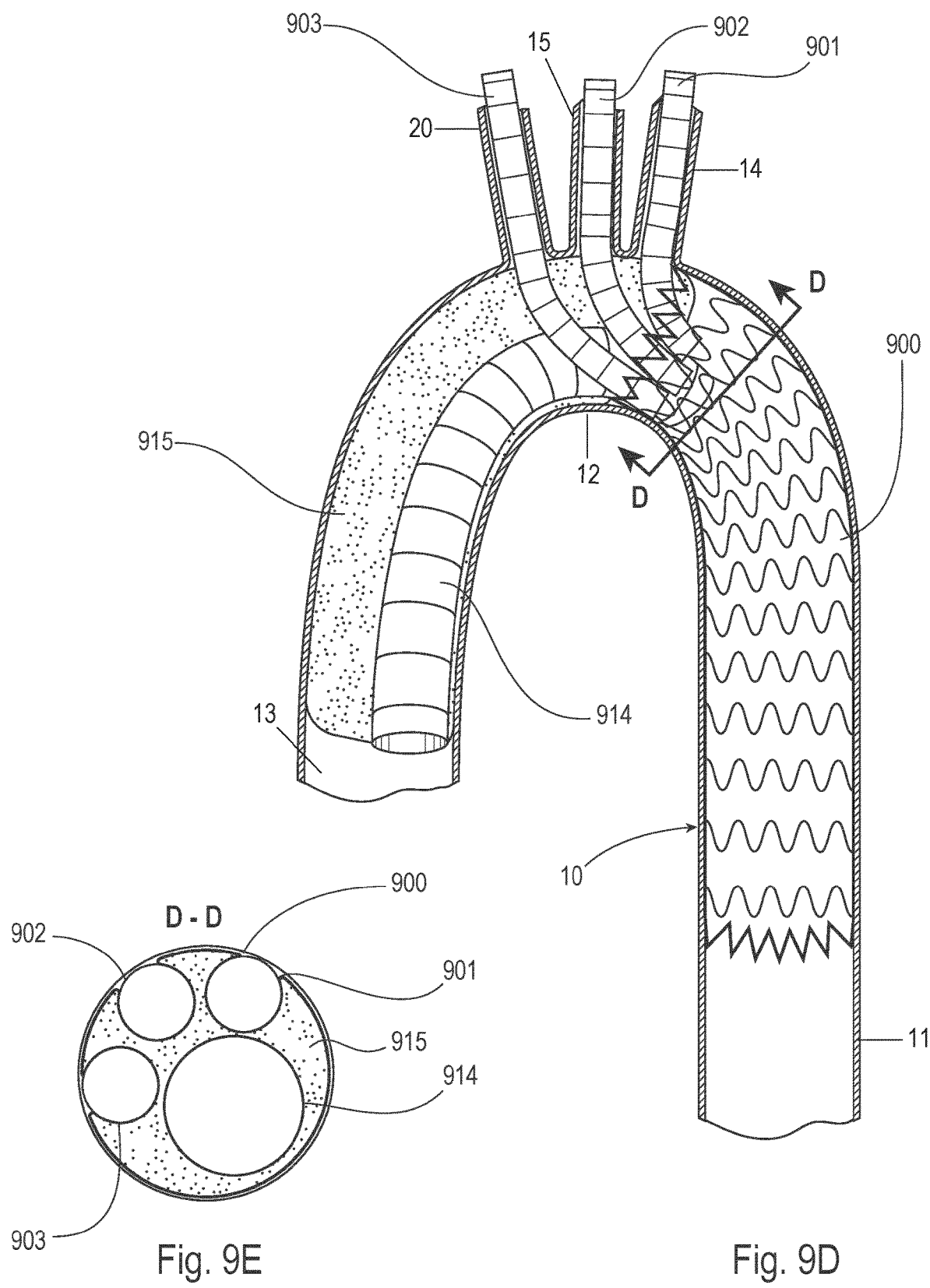

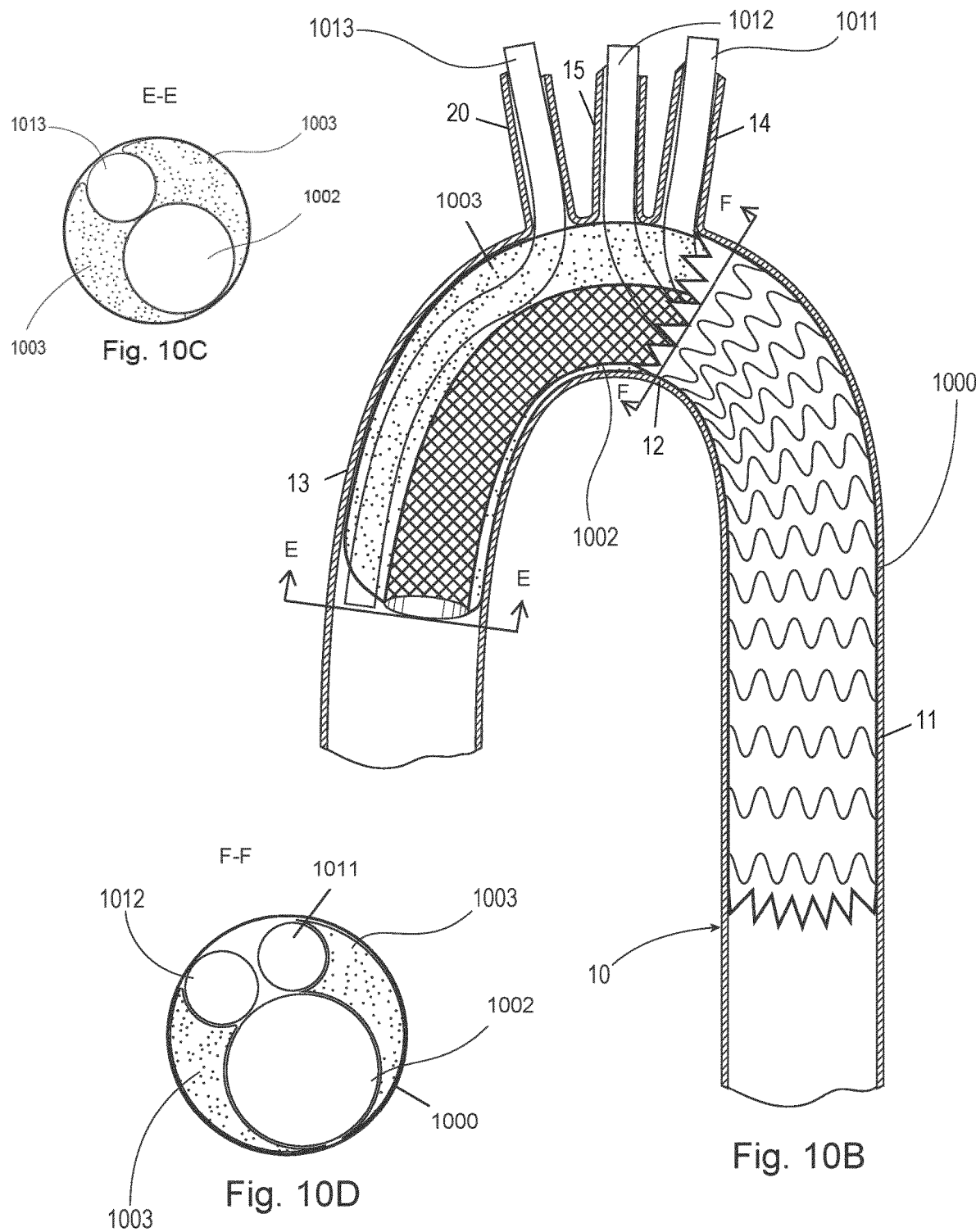

ENDOVASCULAR GRAFT SYSTEMS AND METHODS FOR DEPLOYMENT IN MAIN AND BRANCH ARTERIES

CROSS-REFERENCE TO RELATED APPLICATIONS

This application is a national stage application under 35 U.S.C. § 371 of International Application No. PCT/US018/041152, file on Jul. 6, 2018, which claims priority to U.S. Provisional Patent Application No. 62/529,669, filed on Jul. 7, 2017, which ii the contents of each of which are hereby incorporated by reference in its entirety their entireties.

FIELD

Arrangements disclosed herein relate generally to the field of endovascular graft systems. In particular, various arrangements relate to endovascular graft systems for placement in a thoracic endoluminal space and allowing for the perfusion of blood to the greater arch vessels. Various arrangements also relate to endovascular graft systems with kink resistance features.

BACKGROUND

The present disclosure relates to systems and methods for treating vasculature disorders, such as aneurysms. An aneurysm is a medical condition characterized by an expansion and corresponding weakening of the wall of an artery of a person. Aneurysms can develop at different sites within an artery. For example, thoracic aortic aneurysms or abdominal aortic aneurysms may manifest within a person's body. This medical condition is serious and potentially life threatening to the person, thereby requiring medical intervention to treat the condition. Existing systems and methods for treating such conditions include invasive surgical procedures with graft replacement of the affected vessel or body lumen or reinforcement of the vessel with a graft.

Surgical procedures to treat aneurysms are associated with relatively high morbidity and mortality rates due to risk factors inherent to surgical repair of an artery or artery wall. Long and painful recoveries are often required, resulting in extensive medical costs. Because of the inherent risks and complexities of surgical repair of an aortic aneurysm, endovascular repair has become a widely used alternative therapy.

SUMMARY OF THE DISCLOSURE

Various arrangements disclosed herein are directed to systems and methods for treating diseased bodily lumens involving branched lumen deployment sites. Various methods include using the systems disclosed herein to maintain blood flow through a main artery and from the main artery to one or more branch arteries.

In various arrangements, an endovascular graft or section thereof includes sealing rings with stent segments interspersed in-between the sealing rings. In various arrangements, an endovascular graft system for deployment at branched arteries includes a main tubular graft body deployable within a main artery comprising a proximal end and an opposed distal end, where the proximal and distal ends define a tubular graft wall therein between. In various arrangements, the endovascular graft system includes a plurality of inflatable channels disposed along the main tubular graft body, and at least one stent segment that is disposed along the tubular graft wall of the main tubular graft body. In some arrangements, the plurality of inflatable channels are configured to be inflatable with an inflation medium, and the at least one stent segment is disposed between two or more adjacent inflatable channels.

In some arrangements, the at least one stent segment is at least one ring segment. In some arrangements, the at least one stent segment has a C-shape. In some arrangements, the at least one stent segment is at least one nested ring segment. In some arrangements, the at least one stent segment is a continuous wire wound stent. In some arrangements, the at least one stent segment is a helical continuous wire wound stent. In some arrangements, the at least one stent segment has a circular cross sectional shape. In some arrangements, the at least one stent segment has a partially circumferential cross sectional shape. In some arrangements, the at least one stent segment has a completely circumferential cross sectional shape.

In various arrangements, the main tubular graft body has at least one fenestration disposed between two or more adjacent inflatable channels of the plurality of inflatable channels. In some arrangements, the at least one fenestration is configured to be in fluid contact with at least one branch artery branched from a main artery. In some arrangements, the at least one fenestration is covered by a mesh. In some arrangements, the at least one fenestration extends an entirety of a distance between the two or more adjacent inflatable channels. In some arrangements, the at least one fenestration is an opening having a semi-circular cross-sectional shape. In some arrangements, the at least one fenestration is an opening having a half-circular cross-sectional shape. In some arrangements, the at least one fenestration is supported by the two or more adjacent inflatable channels and by one or more adjacent stent segments.

In various arrangements, the endovascular system includes an anchoring member attached to the proximal open end. In some arrangements, at least a portion of the anchoring member is disposed beyond the proximal open end of the main tubular graft body. In some arrangements, the endovascular system includes an anchoring member attached to the distal open end. Also, in some arrangements, at least a portion of the anchoring member is disposed beyond the distal open end of the main tubular graft body.

In various arrangements, an endovascular system for deployment at branched arteries to enable perfusion of blood to the branched arteries includes a first tubular graft body deployable within a main artery comprising a proximal open end and an opposed distal open end. In various arrangements, the proximal and distal ends define a tubular graft wall therein between, and a second tubular graft body is disposed in fluid contact with the first tubular graft body and is deployable in a parallel configuration to the first tubular graft body. In some arrangements, a fillable bag is connected to an outer surface of the first tubular graft body and is configured to seal around at least a portion of the first tubular graft body in a main artery of a person. In various arrangements, the second tubular graft body has at least one fenestration configured to be in apposition to at least one branch artery of a person.

In some arrangements, the first tubular graft body further comprises a plurality of inflatable channels disposed along the first tubular graft body. In some arrangements, the second tubular graft body further comprises a plurality of inflatable channels disposed along the second tubular graft body. In some arrangements, the first tubular graft body comprises a wire wound stent. In some arrangements, the second tubular graft body comprises a wire wound stent.

In some arrangements, the fillable bag is configured to provide a seal in a proximal portion of an arch portion of the main artery. In some arrangements, the fillable bag is configured to provide a seal in a distal portion of an arch portion of the main artery. In some arrangements, the fillable bag comprises a polymer endobag. In some arrangements, the fillable bag comprises polymer rings.

In some arrangements, the endovascular system includes at least one chimney graft having a proximal portion with a proximal open end deployable within a main artery and an opposed distal portion with a distal open end deployable within a branch artery branched from the main artery. In some arrangements, the at least one chimney graft is configured to be in fluid contact with the at least one fenestration of the second tubular graft body. In some arrangements, the at least one chimney graft is configured to be in fluid contact with the first tubular graft body. In some arrangements, the at least one chimney graft is configured to be in fluid contact with the second tubular graft body.

In some arrangements, the endovascular system includes a slidable component configured to minimize gutters in the first tubular graft body and the second tubular graft body. In some arrangements, the endovascular system includes support for the fenestration. In some arrangements, the second tubular graft body comprises polymer half-ring channels configured to provide radial support and flexibility to a fenestration. In some arrangements, the second tubular graft body comprises polymer channels configured to provide axial and radial support for the fenestration. In some arrangements, the fenestration of the second tubular graft body is configured to have an elliptical shape. In some arrangements, the fenestration of the second tubular graft body is configured to receive at least one chimney graft corresponding to at least one branch artery. In some arrangements, radiopaque markers are disposed around the fenestration of the second tubular graft body and are configured to indicate a location and position of the fenestration axially and rotationally with respect to at least one branch artery. In some arrangements, the support is formed of cutouts of laminated graft materials.

In various arrangements, an endovascular system includes a proximal graft body, and a distal graft body connected to the proximal graft body, and is configured to allow fluid contact between the proximal graft body and the distal graft body. In some arrangements, the endovascular system includes a fillable bag configured to seal around at least a portion of the proximal graft body and the distal graft body.

In some arrangements, the endovascular system includes at least one chimney graft configured to extend from an opening of either the proximal graft body or the distal graft body to at least one branch artery. In some arrangements, a first portion of the proximal graft body has a portion having a smaller cross-section than a second portion of the proximal graft body. In some arrangements, the proximal graft body comprises a fenestration disposed on a surface of the proximal graft body. In some arrangements, the proximal graft body and the distal graft body are welded together. In some arrangements, the proximal graft body and the distal graft body are placed together as modules.

In various arrangements, a method for inserting an endovascular system in a main artery of a person includes deploying an endovascular system into a main artery, gaining wire access of at least one branch artery, deploying chimney grafts into each of the at least one branch artery, and positioning an endovascular system such that there is an axial overlap between the endovascular system and the branch grafts.

In some arrangements, gaining wire access of at least one branch artery is performed using at least two wires. In some arrangements, the step of gaining wire access of at least one branch artery is performed using three wires. In some arrangements, the branch stent grafts comprise bare stents.

In some arrangements, an endovascular system for deployment at a main artery and branched arteries that branch off from the main artery to enable perfusion of blood to the branched arteries includes a first tubular graft body configured to be deployed within a first portion of the main artery, a second tubular graft body disposed in fluid contact with the first tubular graft body where the second tubular graft body is configured to be deployed within a second portion of the main artery, and at least one branch tubular graft body in fluid contact with the first tubular graft body. Each of the at least one branch tubular graft body is configured to be deployed within one of the branched arteries.

In some arrangements, the main artery is an aorta, the first portion of the main artery corresponds to a descending aorta portion, the second portion of the main artery corresponds to an ascending aorta portion and an aortic arch portion, and each of the branched arteries is one of a innominate artery, a left common carotid artery, and a left subclavian artery.

In some arrangements, the at least one branch tubular graft body includes a first branch tubular graft body configured to extend from the aortic arch portion to the innominate artery, a second branch tubular graft body configured to extend from the aortic arch portion to the left common carotid artery, and a third branch tubular graft body configured to extend from the aortic arch portion to the left subclavian artery.

In some arrangements, the second tubular graft body and the at least one branch tubular graft body connect to the first tubular graft body at or adjacent to one of the branched arteries.

In some arrangements, the endovascular system further includes a fillable bag connected to the second tubular graft body, the fillable bag being configured to expand to fill a space in the second portion of the main artery except for spaces occupied by the second tubular graft body and the at least one branch tubular graft body.

In some arrangements, the second tubular graft body includes inflatable channels.

In some arrangements, the inflatable channels are polymer rings or fillable bags.

In some arrangements, the endovascular system further includes at least one branch tubular graft body configured to be deployed within one of the branched arteries and the second portion of the main artery.

In some arrangements, the endovascular system further includes an inflatable bag. In some embodiments, the first tubular graft body, the second tubular graft body, and the inflatable bag are welded together. In some embodiments, the first tubular graft body, the second tubular graft body are modules that are attachable to each other.

In some arrangements, the inflatable bag includes at least one slot, and each of the at least one slot is configured to allow one of the at least one branch tubular graft body to pass through to extend to a corresponding one of the branched arteries.

In some arrangements, the inflatable bag is configured to be filled with a polymer to provide a polymer seal around the at least one branch tubular graft body at the at least one slot.

In some arrangements, an inflatable bag is connected to each of the at least one branch tubular graft body.

In some arrangements, the inflatable bag of each of the at least one branch tubular graft body is configured to fill a space in the second portion of the main artery.

In some arrangements, a diameter of the second tubular body decreases over a length of the first tubular body in a direction toward the first tubular body, creating a space configured for the at least one branch tubular graft body to connect to the first tubular body.

In some arrangements, an endovascular system for deployment at a main artery and branched arteries that branch off from the main artery to enable perfusion of blood to the branched arteries includes a tubular graft body that is configured to be deployed within the main artery and that has at least one fenestration, an inflatable bag connected to the tubular graft body and having at least one slot, and at least one branch tubular graft body in fluid contact with the tubular graft body, where each of the at least one branch tubular graft body is configured to be deployed within one of the branched arteries through a corresponding one of the at least one slot.

BRIEF DESCRIPTION OF THE DRAWINGS

FIG. 7C shows an endovascular system in accordance with an arrangement deployed in an aortic arch.

FIG. 7D is a cross-sectional view of a section of FIG. 7C.

FIG. 9D shows an endovascular system in accordance with an arrangement deployed in an aortic arch.

FIG. 9E is a cross-sectional view of a section of FIG. 9D.

FIG. 10B shows an endovascular system in accordance with an arrangement deployed in an aortic arch.

FIG. 10C is a cross-sectional view of the endovascular system of FIG. 10B.

FIG. 10D is another cross-sectional view of the endovascular system of FIG. 10B.

DETAILED DESCRIPTION

Various arrangements disclosed herein are directed generally to systems and methods for treatment of fluid flow vessels of the body of a person. Treatment of blood vessels is specifically indicated for some arrangements. The present disclosure provides various endovascular systems for treatment of blood vessels, including modular graft systems, bifurcated graft assemblies, stent-graft assemblies, and combinations thereof.

With regard to arrangements of graft systems discussed herein and the components thereof, the term "proximal" refers to a location towards or closer to a person's heart, and the term "distal" refers to a location away or farther from a person's heart. With regard to delivery system catheters and components thereof discussed herein, the term "distal" refers to a location that is disposed away or farther from an operator who is using the catheter, and the term "proximal" refers to a location towards or closer to the operator.

An endovascular graft or section thereof in accordance with various arrangements includes sealing rings with stent segments interspersed in-between the sealing rings. In various arrangements, the sealing rings are polymer sealing rings and are configured to hold a blood flow lumen open when filled with polymer. In some arrangements, an interstitial space between adjacent sealing rings includes a graft. In some arrangements, the graft is made of Polytetrafluoroethylene (PTFE) or the like. In various arrangements, the endovascular graft is deployable in angulated anatomies.

In various arrangements, a stent is interspersed in-between polymer sealing rings. In some arrangements, the stent is a continuous helical wire wound stent. In some arrangements, the stent comprises multiple series of individually nested stent rings. In various arrangements, the stent provides support to keep a lumen open while the endovascular graft is curved. In various arrangements, the stent structure is intimately laminated into the graft. In some arrangements, the stent structure is adhered to or bonded to the graft by other means, such as by sutures, glue, or the like. In various arrangements, the stent material is made from Nitinol or other suitable material. In various arrangements, the stent is made of wire or laser cut from tubing and then expanded to a suitable diameter. In some arrangements, stent segments are interspersed in-between polymer sealing rings.

Figure 1:
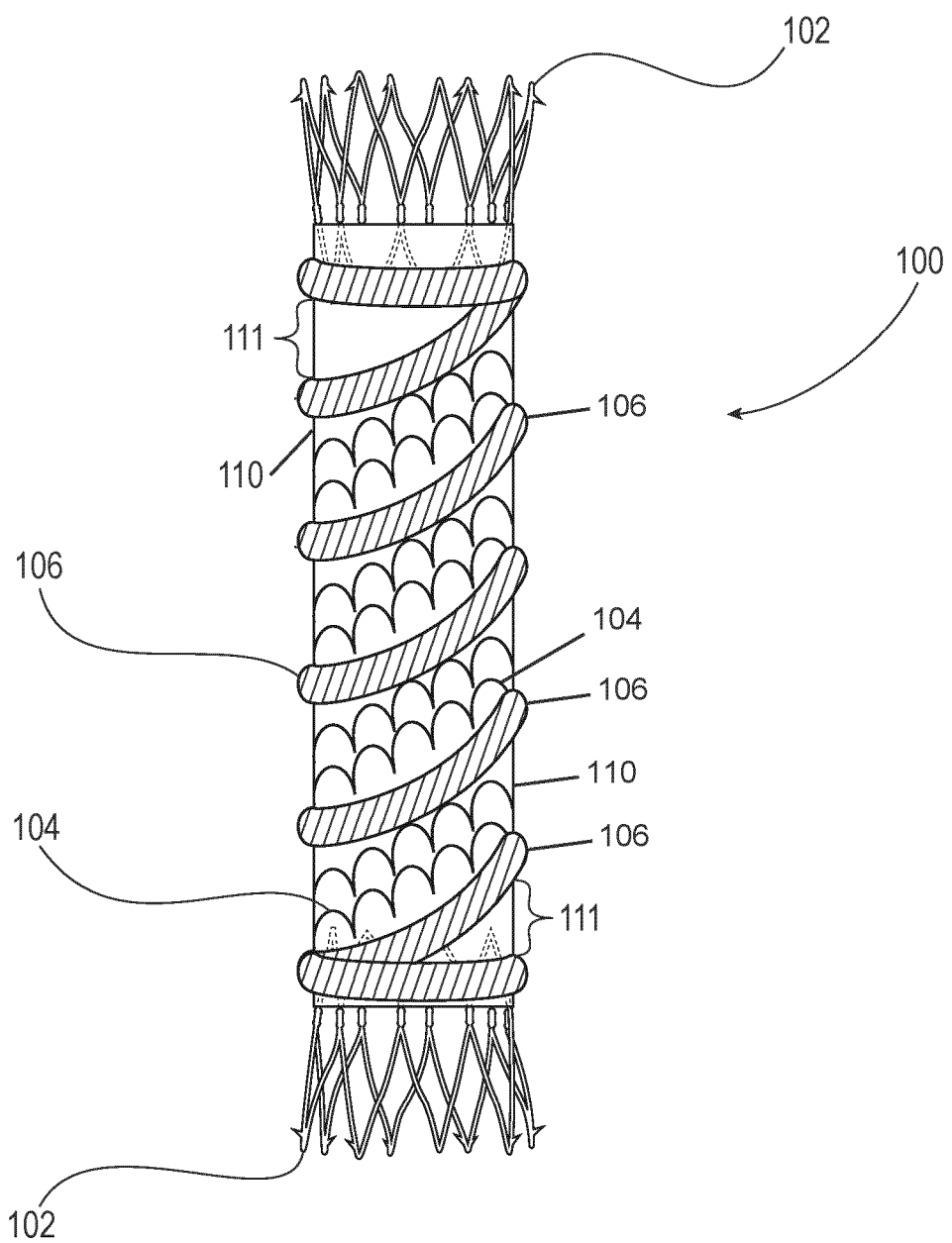
FIG. 1 shows an endovascular system in accordance with an arrangement.

FIG. 1 shows an endovascular system in accordance with an arrangement. An endovascular system in accordance with an arrangement includes a main tubular graft body 100 which includes wall portions 110 disposed between a plurality of inflatable channels 106. One or more stent segments 104 are disposed between two or more of the inflatable channels 106. In some examples, two of the wall portions 110 are connected by one of the inflatable channels 106. In various arrangements, each stent segment 104 is disposed on a surface of a corresponding wall portion 110 or laminated into the wall portion 110. As such, each stent segment 104 contacts or is embedded in the surface of a corresponding wall portion 110. The main tubular graft body 100 also includes wall portions 111 at both a proximal end of the main tubular graft body 100 and a distal end of the main tubular graft body 100. In some examples, the wall portions 111 do not have any stent segments 104 disposed thereon.

The main tubular graft body 100 also includes anchor members 102 disposed at both the distal end and the proximal end of the main tubular graft body 100. The anchor members 102 are attached to, embedded in, or otherwise fixed to the proximal end of the main tubular graft body 100 and the distal end of the main tubular graft body 100. The anchor members 102 are shown to be a stent-like scaffold structure. Other configurations of the anchor members 102 can be likewise implemented.

As shown in FIG. 1, in various arrangements the plurality of inflatable channels 106 are configured as helical rings. The inflatable channels 106 are disposed along the main tubular graft body 100 in a helical manner, coiling around the main tubular graft body 100. In one example, the inflatable channels 106 are a same, continuous channel that coils around the main tubular graft body 100, from the proximal end of the main tubular graft body 100 to the distal end of the main tubular graft body 100. In that regard, a fill line (not shown) connected or otherwise operatively coupled to any point of the continuous inflatable channels 106 can be used to fill the inflatable channels 106. In another example, two or more of the inflatable channels 106 are separated from one another. In that regard, each separate one of the inflatable channels 106 is filled with a fill line (not shown) connected or otherwise operatively coupled thereto. Alternative configurations or geometries can be likewise implemented.

Figure 2:
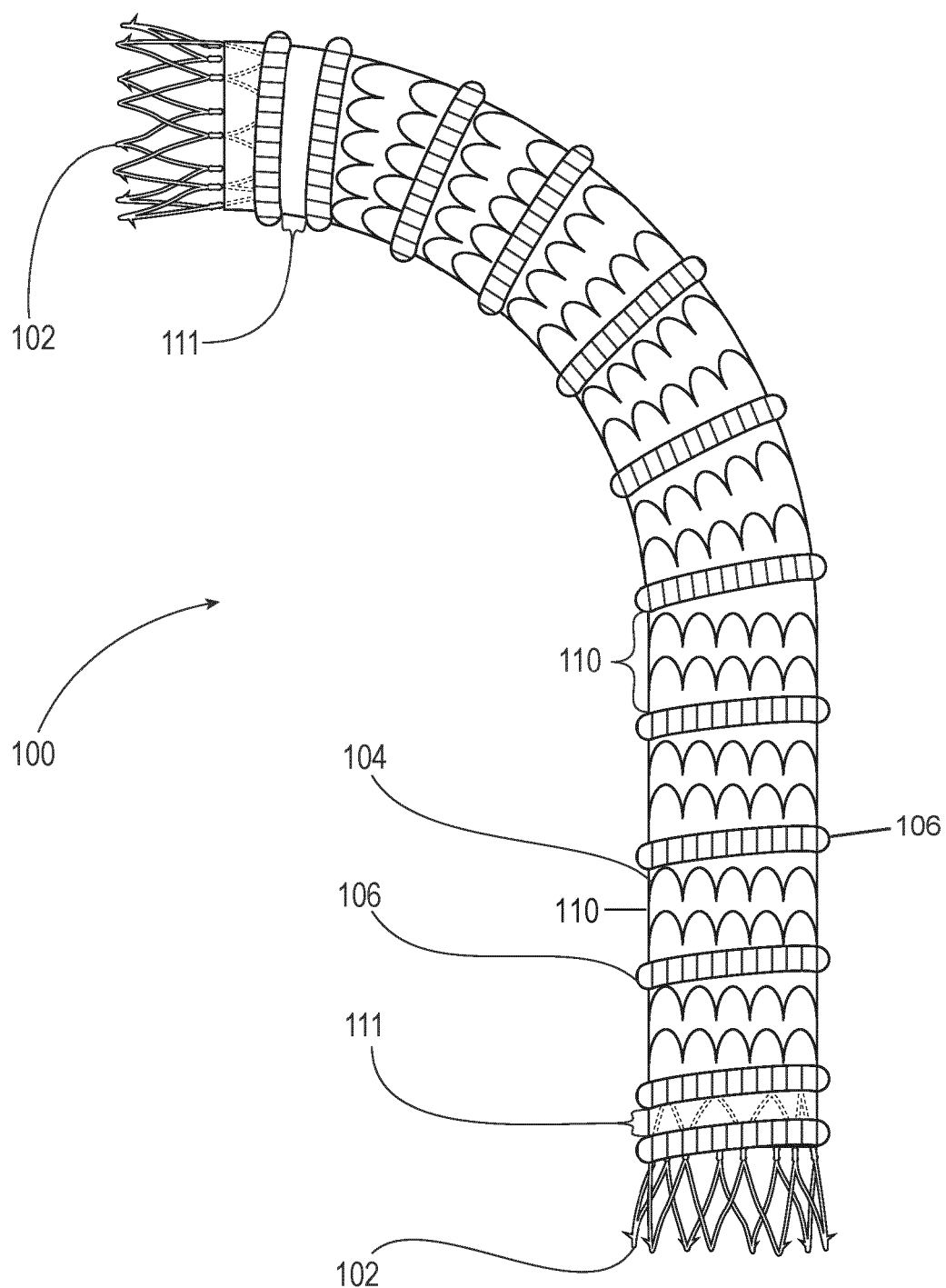
FIG. 2 shows an endovascular system after bending in accordance with an arrangement.

FIG. 2 shows an endovascular system of the present disclosure according to an arrangement that is similar to the arrangement of FIG. 1, but has annular (non-helical) inflatable channels 106 and is shown in a curved state. The endovascular system in FIG. 2 includes a main tubular graft body 100 that includes wall portions 110 disposed between a plurality of inflatable channels 106. At least one stent segment 104 is disposed between two or more inflatable channels 106 and is disposed on a surface of wall portions 110 or laminated within wall portions 110. The main tubular graft body 100 also includes wall portions 111 at both a proximal end of the main tubular graft body 100 and a distal end of the main tubular graft body 100. The main tubular graft body 100 also includes anchor members 102 disposed at both the distal end and the proximal end of the main tubular graft body 100. In FIG. 2, the main tubular graft body 100 is shown to be in a curved or bent state. The main tubular graft body 100, the wall portions 110 and 111, the anchor members 102, and the stent segment 104 are similar to those described with respect to FIG. 1. In various arrangements the plurality of inflatable channels 106 shown in FIG. 2 are configured as annular rings instead of helical channels.

In various arrangements, the inflatable channels 106 are annular rings and the stent segments 104 are segmented stent rings. In various arrangements, the annular inflatable channels 106 are non-helical. In some arrangements, the stent segments 104 are discrete, separate, and segmented stent rings nested in interstitial spaces between two adjacent inflatable channels 106. In various arrangements, the stent segments 104 (e.g., stent ring segments) are completely circumferential (O-shaped, around the main tubular graft body 100) around a circumference of the main tubular graft body 100. In some arrangements, the stent segments 104 are partially circumferential (such as being C-shaped instead of O-shaped). In various arrangements, the stent segments 104 (e.g., nested stent ring segments) are made in continuous segments between the inflatable channels 106 (e.g., annular rings) such that a zig pattern of the stent segments 104 can jump to an adjacent zig pattern within the inter-ring segment (e.g., a same wall portion 110). A resultant wire spine for the stent segments 104 can be aligned with a polymer spine fill channel (not shown) configured to fill the inflatable channels 106 (e.g., annular rings).

Figure 3A:
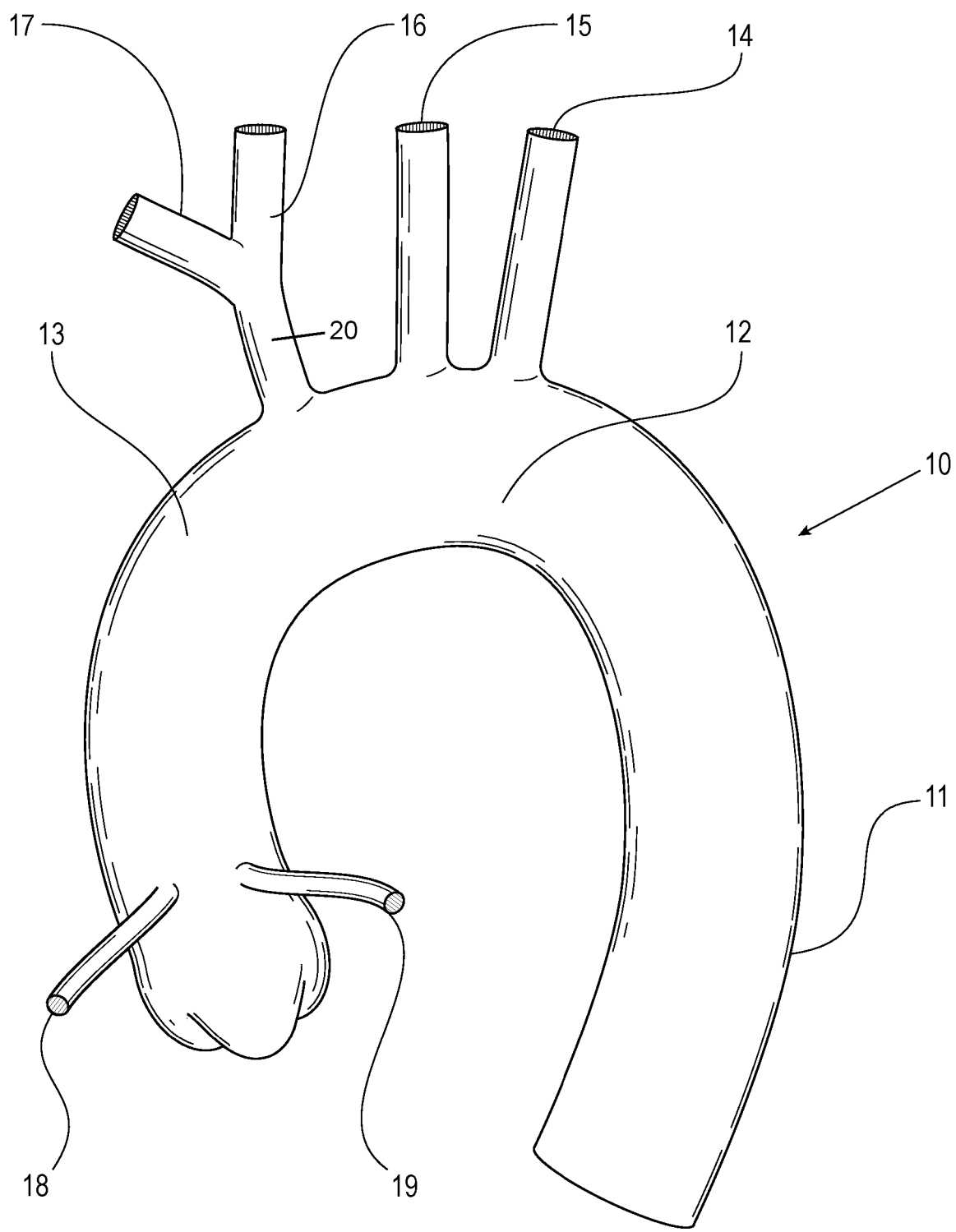
FIG. 3A shows an aorta including an aortic arch.

Referring to FIG. 3A, a typical configuration of an aorta 10 of a person is shown. The aorta 10 includes a descending aorta portion 11 (i.e., a distal aortic portion), an aortic arch portion 12, and an ascending aorta portion 13 (i.e., a proximal aortic portion). The aorta 10 is fluidically connected to the left subclavian artery 14, the left common carotid artery 15, the right common carotid artery 16, the right subclavian artery 17, the right coronary artery 18, and the left coronary artery 19. The great vessels arise off the aortic arch portion 12 and include the innominate artery (also known as the brachiocephalic artery) 20, the left common carotid artery 15, and the left subclavian artery 14, which are referred to as the aortic arch vessels. The innominate artery (also known as the brachiocephalic artery) 20 divides into the right common carotid artery 16 and the right subclavian artery 17.

Figure 3B:
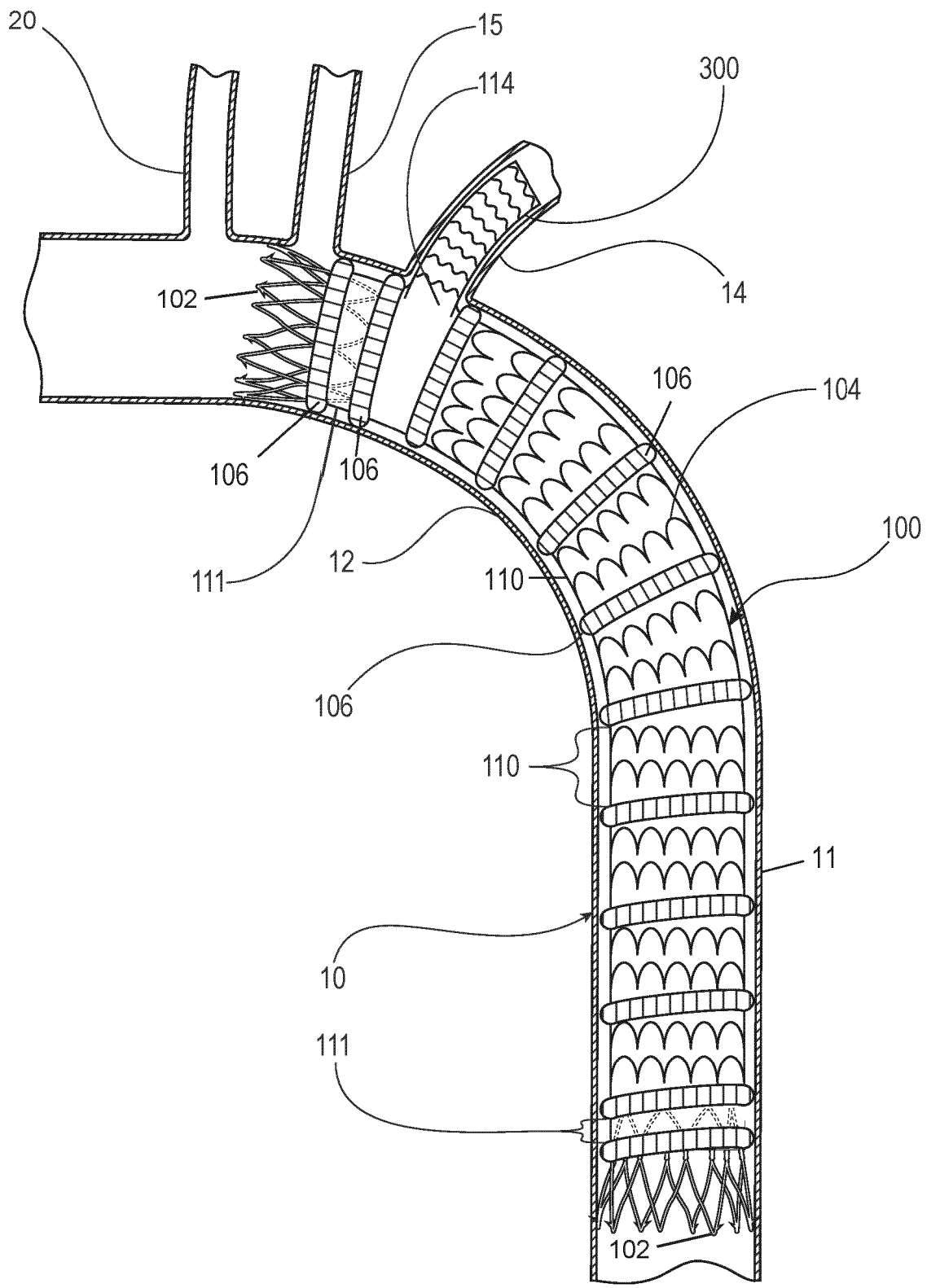
FIG. 3B shows an endovascular system in accordance with an arrangement deployed in an aortic arch.

FIG. 3B shows an endovascular system of the present disclosure in accordance with an arrangement as deployed in an aorta 10 of a typical person. An endovascular system in accordance with various arrangements as shown in FIG. 3B has a fenestration 114 and includes a branched device 300 for insertion into the left subclavian artery 14. The endovascular system in FIG. 3B includes a main tubular graft body 100 including wall portions 110 disposed between a plurality of inflatable channels 106 in the manner described herein. In one example, the inflatable channels 106 are annular rings (e.g., FIG. 2). In other examples, the inflatable channels 106 are helical rings (e.g., FIG. 1). The inflatable channels 106 in FIG. 3B are filled by a fill line (not shown). In other examples, the inflatable channels 106 are filled by two or more fill lines (not shown). The inflatable channels 106 are shown to be inflated in the aorta 10, contacting and/or in friction fit with the walls of the aorta 10 to structurally support the main tubular graft body 100 in the aorta 10. The main tubular graft body 100 is inserted into the aortic arch portion 12 and the descending aorta portion 11. As shown, the main tubular graft body 100 curves in accordance with the shape of the aortic arch portion 12. At least one stent segment 104 is disposed between two or more inflatable channels 106 and are disposed on a surface of wall portions 110 or are laminated within wall portions 110. The main tubular graft body 100 also includes wall portions 111 at both a proximal end of the main tubular graft body 100 and a distal end of the main tubular graft body 100. One of the wall portions 111 and two inflatable channels 106 (two annular rings) are disposed in the aortic arch portion 12 between the left common carotid artery 15 and the left subclavian artery 14. One of the two inflatable channels 106 (two annular rings) contacts a portion of the aorta wall next to the left common carotid artery 15 and another contacts a portion of the aorta wall next to the left subclavian artery 14. The main tubular graft body 100 also includes anchor members 102 disposed at both the distal end and the proximal end of the main tubular graft body 100. One of the anchor members 102 is configured to be disposed in the aortic arch portion 12 near the left common carotid artery 15. The one of the anchor members 102 is configured to contact a wall of the aortic arch portion 12 between the left common carotid artery 15 and the innominate artery 20.

The main tubular graft body is deployed in the aorta 10, including in the aortic arch portion 12, as described. The main tubular graft body 100 has a fenestration 114 configured to be located once the endovascular system is deployed in the aorta 10 to be in fluid connection with at least one of the greater arch vessels, such as the left subclavian artery 14, such that a branch graft 300 deployed in at least one of the greater arch vessels is in fluid connection with the fenestration 114 of the main tubular graft body 100. Such configurations allows blood to flow from the main tubular graft body 100 to the at least one of the greater arch vessels (such as the left subclavian artery 14). The two inflatable channels 106 (between the left common carotid artery 15 and the left subclavian artery 14) and one of the anchor members 102 (a portion of which is between the left common carotid artery 15 and the innominate artery 20) anchor and stabilize the main tubular graft body 100 and the branch graft 300. The two inflatable channels 106 (between the left common carotid artery 15 and the left subclavian artery 14) and one of the anchor members 102 (between the left common carotid artery 15 and the innominate artery 20) extends sufficiently toward the ascending aorta to stabilize the main tubular graft body 100 and the branch graft 300 and reduce the stress that the branch graft 300 has on the left subclavian artery 14.

Figure 4A:
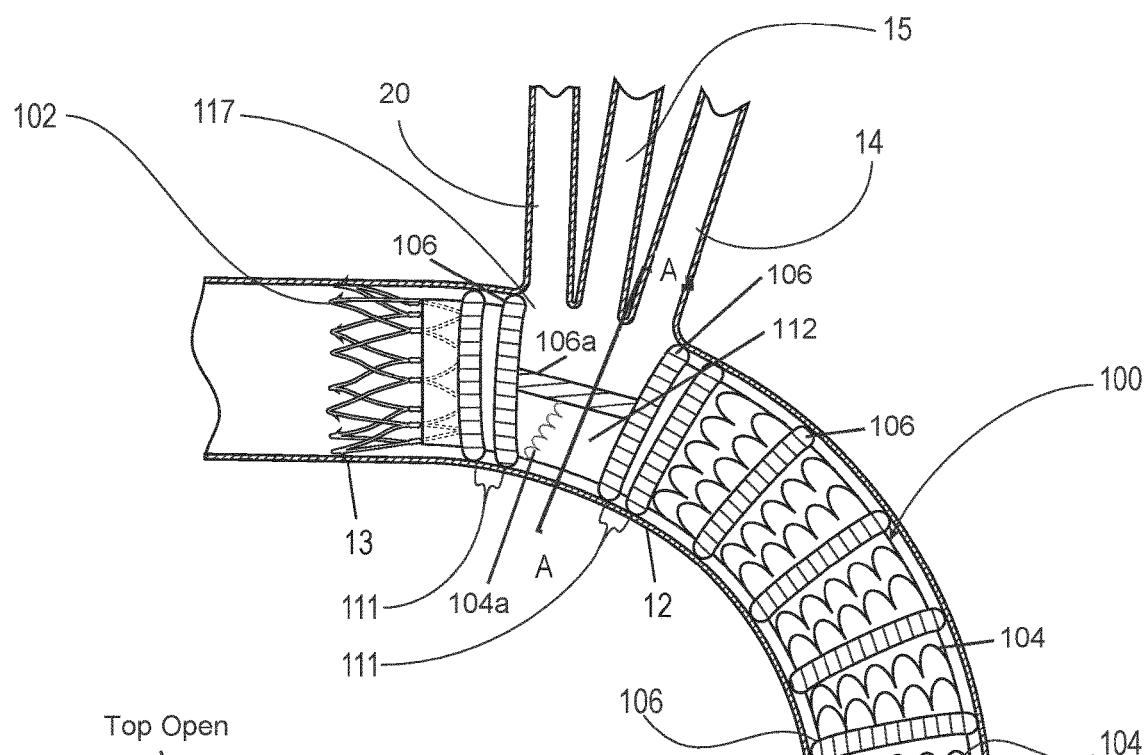
FIG. 4A shows an endovascular system in accordance with an arrangement deployed in an aortic arch.
Figure 4B:
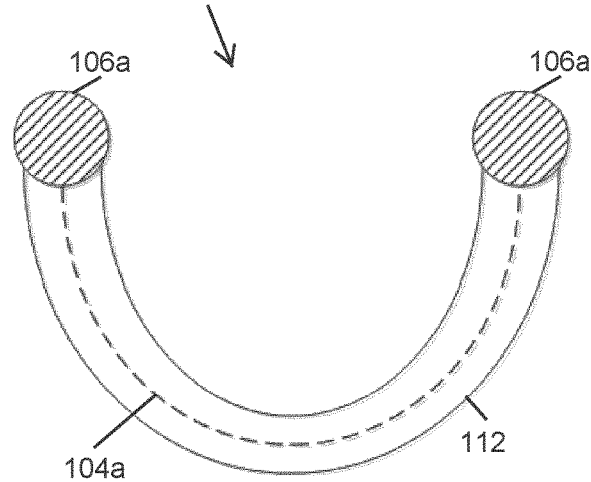
FIG. 4B is a cross-sectional view of FIG. 4A.

FIGS. 4A and 4B show an endovascular system in accordance with an arrangement as deployed in the aortic arch portion 12 of a person. In various arrangements, the endovascular system as shown in FIGS. 4A and 4B includes a main tubular graft body 100 including wall portions 110 disposed between a plurality of inflatable channels 106 in the manner described herein. In one example, the inflatable channels 106 are annular rings (e.g., FIG. 2). In other examples, the inflatable channels 106 are helical rings (e.g., FIG. 1). In the arrangement of FIG. 4A, the inflatable channels 106 are filled through a fill line (not shown). In other examples, the inflatable channels 106 are filled by two or more fill lines (not shown). The inflatable channels 106 are shown to be inflated in the aorta 10, contacting and/or in friction fit with the walls of the aorta 10 to structurally support the main tubular graft body 100 in the aorta 10. The main tubular graft body 100 is inserted into the aortic arch portion 12 and the descending aorta portion 11. As shown, the main tubular graft body 100 curves in accordance with the shape of the aortic arch portion 12. One or more stent segments 104 are disposed between two or more inflatable channels 106 and are disposed on a surface of wall portions 110 or are laminated within wall portions 110. The main tubular graft body 100 also includes wall portions 111 at both a proximal end of the main tubular graft body 100 and a distal end of the main tubular graft body 100. The main tubular graft body 100 also includes anchor members 102 disposed at both the distal end and the proximal end of the main tubular graft body 100. The main tubular graft body 100 is deployed in the aorta 10, including in the aortic arch.

The main tubular graft body 100 has a fenestration 117 configured to be in fluid connection with at least one of the greater arch vessels when the endovascular system is deployed within an aorta of a person. As shown in FIG. 4A, the fenestration 117 is bounded by two of the inflatable channels 106. In various embodiments, one of the wall portions 111, two inflatable channels 106, and one of the anchor members 102 are configured to be disposed in the ascending aorta. In some arrangements, one of the inflatable channels 106 is disposed on a portion of the aorta wall next to the innominate artery 20. In some embodiments, at least one of the wall portions 111 is configured to be disposed in the descending aorta portion 11. In some arrangements, one of the inflatable channels 106 is disposed on a portion of the aorta wall next to the left subclavian artery 14. In other words, in various arrangements, the fenestration 117 is bounded by two of the inflatable channels 106 at the edges of the innominate artery 20 and the left subclavian artery 14. In some examples, the fenestration 117 extends an entirety of a distance between the two or more adjacent inflatable channels 106.

Such configurations allows blood to flow from the main tubular graft body 100 to the at least one of the greater arch vessels (such as the left subclavian artery 14, the left common carotid artery 15, and the innominate artery 20). The inflatable channels 106, particularly the two inflatable channels 106 at the edges of the innominate artery 20 and the left subclavian artery 14 and one of the anchor members 102 (a portion of which may be disposed in the ascending aorta portion 13) anchor and stabilize the main tubular graft body 100 and the fenestration 117. In some arrangements, one or more of the inflatable channels 106 and one of the anchor members 102 (in ascending aorta portion 13) extend sufficiently into the ascending aorta portion 13 to stabilize the main tubular graft body 100 and the fenestration 117 and reduce the stress that the fenestration 117 has on the greater arch vessels (such as the left subclavian artery 14, the left common carotid artery 15, and the innominate artery 20).

The fenestration 117 is bounded by one or more connecting inflatable channels (e.g., a connecting inflatable channel 106a) that connect the two adjacent inflatable channels 106 that are disposed at the left subclavian artery 14 and the innominate artery 20. The main tubular graft body 100 includes a wall portion 112 connected to the one or more connecting inflatable channels 106a and located below the fenestration 117. In various arrangements, the endovascular system includes one or more stent segments 104a disposed on a surface of the wall portion 112 or laminated within the wall portion 112. As shown in FIG. 4B, in various arrangements, the one or more stent segments 104a is laminated within the wall portion 112. As shown in FIG. 4B, in various arrangements the wall portion 112 has a semi-circular cross-sectional shape (e.g., a C-shaped cross-section), with the opening ("Top Open") in the C-shaped cross-section being the fenestration 117 shown in FIG. 4A. In some arrangements, the fenestration 117 has a semi-circular cross-sectional shape (e.g., a C-shaped cross-section), a half-circular cross-sectional shape, or the like. The one or more stent segments 104a, the wall portion 112, and the connecting inflatable channel 106a structurally support the fenestration 117. In various arrangements, the inflatable channels 106 and the connecting inflatable channels 106a are fillable with a polymer, such that a single fill line (not shown) can fill the inflatable channels 106 and the connecting inflatable channels 106a. For example, polymer can be filled to the inflatable channels 106 in the descending aorta portion 11 and through the connecting inflatable channels 106a to the inflatable channels 106 in the ascending aorta portion 13, such that all of the inflatable channels 106 and the connecting inflatable channels 106a can be filled.

Various arrangements, such as the arrangement of FIG. 4A, provide a kink resistant version of a large fenestrated graft with polymer sealing rings (e.g., the two adjacent inflatable channels 106 that are disposed at the left subclavian artery 14 and the innominate artery 20). In various arrangements, structural support in the arch and open fenestration areas are shared by the polymer rings and stent components in the interstitial areas between the polymer rings. In some arrangements, there is a continuous stent mesh over a fenestration for additional luminal support. In some arrangements, the stent mesh is laminated into the graft and one or more sealing rings.

Figure 5:
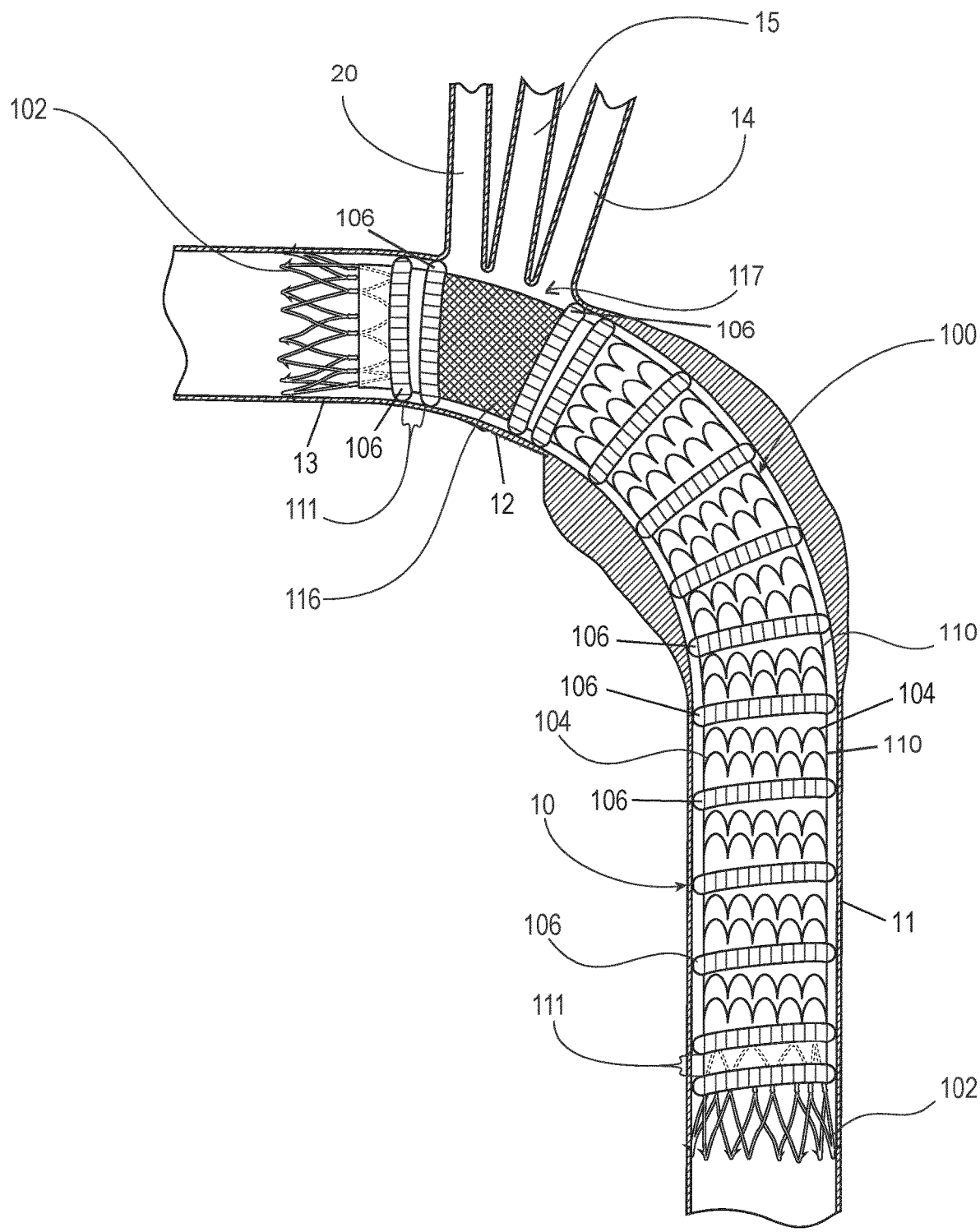
FIG. 5 shows an endovascular system in accordance with an arrangement deployed in an aortic arch.

FIG. 5 shows an endovascular system in accordance with an arrangement as deployed in the aorta 10 of a person. The endovascular system as shown in FIG. 5 includes a main tubular graft body 100 including wall portions 110 disposed between a plurality of inflatable channels 106 in the manner described herein. In one example, the inflatable channels 106 are annular rings (e.g., FIG. 2). In other examples, the inflatable channels 106 are helical rings (e.g., FIG. 1). In the arrangement of FIG. 5, the inflatable channels 106 are filled by a fill line (not shown). In other examples, the inflatable channels 106 are filled by two or more fill lines (not shown). The inflatable channels 106 are shown to be inflated in the aorta 10, contacting and/or in friction fit with the walls of the aorta 10 to structurally support the main tubular graft body 100 in the aorta 10. The main tubular graft body 100 is inserted into the aortic arch portion 12, the ascending aorta portion 13, and the descending aorta portion 11. As shown, the main tubular graft body 100 curves in accordance with the shape of the aortic arch portion 12. At least one stent segment 104 is disposed between two or more inflatable channels 106 and is disposed on a surface of wall portions 110 or integrated within wall portions 110. The main tubular graft body 100 also includes wall portions 111 at both a proximal end of the main tubular graft body 100 and a distal end of the main tubular graft body 100. The main tubular graft body 100 also includes anchor members 102 disposed at both the distal end and the proximal end of the main tubular graft body 100. The main tubular graft body 100 is deployed in the aorta 10, including in the aortic arch.

The main tubular graft body 100 has a fenestration 117 configured to be in fluid connection with at least one of the greater arch vessels when the endovascular system of FIG. 5 is deployed within the aorta 10 of a person. As shown in FIG. 5, in some arrangements, one of the wall portions 111, two inflatable channels 106, and one of the anchor members 102 are configured to be disposed in the ascending aorta portion 13, and one of the inflatable channels 106 is disposed on a portion of the aorta wall next to the innominate artery 20. In some arrangements, the other one of the wall portions 111, the rest of the inflatable channels 106, and the other one of the wall portions 111 are configured to be disposed in the descending aorta portion 11. In some arrangements, one of the inflatable channels 106 is disposed on a portion of the aorta wall next to the left subclavian artery 14. In other words, in some arrangements the fenestration 117 is bounded by two of the inflatable channels 106 at the edges of the innominate artery 20 and the left subclavian artery 14. In some examples, the fenestration 117 extends an entirety of a distance between two or more adjacent inflatable channels 106.

Such configurations allows blood to flow from the main tubular graft body 100 to at least one of the greater arch vessels (such as the left subclavian artery 14, the left common carotid artery 15, and the innominate artery 20). The inflatable channels 106, particularly the two inflatable channels 106 at the edges of the innominate artery 20 and the left subclavian artery 14 and one of the anchor members 102 (a portion of which is disposed in the ascending aorta portion 13) anchor and stabilize the main tubular graft body 100 and the fenestration 117. In some arrangements, two inflatable channels 106 and one of the anchor members 102 (in ascending aorta portion 13) extend sufficiently into the ascending aorta portion 13 to stabilize the main tubular graft body 100 and the fenestration 117 and reduce the stress on the greater arch vessels (such as the left subclavian artery 14, the left common carotid artery 15, and the innominate artery 20).

As shown in FIG. 5, in various arrangements the fenestration 117 is covered by a continuous stent mesh 116 in the location of the fenestration 117 for additional luminal support. The continuous stent mesh 116 (e.g., with an O-shaped cross-section), in one example, covers the entirety of the fenestration 117. In another example, the continuous stent mesh 116 (e.g., with a C-shaped cross-section) covers only a portion of the fenestration 117. In various arrangements, the main tubular graft body 100 includes the stent mesh 116 and the stent mesh 116 is connected to and is between two adjacent inflatable channels 106 (at the edges of the innominate artery 20 and the left subclavian artery 14). Thus, the stent mesh 116 connects the portion of the endovascular system that is in the ascending aorta portion 13 with the portion of the endovascular system that is in the descending aorta portion 11, without hindering blood flow. In various arrangements, the stent mesh 116 is configured to allow blood to flow through the stent mesh 116 between the greater arch vessels and a lumen created by the main tubular graft body 100. In some arrangements, the stent mesh 116 is laminated into two adjacent inflatable channels 106. In some arrangements, the stent mesh 116 is laminated into a graft material of the main tubular graft body 100.

In various arrangements, the wall portions 110 and the wall portions 111 are formed of any suitable material such as, for example, thin PTFE. In various arrangements, the plurality of inflatable channels 106 can be filled by a polymer material.

In various arrangements, the one or more stent segments 104 are connected to a surface of the graft by any suitable technique. For example, in some arrangements, the one or more stent segments 104 are intimately laminated on an inner surface of the graft. As a further example, in some arrangements, the one or more stent segments 104 are adhered or bonded to an inner surface of the graft. As a still further example, in some arrangements, the one or more stent segments 104 are sutured on the inner surface of the graft. As a still further example, in some arrangements, the one or more stent segments 104 are glued on an inner surface of the graft.

The one or more stent segments 104 are formed of any suitable material. For example, in some arrangements the one or more stent segments 104 are formed of Nitinol. As a further example, in some arrangement, the one or more stent segments 104 are formed of wire. As a still further example, in some arrangements the one or more stent segments 104 are formed of a laser cut material.

In various arrangements, the one or more stent segments 104 provide luminal support for the main tubular graft body 100 of the endovascular system. In various arrangements, the one or more stent segments 104 are configured to keep the lumen of the main tubular graft body 100 open while the main tubular graft body 100 is curved when it is deployed in an aorta of a person including in an aortic arch. With reference to FIGS. 4A and 5, in some arrangements an endovascular system may have the structure as shown in FIG. 4A with the one or more connecting inflatable channels 106a, and may also include the stent mesh 116 of FIG. 5 in which case the stent mesh 116 may be attached to the one or more connecting inflatable channels 106a.

Various arrangements provide for thoracic ascending aorta and aortic arch transcatheter endograft solutions. An endovascular stent graft or stent graft system for placement in a thoracic endoluminal space in accordance with various arrangements allows perfusion of blood to the greater arch vessels including, for example, the brachiocephalic trunk, left common carotid, and left subclavian artery. A thoracic stent graft system in accordance with an arrangement employs a parallel stent that is open in nature and in apposition to aortic arch vessels which are then perfused via a bare stent in an ascending or arch region. In some arrangements, the thoracic stent graft system includes a stent graft that employs polymer to seal, such as with an endobag or rings, in the aorta and around the open parallel stent, therefore stabilizing and anchoring the stent graft system. In some arrangements, active fixation may be incorporated into the stent if needed.

Figure 6A:
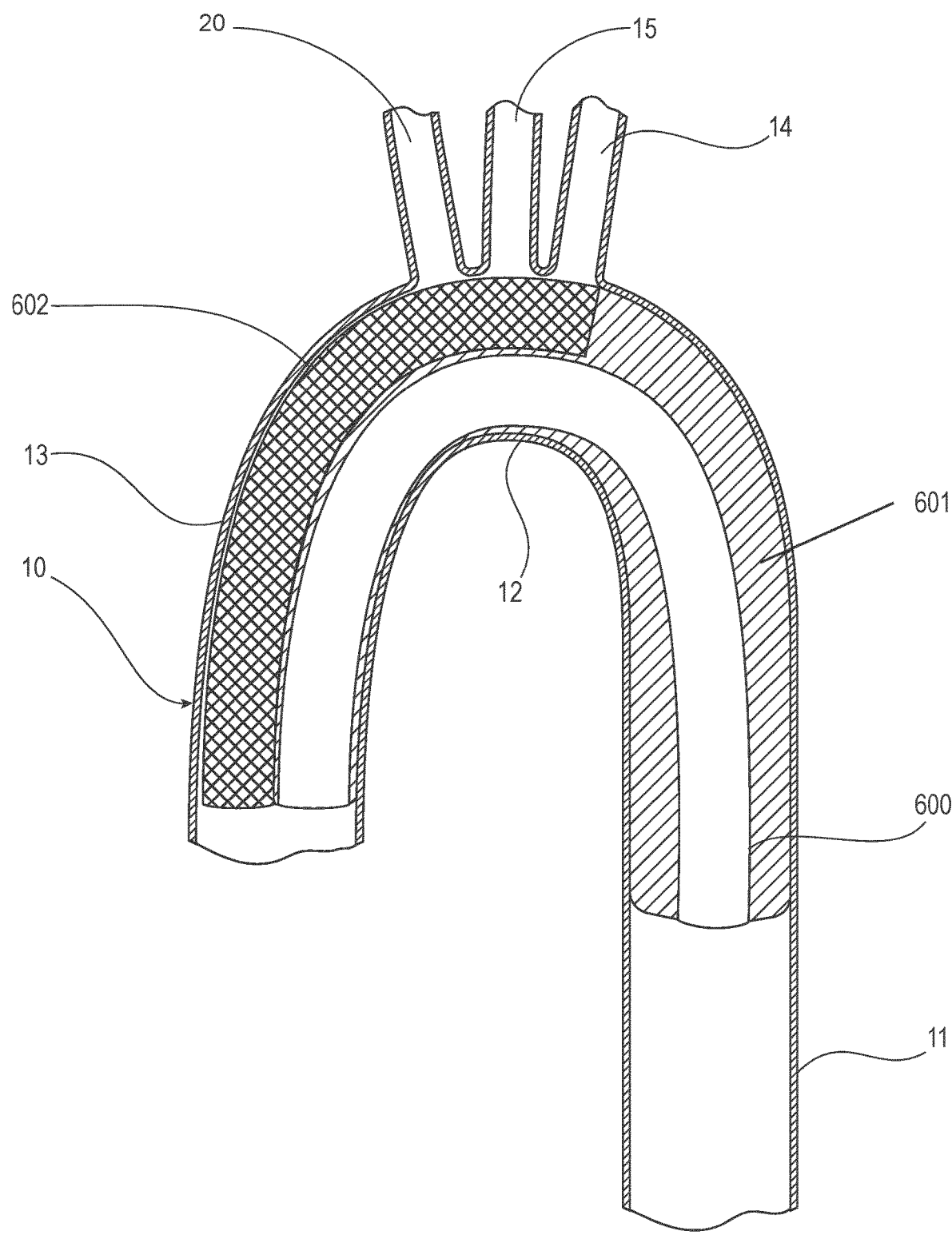
FIG. 6A shows an endovascular system in accordance with an arrangement deployed in an aortic arch.

FIG. 6A shows an endovascular system in accordance with an arrangement. The endovascular system is configured to be generally placed in a thoracic endoluminal space of a person's aorta 10. As shown in FIG. 6A, the endovascular system includes a first tubular graft body 600 configured to pass continuously from the ascending aorta portion 13 over the aortic arch portion 12 and to the descending aorta portion 11. The endovascular system in FIG. 6A further includes a second tubular graft body 602 which runs parallel to the first tubular graft body 600 and in apposition to the aortic arch vessels that allows for perfusion of the aortic arch vessels. The second tubular graft body 602 is configured to pass from the ascending aorta portion 13 over the aortic arch portion 12. The second tubular graft body 602 extends over openings in the aorta wall to the innominate artery 20, the left common carotid artery 15, and the left subclavian artery 14 to allow blood flow. The second tubular graft body 602 is closer to the greater arch vessels (e.g., the innominate artery 20, the left common carotid artery 15, and the left subclavian artery 14) than the first tubular graft body 600. The second tubular graft body 602 is between the first tubular graft body 600 and the greater arch vessels. An end of the second tubular graft body 602 is at a portion in the aorta wall that is next to an end of the left subclavian artery 14. In one example, the second tubular graft body 602 is formed entirely of mesh.

The endovascular system of FIG. 6A also includes a fillable bag (e.g., an endobag) 601, fillable by a fill line (not shown). The fillable bag 601 can be attached or otherwise fixed to the exterior of the first tubular graft body 600. The fillable bag 601 can be filled with a fill medium to achieve an inflated or filled state. The fill medium can push a wall of the fillable bag 601 against the aorta wall. A portion of the fillable bag 601 extends into a space of the aorta 10 adjacent to the first tubular graft body 600. That is, when in an uninflated state, the fillable bag 601 can be confined to being around the first tubular graft body 600, but when inflated (in the filled state) as shown, the fillable bag 601 expands radially to fill at least a portion of a space in the aorta 10 around the first tubular graft body 600 that is not covered by the second tubular graft body 602. In some arrangements, a portion of the fillable bag 601 is between the first tubular graft body 600 and the second tubular graft body 602, for example, in the ascending aorta portion 13 and the aortic arch portion 12. This allows the fillable bag 601 to push against the second tubular graft body 602 when the fillable bag 601 is filled, to maintain the position and configuration of the first tubular graft body 600 and the second tubular graft body 602. In some arrangements, the fillable bag 601 can be further attached or otherwise fixed to the exterior (e.g., a circumferential surface and/or an end) of the second tubular graft body 602.

In various arrangements, the endovascular system shown in FIG. 6A, which includes both the first tubular graft body 600 and the second tubular graft body 602, provides an open stent structure in the region of the aortic arch vessels (e.g., the innominate artery 20, the left common carotid artery 15, and the left subclavian artery 14) which are then perfused via the graft-free open fenestration in the ascending arch region (e.g., the ascending aorta portion 13) of the second tubular graft body 602 in apposition with the aortic arch vessels. Such a configuration provides for easy use and eliminates a need of wire manipulation in the greater vessels of the aortic arch portion 12, thus reducing an associated risk of stroke with the endovascular repair.

Figure 6B:
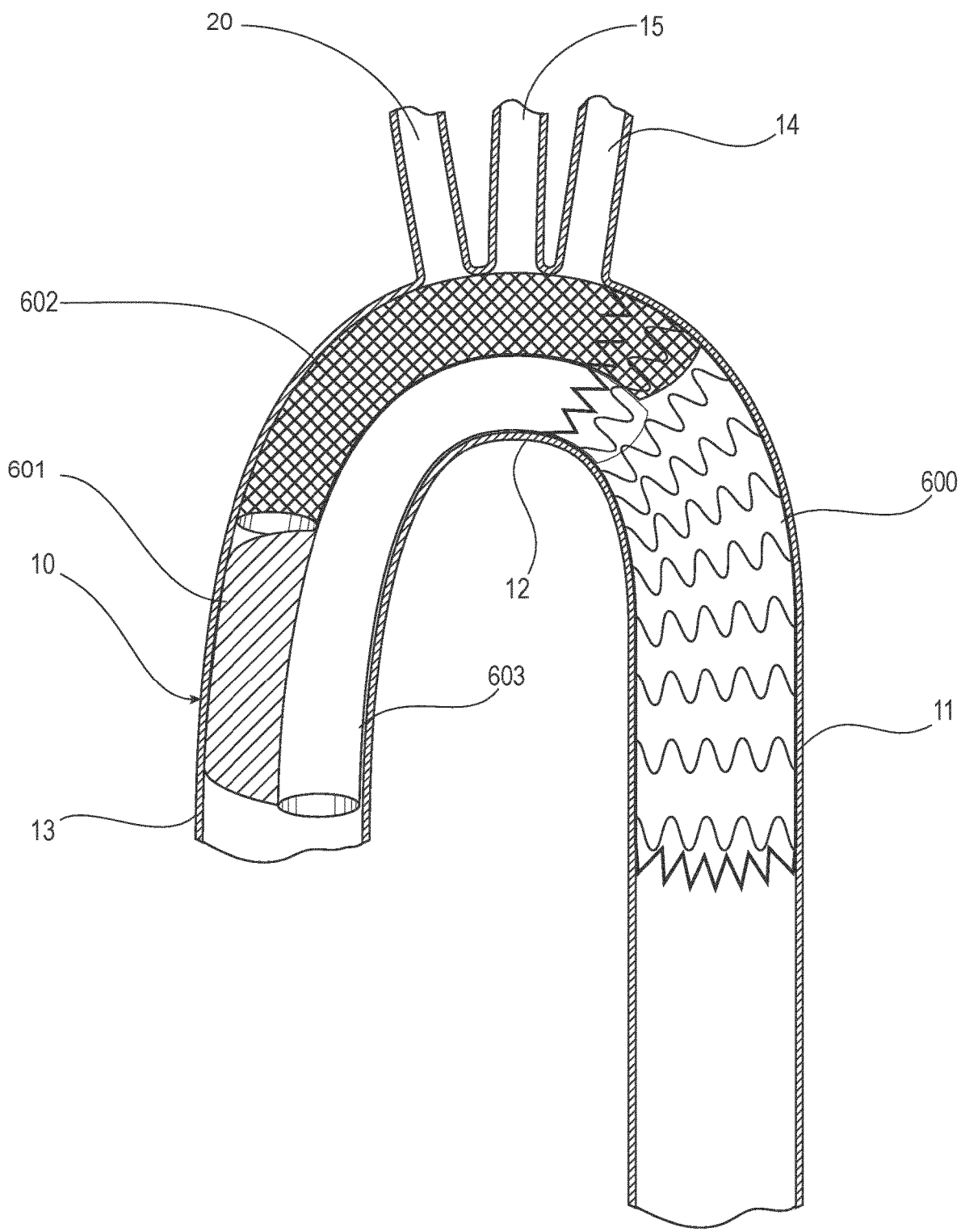
FIG. 6B shows an endovascular system in accordance with an arrangement deployed in an aortic arch.

Further, different configurations of the exemplary arrangements shown in FIGS. 6A and 6B are useful for different flow conditions. For example, some configurations such as that shown in FIG. 6A are useful for antegrade flow while other configurations such as that shown in FIG. 6B are useful for retrograde flow. FIG. 6B shows an endovascular system in accordance with an arrangement that includes a first tubular graft body 600 configured to pass from the aortic arch portion 12 to the descending aorta portion 11. The first tubular graft body 600 includes a stent structure. The first tubular graft body 600 extends from a portion of the aorta wall next to the left subclavian artery 14, toward the descending aorta portion 11. The endovascular system of FIG. 6B further includes a second tubular graft body 602 which in in fluid connection with the first tubular graft body 600 and passes from the ascending aorta portion 13 to the aortic arch portion 12 and is in apposition to the aortic arch vessels. A portion of the second tubular graft body 602 overlaps with a portion of first tubular graft body 600. In some arrangements, at least one stent segment of the first tubular graft body 600 overlaps with the second tubular graft body 602. In some arrangements, the second tubular graft body 602 is formed entirely of mesh.

The endovascular system also includes a third tubular graft body 603 configured to be deployed in the ascending aorta portion 13 and the aortic arch portion 12 and is configured to be in fluidic connection with the first tubular graft body 600. A portion of the third tubular graft body 603 overlaps with a portion of first tubular graft body 600. In some arrangements, at least one stent segment of the first tubular graft body 600 overlaps with the third tubular graft body 603. In some arrangements, at least one stent segment of the first tubular graft body 600 can surround the second tubular graft body 602 and the third tubular graft body 603, to improve structural integrity with respect to connections from the first tubular graft body 600 to the second tubular graft body 602 and the third tubular graft body 603. The third tubular graft body 603 extends further into the ascending aorta portion 13 as compared to the second tubular graft body 602. The third tubular graft body 603 is longer than the second tubular graft body 602.

In various arrangements, the endovascular system shown in FIG. 6B also includes a fillable bag (e.g., endobag) 601. The fillable bag 601 is configured to provide sealing for the endovascular system next to a portion of the third tubular graft body 603. In particular, the fillable bag 601 is configured to provide a seal in a proximal portion (e.g., the ascending aorta portion 13 and/or the aortic arch portion 12) of an arch portion of the main artery (e.g., the aorta 10). In some examples, the fillable bag 601 is attached or otherwise fixed to the portion of the tubular graft body 603 that extends beyond the second tubular graft body 602. Thus, blood in the second tubular graft body 602 does not flow past the fillable bag 601. As the fillable bag 601 is being filled, the fillable bag 601 extends to push against the tubular graft body 603 and the aorta wall, thus anchoring the end of the tubular graft body 603 extending beyond the second tubular graft body 602.

In some arrangements such as the arrangement of FIG. 6A, an antegrade flow system is provided to perfuse the arch vessels. In some arrangements such as the arrangement in FIG. 6B, a retrograde flow system is provided to perfuse the arch vessels. In various arrangements, the systems shown in systems of FIGS. 6A and 6B are parallel stent graft systems, meaning that the first tubular graft body 600 and the second tubular graft body 602 in FIG. 6A are parallel to each other, and that the second tubular graft body 602 and the third tubular graft body 603 in FIG. 6B are parallel to each other. The parallel stent graft systems, such as the systems of FIGS. 6A and 6B are generally tubular in nature and are comprised of wire wound or laser cut stents of suitable material which may be self-expanding, such as nitinol, or may be balloon expandable, such as 316L Stainless Steel or L605 cobalt chromium, and may be bare, generally encapsulated, or partially encapsulated in PTFE graft material. In various arrangements such as in FIGS. 6A and 6B, a parallel stent graft system has an open stent structure in the region of the aortic arch vessels which are then perfused via the graft-free open fenestration in the ascending and arch region of the parallel stent in apposition with the vessels. Such systems may allow for ease of use and no wire manipulation in the greater vessels of the arch therefore reducing the associated stroke risk of the endovascular repair.

Figure 7A:
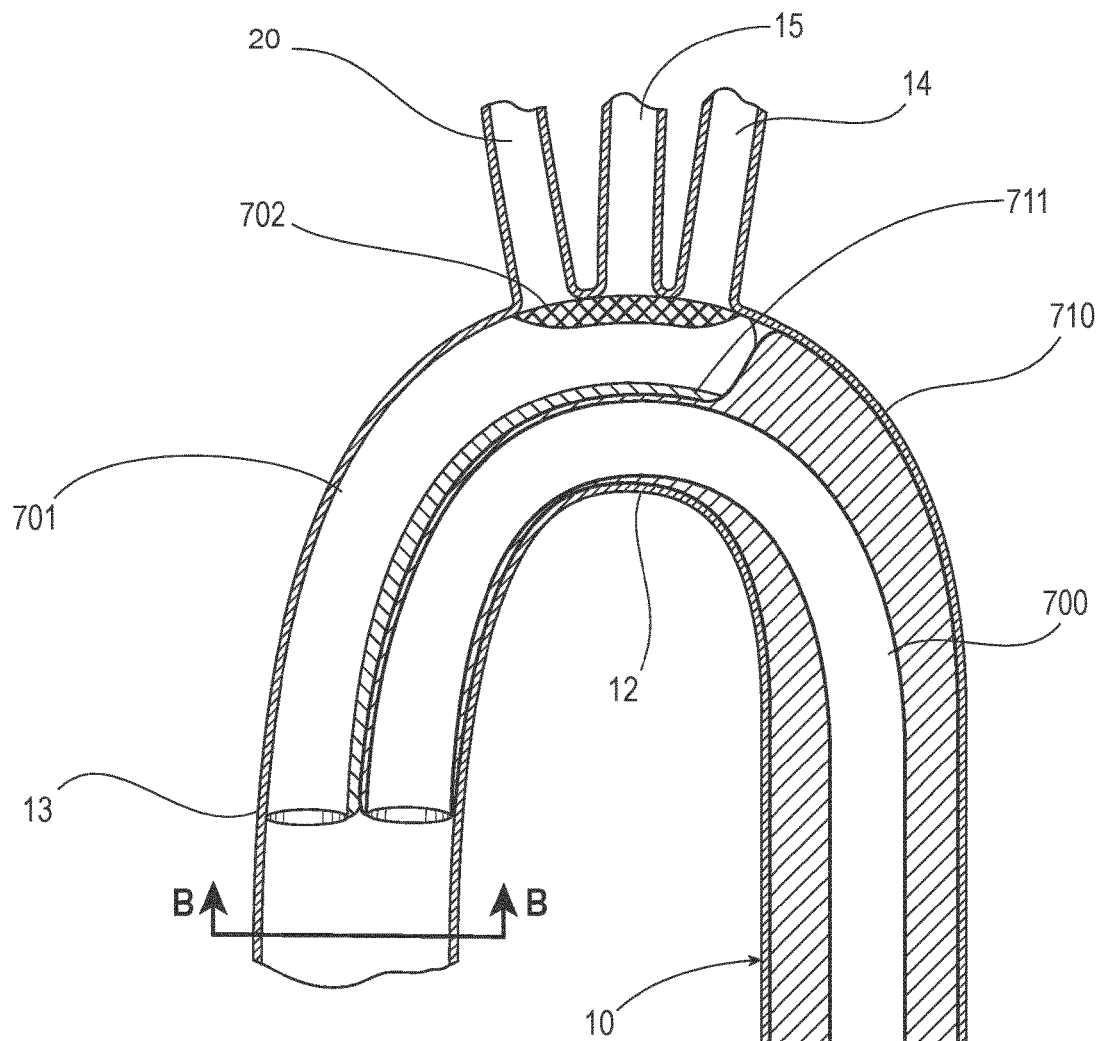
FIG. 7A shows an endovascular system in accordance with an arrangement deployed in an aortic arch.
Figure 7B:
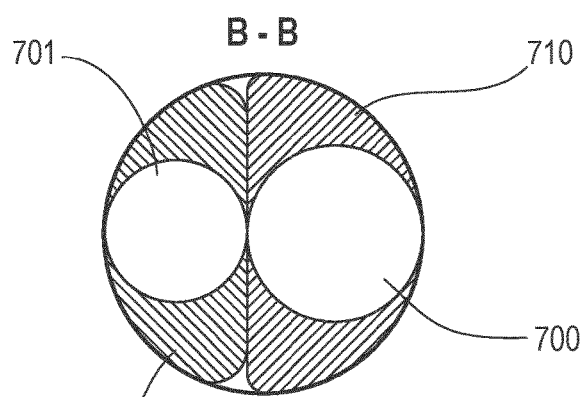
FIG. 7B is a cross-sectional view of a section of FIG. 7A.

FIGS. 7A and 7B show an endovascular system in accordance with an arrangement. The endovascular system in FIGS. 7A and 7B is configured to be generally placed in a thoracic endoluminal space of a person's aorta 10. As shown in FIG. 7A, the endovascular system includes a first tubular graft body 700 that extends from the ascending aorta portion 13 to the aortic arch portion 12 and to the descending aorta portion 11. The endovascular system in FIG. 7A further includes a second tubular graft body 701 that extends from the ascending aorta portion 13 to the aortic arch portion 12 and allows for perfusion of the aortic arch vessels. In various arrangements, the second tubular graft body 701 includes a fenestration 702 disposed in fluid connection with at least one of the greater arch vessels. In one example, the second tubular graft body 701 includes a mesh in the fenestration 702 through which blood can pass. The second tubular graft body 701 (and the fenestration 702) extends over openings in the aorta wall to the innominate artery 20, the left common carotid artery 15, and the left subclavian artery 14 to allow blood flow. The fenestration 702 is configured to be disposed at the openings in the aorta wall to the innominate artery 20, the left common carotid artery 15, and the left subclavian artery 14 to allow blood flow. The second tubular graft body 701 is closer to the greater arch vessels (e.g., the innominate artery 20, the left common carotid artery 15, and the left subclavian artery 14) than the first tubular graft body 700. The second tubular graft body 701 (and the fenestration 702) is between the first tubular graft body 700 and the greater arch vessels. An end of the second tubular graft body 602 is at a portion in the aorta wall that is next to an end of the left subclavian artery 14.

In various arrangements, the endovascular system also includes a fillable bag (e.g., endobag) 710 that is fillable by a fill line (not shown). The fillable bag 710 can be attached, connected, or otherwise fixed to the exterior of the first tubular graft body 700. The fillable bag 710 can be filled with a fill medium to achieve an inflated or filled state. The fill medium can push a wall of the fillable bag 710 against the aorta wall. A portion of the fillable bag 710 extends into a space of the aorta 10 adjacent to the first tubular graft body 700. That is, when in an uninflated state, the fillable bag 710 can be confined to being around the first tubular graft body 700, but when inflated (in the filled state) as shown, the fillable bag 710 expands radially to fill a surrounding space, including at least a portion of a space (e.g., in the descending aorta portion 11) around the first tubular graft body 700 to which the second tubular graft body 701 does not extend. The fillable bag 710 when filled is configured to provide sealing for an end of the second tubular graft body 701 that is at the left subclavian artery 14.

In various arrangements, the endovascular system in FIG. 7A also includes a fillable bag (e.g., endobag) 711 attached, connected, or otherwise fixed to the exterior of the second tubular graft body 701 except at the location of the fenestration 702. The fillable bag 711 is fillable by a fill line (not shown). A cross-sectional view of the system of FIG. 7A in the ascending aorta portion 13 is shown in FIG. 7B. As shown in FIGS. 7A and 7B, the fillable bags 710 and 711, when filled, expand to fill the space in the ascending aorta portion 13 and the aortic arch portion 12. The fillable bags 710 and 711, when filled, push against one another in the ascending aorta portion 13 and the aortic arch portion 12, to structurally support the first tubular graft body 700 and the second tubular graft body 701 in the ascending aorta portion 13 and the aortic arch portion 12. As shown, the first tubular graft body 700 may have a larger cross-section (e.g., larger radius) than that of the second tubular graft body 701. The fillable bags 710 and 711 are configured to provide a seal in at least a proximal portion and/or an arch portion (e.g., the ascending aorta portion 13 and/or the aortic arch portion 12) of the main artery (e.g., the aorta 10). The fillable bag 710 is also configured to provide a seal in a distal portion (e.g., the descending aorta portion 11) of the main artery (e.g., the aorta 10).

A thoracic stent graft system in accordance with an arrangement such as in FIGS. 7A and 7B employs a parallel stent which in this arrangement has a portion covered with graft material in the ascending aorta portion 13 to potentially exclude an ascending aneurysm or otherwise diseased ascending aorta portion 13, such as a dissection, perforation, penetrating ulcer, or the like. In various arrangements, a section of the parallel stent graft of FIGS. 7A and 7B is in apposition to the aortic arch vessels which are then perfused via the graft-free or bare stent in the superior arch region. Alternatively, this component could be a stent where the covering includes a polymer endo bag or sealing rings on either or both ends. In various arrangements, the system of FIGS. 7A and 7B includes a stent graft that employs polymer to seal an endobag or rings in the aorta 10 and around the partially covered parallel stent, thus stabilizing and anchoring the stent graft system.

FIGS. 7C and 7D show an endovascular system in accordance with an arrangement. The endovascular system of FIGS. 7C and 7D is configured to be generally placed in a thoracic endoluminal space of a person's aorta 10. As shown in FIG. 7C, the endovascular system includes a main tubular graft body 700 that extends from the ascending aorta portion 13 to the aortic arch portion 12 and to the descending aorta portion 11. In various arrangements, the endovascular system further includes a molded channel 703 and a fillable bag (e.g., endobag) 710, fillable by a fill line (not shown). In various arrangements, the molded channel 703 extends from the ascending aorta portion 13 to the aortic arch portion 12 and has one or more openings or one or more open channels to allow for perfusion of the aortic arch vessels. The one or more openings or one or more open channels may face the aortic arch vessels (e.g., the innominate artery 20, the left common carotid artery 15, and the left subclavian artery 14) to allow for perfusion. A cross-sectional view of the system of FIG. 7C in the ascending aorta portion 13 is shown in FIG. 7D.

The molded channel 703 is closer to the greater arch vessels (e.g., the innominate artery 20, the left common carotid artery 15, and the left subclavian artery 14) than the first tubular graft body 700. The molded channel 703 (and the one or more openings or one or more open channels) is between the first tubular graft body 700 and the greater arch vessels. An end of the molded channel 703 is at a portion in the aorta wall that is next to an end of the left subclavian artery 14.

The fillable bag 710 can be attached, connected, or otherwise fixed to the exterior of the first tubular graft body 700. The fillable bag 710 can be filled with a fill medium to achieve an inflated or filled state. The fill medium can push a wall of the fillable bag 710 against the aorta wall. A portion of the fillable bag 710 extends into a space of the aorta 10 adjacent to the first tubular graft body 700. That is, when in an uninflated state, the fillable bag 710 can be confined to being around the first tubular graft body 700, but when inflated (in the filled state) as shown, the fillable bag 710 expands radially to fill a surrounding space, including at least a portion of a space (e.g., in the descending aorta portion 11) around the first tubular graft body 700 to which the molded channel 703 does not extend. The fillable bag 710 when filled is configured to provide sealing for an end of the molded channel 703 that is at the left subclavian artery 14.

As shown in FIGS. 7C and 7D, the fillable bag 710, when filled, expands to fill the space in the ascending aorta portion 13 and the aortic arch portion 12, around both the first tubular graft body 700 and the molded channel 703. The fillable bag 710, when filled, pushes against the molded channel 703 the ascending aorta portion 13 and the aortic arch portion 12, to structurally support the first tubular graft body 700 and the molded channel 703 in the ascending aorta portion 13 and the aortic arch portion 12. In particular, the fillable bag 710 maintains the orientation of the molded channel 703, to support the one or more openings or one or more open channels of the molded channel 703 to face the greater arch vessels. In some examples, the fillable bag 710 is attached, connected, or otherwise fixed to an exterior surface of the molded channel 703 that is opposite to the one or more openings or one or more open channels of the molded channel 703. In particular, the fillable bag 710 is configured to provide a seal in at least a proximal portion and/or arch portion (e.g., the ascending aorta portion 13 and/or the aortic arch portion 12) of the main artery (e.g., the aorta 10). The fillable bag 710 is also configured to provide a seal in a distal portion (e.g., the descending aorta portion 11) of the main artery (e.g., the aorta 10). As shown, the first tubular graft body 700 may have a larger cross-section than that of the molded channel 703.

A thoracic stent graft system in accordance with an arrangement such as in FIGS. 7C and 7D includes a component that has been molded in situ with a balloon to create a channel (e.g., the molded channel 703) allowing antegrade perfusion to the arch vessels. In some other arrangements, the molded channel 703 is implemented with a retrograde flow channel since the balloon may be easier to retract from standard femoral artery access. In various arrangements, the procedural steps for deploying the system in FIGS. 7C and 7D include: (1) position a balloon to create space using a compliant or a non-compliant balloon; (2) position a polymer based stent graft system into the ascending aorta portion 13; (3) inject polymer into the balloon to seal and create an aortic branch vessel channel; and (4) upon completion of polymer cure, deflate the space creating device (i.e., balloon), re-sheath (if necessary), and remove from vasculature.

Instead of or in addition to a fillable bag 710, in some arrangements the first tubular graft body 700 or the second tubular graft body 701 in FIGS. 7A and 7B include inflatable channels disclosed herein that are disposed along the first tubular graft body 700 and/or the second tubular graft body 701. In some arrangements, one or more of the first tubular graft body 700 and the second tubular graft body 701 have a wire wound stent.

Figure 8A:
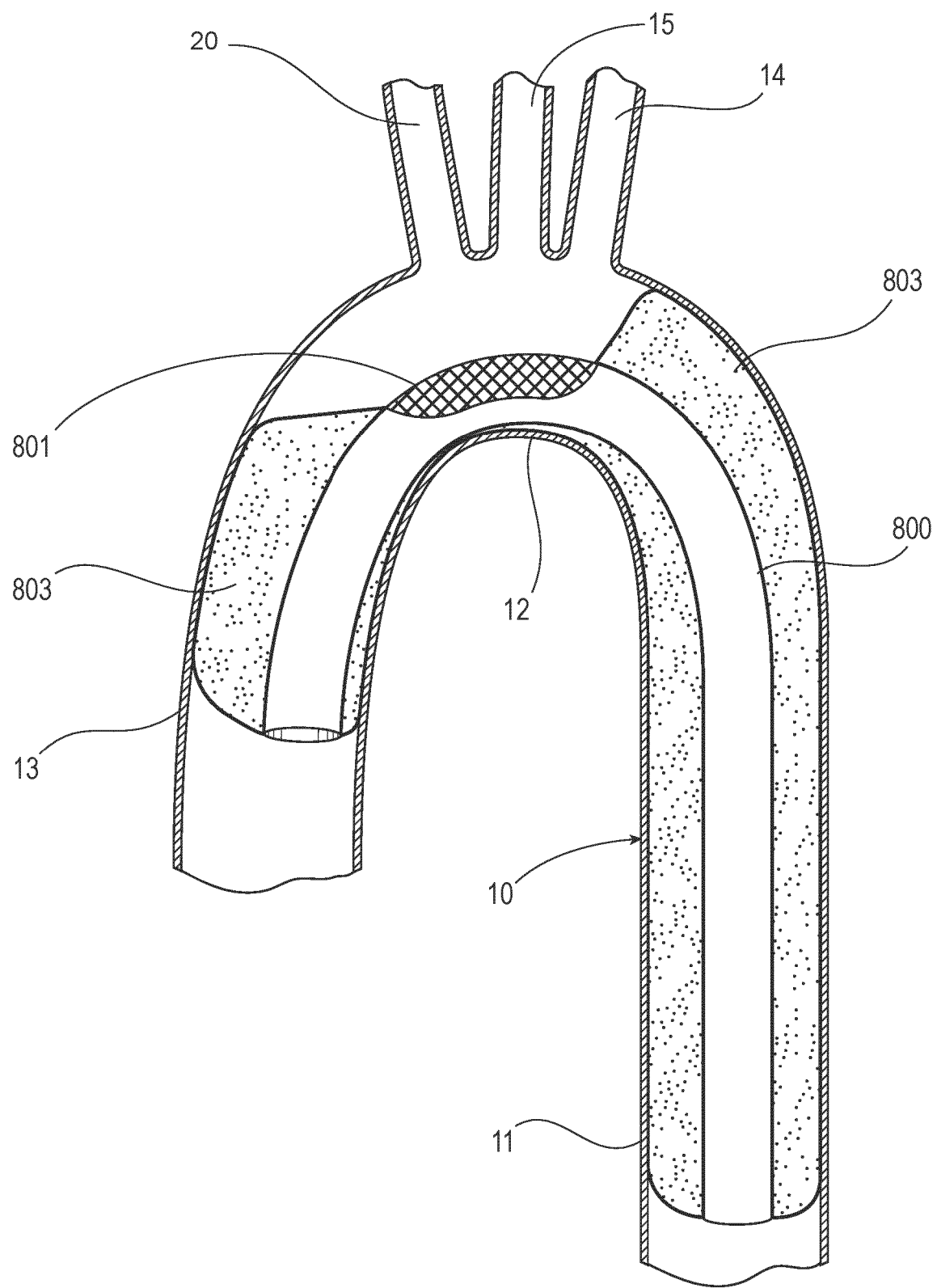
FIG. 8A shows an endovascular system in accordance with an arrangement deployed in an aortic arch.

FIG. 8A shows an endovascular system in accordance with an arrangement. The endovascular system of FIG. 8A includes a main tubular graft body 800 having a fenestration with an open stent structure 801 that is configured to be in fluid connection with at least one of the greater arch vessels (e.g., the innominate artery 20, the left common carotid artery 15, and the left subclavian artery 14). The open fenestration with the open stent structure 801 is configured to allow for perfusion of the greater arch vessels. The fenestration with an open stent structure 801 is configured to face the aortic arch vessels (e.g., the innominate artery 20, the left common carotid artery 15, and the left subclavian artery 14) to allow for perfusion. The fenestration with an open stent structure 801 is spaced apart from the openings of the aortic arch vessels. In some arrangements, such as in FIG. 8A, the fenestration with the open stent structure 801 extends only partially around a circumference of the main tubular graft body 800, and not the entire circumference of the tubular graft body 800.

The endovascular system of FIG. 8A also includes one or more fillable bags 803 with an open section surrounding the fenestration with the stent structure 801 of the main tubular graft body 800. In some arrangements, there is a single polymer fill tube connected to the one or more fillable bags 803. In some arrangements, there are two or more polymer fill tubes connected to the one or more fillable bags 803. For example, in some arrangements, one polymer fill tube is connected to one of the fillable bags 803 or a portion thereof at a proximal end of the main tubular graft body 800 (e.g., in the ascending aorta portion 13) and another polymer fill tube is connected to one of the fillable bags 803 or a portion thereof at a distal end of the main tubular graft body 800 (e.g., in the descending aorta portion 11). In some arrangements, there is a single fillable bag 803 that extends from the ascending aorta portion 13 over the aortic arch portion 12 and from the aortic arch portion 12 to the descending aorta portion 11. The one or more fillable bags 803 can be attached, connected, or otherwise fixed to the exterior of the tubular graft body 800. The one or more fillable bags 803 can be filled with a fill medium to achieve an inflated or filled state. The fill medium can push a wall of the one or more fillable bags 803 against the aorta wall. When in an uninflated state, the one or more fillable bags 803 can be confined to being around the tubular graft body 800, but when inflated (in the filled state) as shown, the one or more fillable bags 803 expand radially to fill a surrounding space, including at least a portion of a space (e.g., in the descending aorta portion 11 and in the ascending aorta portion 13) around the tubular graft body 800. The one or more fillable bags 803, when filled, push against the aorta wall at the ascending aorta portion 13 and the descending aorta portion 11, to structurally support the tubular graft body 800. In particular, the one or more fillable bags 803 maintain the orientation of the tubular graft body 800, to support the fenestration with the open stent structure 801 to face the greater arch vessels because the fenestration with the open stent structure 801 does not extend to the entire circumference of the tubular graft body 800. In some arrangements, the one or more fillable bags 803 are configured to provide a seal in at least a proximal portion and/or arch portion (e.g., the ascending aorta portion 13 and/or the aortic arch portion 12) of the main artery (e.g., the aorta 10). In some arrangements, the one or more fillable bags 803 are also configured to provide a seal in a distal portion (e.g., the descending aorta portion 11) of the main artery (e.g., the aorta 10). The one or more fillable bags 803 and the fenestration with the open stent structure 801 define a space/volume near the aortic arch vessels, where the blood can flow in the space/volume.

Figure 8B:
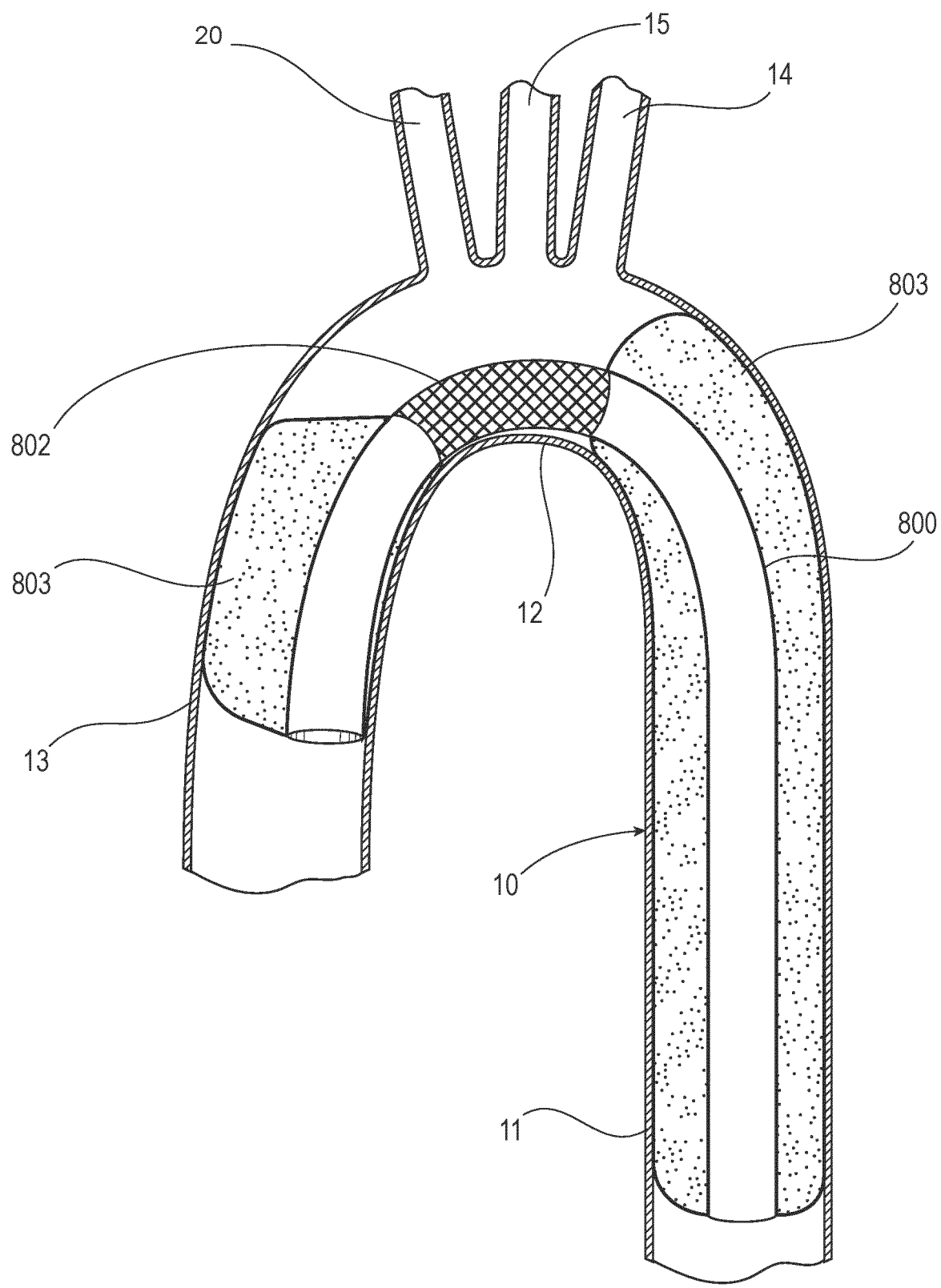
FIG. 8B shows an endovascular system in accordance with an arrangement deployed in an aortic arch.

FIG. 8B shows an endovascular system in accordance with an arrangement. The endovascular system of FIG. 8B includes a main tubular graft body 800 having a fenestration with an open stent structure 802 configured to be in fluid connection with at least one of the greater arch vessels (e.g., the innominate artery 20, the left common carotid artery 15, and the left subclavian artery 14). The open stent structure 802 is configured to allow perfusion of the greater arch vessels. In various arrangements, the open stent structure 802 extends around an entire circumference of the main tubular graft body 800 in a location that is positionable in the aortic arch. The fenestration with the open stent structure 802 is configured to be disposed in the aorta 10 (e.g., in the aortic arch portion 12) to be near or face the aortic arch vessels (e.g., the innominate artery 20, the left common carotid artery 15, and the left subclavian artery 14) to allow for the perfusion. In some arrangements, the fenestration with the open stent structure 802 is spaced apart from the openings of the aortic arch vessels.

In various arrangements, the endovascular system also includes two or more fillable bags 803. In some arrangements, a first fillable bag of the two or more fillable bags 803 is configured to be deployed at the distal end of the main tubular graft body 800 (e.g., in the descending aorta portion 11), and a second fillable bag of the two or more fillable bags 803 is configured to be deployed at the proximal end of the main tubular graft body 800 (e.g., in the ascending aorta portion 13). In some arrangements, the first fillable bag of the two or more fillable bags 803 and the second fillable bag of the two or more fillable bags 803 are separate bags that are independently filled by two different fill lines (not shown). The fillable bags 803 can be filled with a fill medium to achieve an inflated or filled state. The fill medium can push a wall of the fillable bags 803 against the aorta wall. When in an uninflated state, the fillable bags 803 can be confined to being around the tubular graft body 800, but when inflated (in the filled state) as shown, the fillable bags 803 expands radially to fill a surrounding space, including at least a portion of a space (e.g., in the descending aorta portion 11) and another portion of a space (e.g., in the ascending aorta portion 13) around the tubular graft body 800. The fillable bags 803, when filled, push against the aorta wall at the ascending aorta portion 13 and the descending aorta portion 11, to structurally support the tubular graft body 800. In particular, the fillable bags 803 maintain the position of the tubular graft body 800, to support the fenestration with the open stent structure 802 to be near or face the greater arch vessels. In particular, the fillable bags 803 are configured to provide a seal in at least a proximal portion (e.g., the ascending aorta portion 13) of the main artery (e.g., the aorta 10). The fillable bags 803 are also configured to provide a seal in a distal portion (e.g., the descending aorta portion 11) of the main artery (e.g., the aorta 10). In some arrangements, the fillable bags 803 and the fenestration with the open stent structure 802 define a space/volume near the aortic arch vessels, where the blood can flow in the space/volume.

A thoracic stent graft (e.g., the tubular graft body 800) in accordance with various arrangements such as in FIGS. 8A and 8B is generally tubular in nature and includes wire wound or laser cut stents of suitable material which may be self-expanding, such as nitinol, or may be balloon expandable, such as 316L Stainless Steel or L605 cobalt chromium, and may be generally encapsulated in PTFE graft material, partially encapsulated in PTFE graft material, or bare. In various arrangements, the stent graft of FIG. 8A or 8B has an open stent structure in the region of the aortic arch vessels which are then perfused via the graft free open fenestration in the ascending and arch region. In various arrangements, polymer is employed to seal in areas proximal and distal to the graft free open stent structure, therefore stabilizing and anchoring the stent graft system. In some arrangements, active fixation may be incorporated into the stent if needed.

Figure 9A:
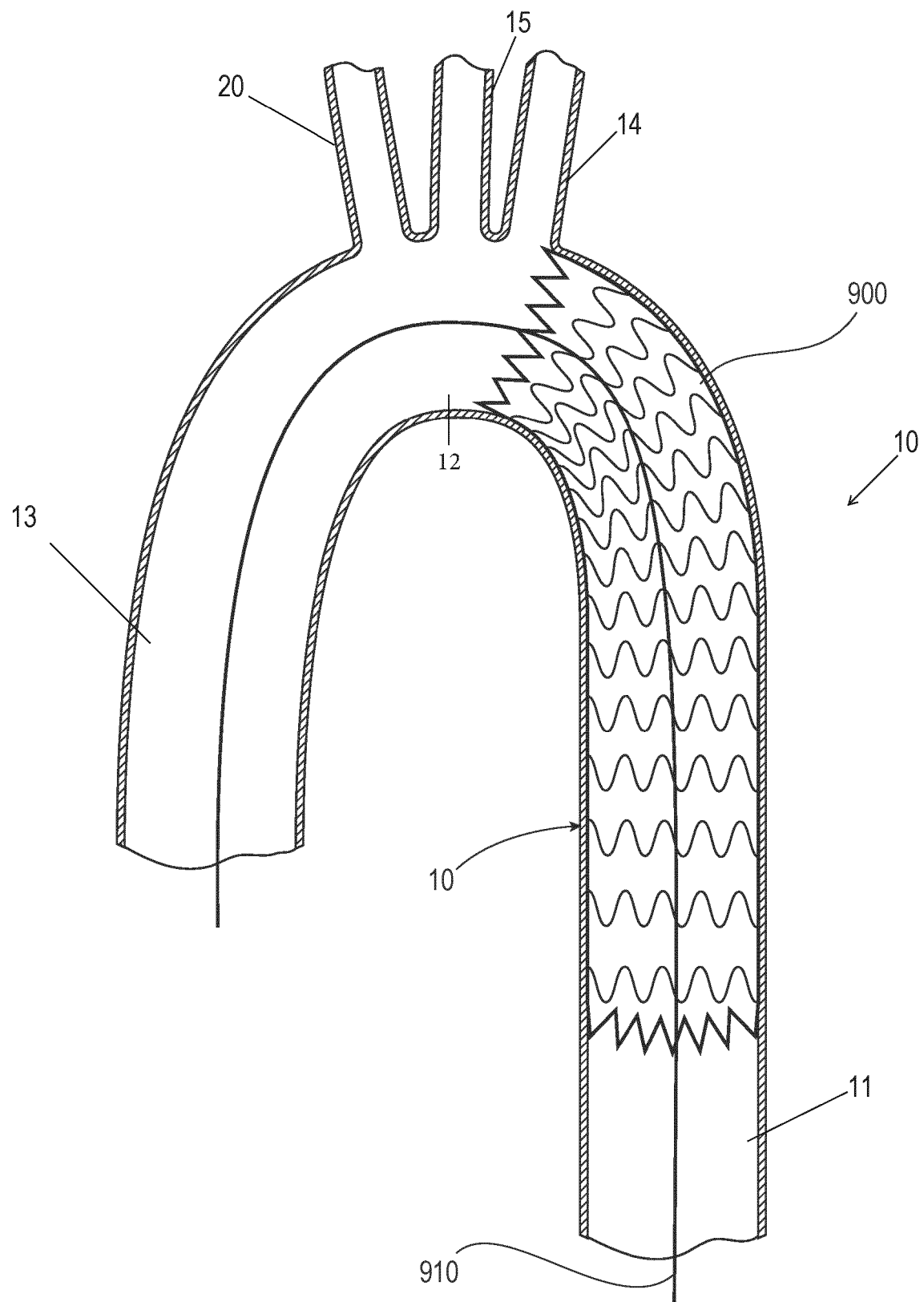
FIG. 9A shows an endovascular system in accordance with an arrangement deployed in an aortic arch.

FIGS. 9A, 9B, 9C, 9D, and 9E illustrate a method for sequential deployment of a system for retrograde branched flow in accordance with an arrangement. As shown in FIG. 9A, a descending graft body 900 is deployed first in the descending aorta portion 11 using a wire 910. The wire 910 extends through the aorta 10, and passes the descending aorta portion 11 and the aortic arch portion 12 into the ascending aorta portion 13. The descending graft body 900 extends from the descending aorta portion 11 to and before the left subclavian artery 14. The descending graft body 900 includes a suitable stent structure, walls, and anchoring members.

Figure 9B:
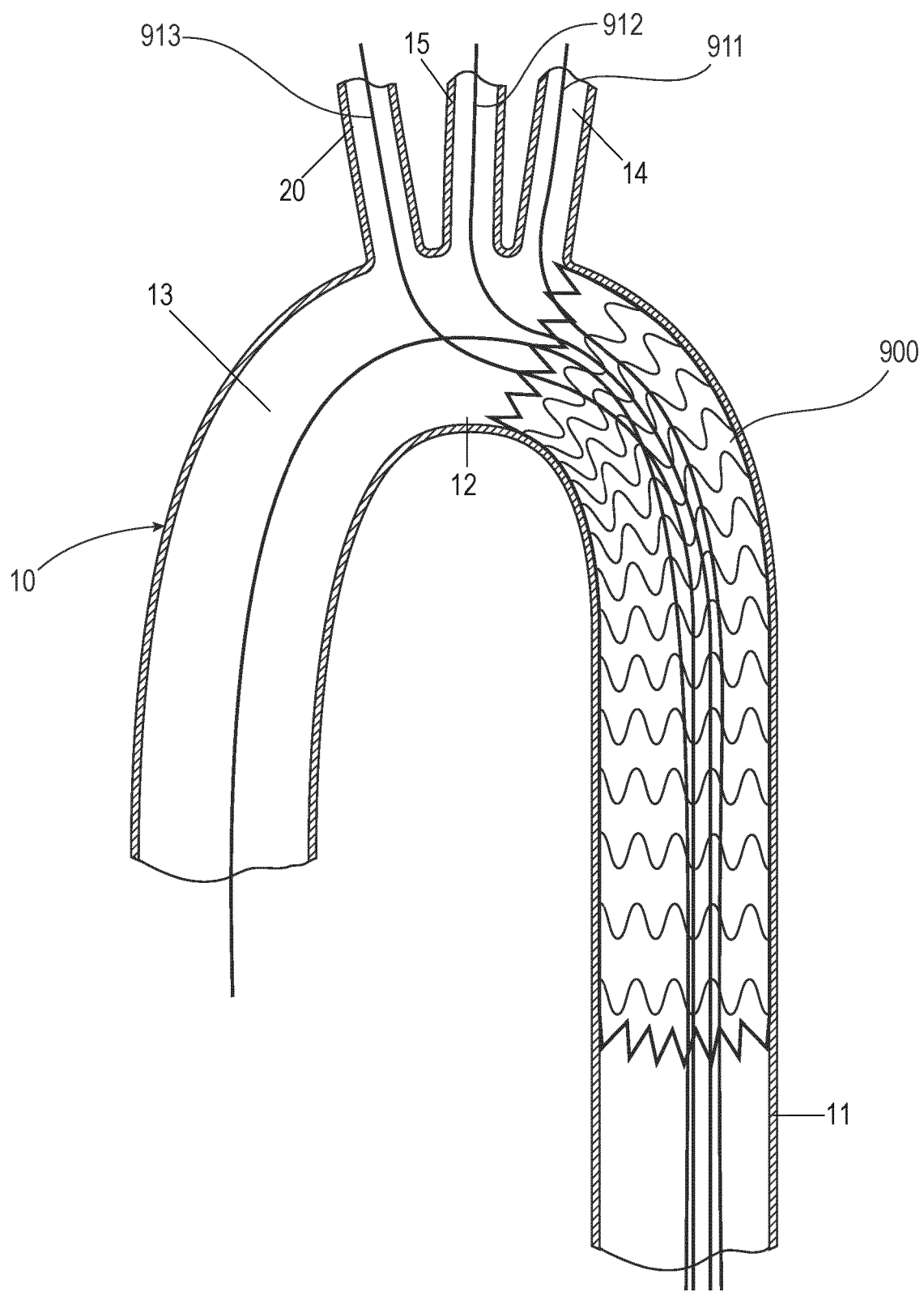
FIG. 9B shows an endovascular system in accordance with an arrangement deployed in an aortic arch.

FIG. 9B shows gaining access of the greater arch vessels (e.g., the innominate artery 20, the left common carotid artery 15, and the left subclavian artery 14) via deployment of wires 911, 912 and 913. After the descending graft body 900 is deployed, the wires 911, 912 and 913 are deployed in the left subclavian artery 14, the left common carotid artery 15, and the innominate artery 20, respectively, in any suitable order. In particular, the wires 911, 912 and 913 are shown to extend from the descending aorta portion 11 to the aortic arch portion 12, and then through the left subclavian artery 14, the left common carotid artery 15, and the innominate artery 20, respectively.

Figure 9C:
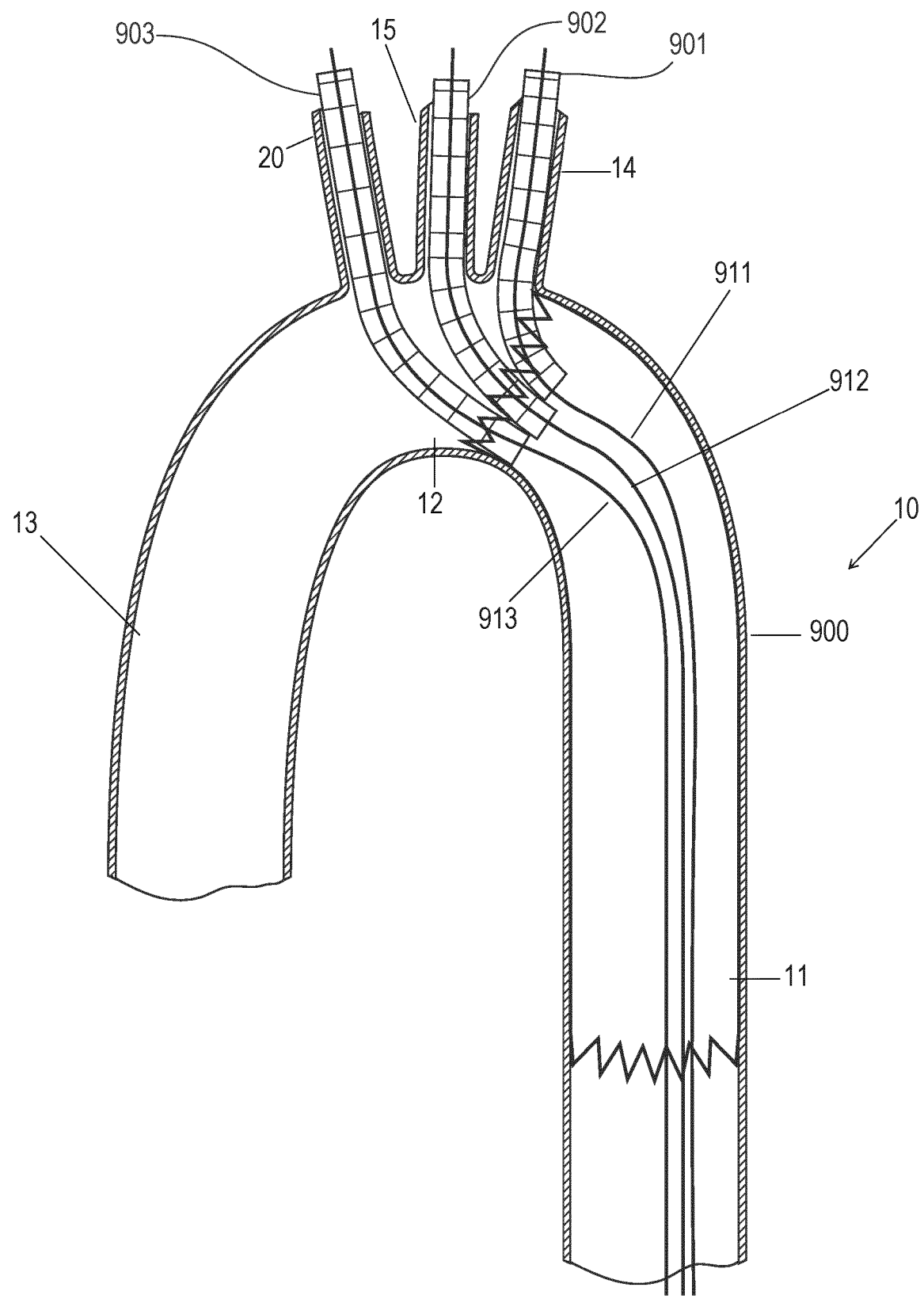
FIG. 9C shows an endovascular system in accordance with an arrangement deployed in an aortic arch.

FIG. 9C shows deployment of branch tubular graft bodies 901, 902, and 903 to at least one aortic arch branch vessel while maintaining access. The stent structure of the descending graft body 900 and the wire 910 are not shown for clarity. After the wires 911, 912 and 913 are deployed, the branch tubular graft bodies 901, 902, and 903 are deployed using the wires 911, 912 and 913 to a respective one of the left subclavian artery 14, the left common carotid artery 15, and the innominate artery 20. For example, the branch tubular graft body 901 is configured to move as guided by the wire 911, to the aortic arch portion 12 and the left subclavian artery 14. The branch tubular graft body 902 is configured to move as guided by the wire 912, to the aortic arch portion 12 and the left common carotid artery 15. The branch tubular graft body 903 is configured to move as guided by the wire 913, to the aortic arch portion 12 and the innominate artery 20. At least a portion (e.g., an end) of each of the branch tubular graft bodies 901, 902, and 903 overlaps or is within an interior volume defined by the descending graft body 900.

FIG. 9D shows deployment of an ascending aortic tubular component 914 with inflatable channels such as but not limited to, polymer rings or fillable bags to seal around the parallel branch graft bodies (e.g., the branch tubular graft bodies 901, 902, and 903) and around the ascending aortic tubular component 914. After the branch tubular graft bodies 901, 902, and 903 are deployed, the wires 911, 912 and 913 may be retracted. The ascending aortic tubular component 914 can be deployed. In some examples, the ascending aortic tubular component 914 can be deployed using the wire 910 (refer to FIG. 9A), and after the ascending aortic tubular component 914 is deployed, the wire 910 may be retrieved. With reference to FIG. 9D, at least a portion (e.g., an end) of the ascending aortic tubular component 914 overlaps or is within the interior volume defined by the descending graft body 900. The ascending aortic tubular component 914 extends from the descending graft body 900 through the aortic arch portion 12 to the ascending aorta portion 13.

In various arrangements, a fillable bag 915 is used to fill a space around the grafts (e.g., the branch tubular graft bodies 901, 902, and 903 and the ascending aortic tubular component 914) within the aorta 10, for example, in the aortic arch portion 12 to the ascending aorta portion 13. The fillable bag 915 can be attached, connected, or otherwise fixed to the exterior of the ascending aortic tubular component 914. The fillable bag 915 can be filled with a fill medium to achieve an inflated or filled state. The fill medium can push a wall of the fillable bag 915 against the aorta wall. The fillable bag 915 extends into a space of the aorta 10 adjacent to the ascending aortic tubular component 914. That is, when in an uninflated state, the fillable bag 915 can be confined to being around the ascending aortic tubular component 914, but when inflated (in the filled state) as shown, the fillable bag 915 expands radially to fill a surrounding space, including the aortic arch portion 12 to the ascending aorta portion 13. In that regard, the fillable bag 915 when filled is configured to provide sealing for spaces in the aortic arch portion 12 to the ascending aorta portion 13 not occupied by the branch tubular graft bodies 901, 902, and 903 and the ascending aortic tubular component 914.

As shown in FIG. 9E, in various arrangements, ends of the branch tubular graft bodies 901, 902, and 903, and an end of the ascending aortic tubular component 914 are positioned in the descending graft body 900, and the space around the branch tubular graft bodies 901, 902, and 903, and the ascending aortic tubular component 914 is filled by the fillable bag 915.

Various arrangements, such as in FIGS. 9A, 9B, 9C, 9D, and 9E, provide for a sequential deployment sequence for retrograde branched flow. In various arrangements, initially, a descending thoracic stent graft (e.g., the descending graft body 900), which is generally tubular in nature and could be comprised of wire wound or laser cut nitinol stents generally encapsulated in PTFE graft material, is deployed. In various arrangements, wire access of the greater arch vessels 14, 15, 20 is gained individually, where the three wires 911, 912 and 913 would be needed for standard anatomy or two wires for a bovine arch. In some arrangements, bare stents or alternatively stent grafts (e.g., the branch tubular graft bodies 901, 902, and 903) are deployed into each of the greater arch vessels 14, 15, 20 with the distal ends of the stents being co-located in the same axial position within the thoracic aorta. In various arrangements, with the guide wire (e.g., the wire 910) in place and the arch stents deployed, the final modular ascending/arch component (e.g., the ascending aortic tubular component 914) that is comprised of a stent and graft material, and that may incorporate polymer, is positioned and deployed with axial overlap with respect to the aortic branch vessel stents (e.g., the branch tubular graft bodies 901, 902, and 903). In some arrangements, polymer rings or a bag (e.g., the fillable bag 915) are optimally filled to seal any resultant gutters from the parallel stents 901, 902, 903, and 914. In some other arrangements, the resultant modular system relies on ante-grade flow through the ascending/arch component directly from the heart. In some arrangements, the aortic arch vessels are perfused via retrograde flow after exiting the ascending/arch component.

Figure 10A:
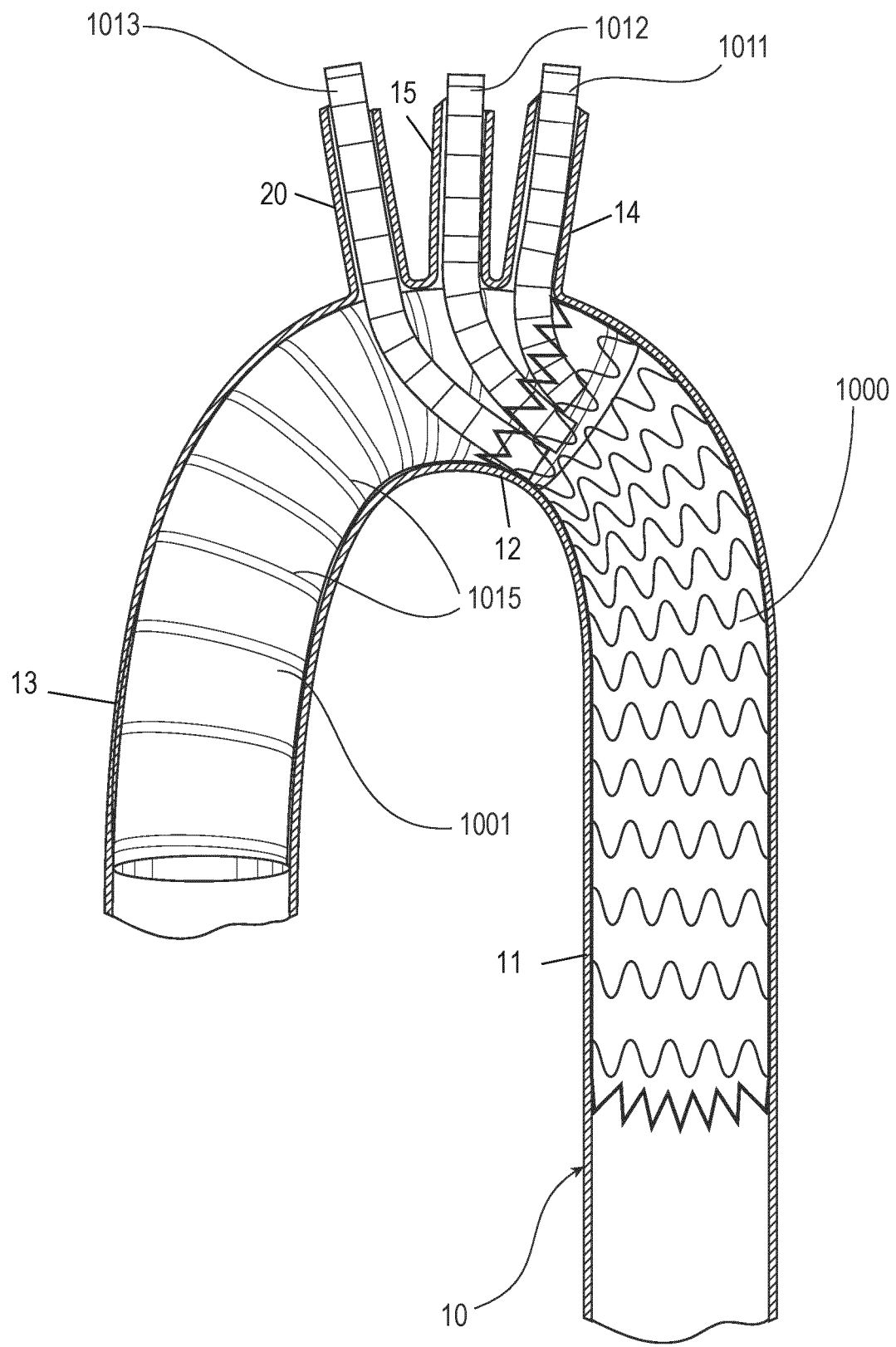
FIG. 10A shows an endovascular system in accordance with an arrangement deployed in an aortic arch.

FIG. 10A shows an endovascular system in accordance with an arrangement. The endovascular system of FIG. 10A includes a first tubular graft body 1000 configured to form the distal end of the endovascular system. The first tubular graft body 1000 includes a suitable stent structure, walls, and anchoring members. The first tubular graft body 1000 is configured to extend from the descending aorta portion 11 to and before the left subclavian artery 14.

The system also includes a second tubular graft body 1001 having a plurality of inflatable channels 1015 and further configured to be in fluid connection with the first tubular graft body 1000. The second tubular graft body 1001 is configured to form the proximal end of the system. At least a portion (e.g., an end) of second tubular graft body 1001 overlaps or is within an interior volume defined by the first tubular graft body 1000. In various arrangements, the second tubular graft body 1001 extends from the ascending aorta portion 13 into the first tubular graft body 1000 at the aortic arch portion 12. The plurality of inflatable channels 1015 may be similar to the inflatable channels 106 described with respect to FIGS. 1, 2, 3, 4, and 5.

The system of FIG. 10A also includes branch tubular graft bodies 1011, 1012, and 1013 configured to be deployed in at least one branch vessel (e.g., a respective one of the left subclavian artery 14, the left common carotid artery 15, and the innominate artery 20). The branch tubular graft bodies 1011, 1012, and 1013 are configured to be in fluid connection with the first tubular graft body 1000. For example, the branch tubular graft body 1011 is configured to be disposed in the aortic arch portion 12 and the left subclavian artery 14. The branch tubular graft body 1012 is configured to be disposed in the aortic arch portion 12 and the left common carotid artery 15. The branch tubular graft body 1013 is configured to be disposed in the aortic arch portion 12 and the innominate artery 20. At least a portion (e.g., an end) of each of the branch tubular graft bodies 1011, 1012, and 1013 overlaps or is within an interior volume defined by the first tubular graft body 1000.

FIG. 10B shows an endovascular system in accordance with an arrangement. FIGS. 10C and 10D show cross-sectional views of different parts of the endovascular system of FIG. 10B. The endovascular system of FIG. 10B includes a main tubular graft body 1000. The main tubular graft body 1000 includes a suitable stent structure, walls, and anchoring members. The main tubular graft body 1000 is configured to extend from the descending aorta portion 11 to and before the left subclavian artery 14.

A mesh stent 1002 extends from a proximal end of the main tubular graft body 1000. The mesh stent 1002 is fixed, attached, or otherwise connected to the main tubular graft body 1000. The mesh stent 1002 is in fluid communication with the main tubular graft body 1000. At least a portion (e.g., an end) of mesh stent 1002 overlaps or is within an interior volume defined by the main tubular graft body 1000. In various arrangements, the mesh stent 1002 extends from the ascending aorta portion 13 into the first tubular graft body 1000 at the aortic arch portion 12.

The arrangement of FIG. 10B further includes branch tubular graft bodies 1011, 1012, and 1013 configured to be deployed in at least one branch vessel (e.g., a respective one of the left subclavian artery 14, the left common carotid artery 15, and the innominate artery 20). For example, the branch tubular graft body 1011 is configured to be disposed in the aortic arch portion 12 and the left subclavian artery 14. The branch tubular graft body 1012 is configured to be disposed in the aortic arch portion 12 and the left common carotid artery 15. In various arrangements, the branch tubular bodies 1011 and 1012 are configured to be in fluid connection with the main tubular graft body 1000. At least a portion (e.g., an end) of each of the branch tubular graft bodies 1011 and 1012 overlaps or is within an interior volume defined by the main tubular graft body 1000. The branch tubular graft body 1013 is configured to be disposed in the aortic arch portion 12, the ascending aorta portion 13, and the innominate artery 20.

The system further includes a fillable bag 1003 for sealing spaces around the grafts and stent (e.g., the branch tubular graft bodies 1011, 1012, and 1013 and the mesh stent 1002) within the aorta 10, for example, in the aortic arch portion 12 to the ascending aorta portion 13. The fillable bag 1003 can be attached, connected, or otherwise fixed to the exterior of the mesh stent 1002. The fillable bag 1003 can be filled with a fill medium to achieve an inflated or filled state. The fill medium can push a wall of the fillable bag 1003 against the aorta wall. The fillable bag 1003 extends into a space of the aorta 10 adjacent to the mesh stent 1002. That is, when in an uninflated state, the fillable bag 1003 can be confined to being around the mesh stent 1002, but when inflated (in the filled state) as shown, the fillable bag 1003 expands radially to fill a surrounding space, including a portion of the aortic arch portion 12 to the ascending aorta portion 13. In that regard, the fillable bag 1003 when filled is configured to provide sealing for spaces in the aortic arch portion 12 to the ascending aorta portion 13 not occupied by the branch tubular graft bodies 1011, 1012, and 1013 and the mesh stent 1002.

FIG. 10C shows a cross section of the endovascular system of FIG. 10B at the proximal end of the endovascular system (e.g., in the ascending aorta portion 13). For example, FIG. 10C shows a cross-section with the mesh stent 1002 and the branch tubular graft body 1013, and the fillable bag 1003 around the mesh stent 1002 and the branch tubular graft body 1013.

FIG. 10D shows a cross section of the endovascular system of FIG. 10B where the main tubular graft body 1000 connects to the mesh stent 1002 and the branch tubular graft bodies 1011 and 1012 (e.g., in the aortic arch portion 12 at or near the greater arch vessels 14, 15, 20). For example, FIG. 10D shows a cross-section with the mesh stent 1002 and the branch tubular graft bodies 1011 and 1012, and the fillable bag 1003 around the mesh stent 1002 and the branch tubular graft bodes 1011 and 1012.

Various arrangements provide for an annular polymer ringed device and allow for an innominate artery to be perfused in an antegrade fashion. Various arrangements include an annular polymer ringed device in the ascending aorta portion 13 and aortic arch portion 12 with retrograde aortic arch branch vessels being perfused in a retrograde fashion. In various arrangements, such as the arrangement of FIG. 10B, the innominate artery 20 is perfused in an antegrade fashion while the left common carotid and left subclavian arteries 15 and 14 are perfused in a retrograde fashion.

Figures 11A, 11B:
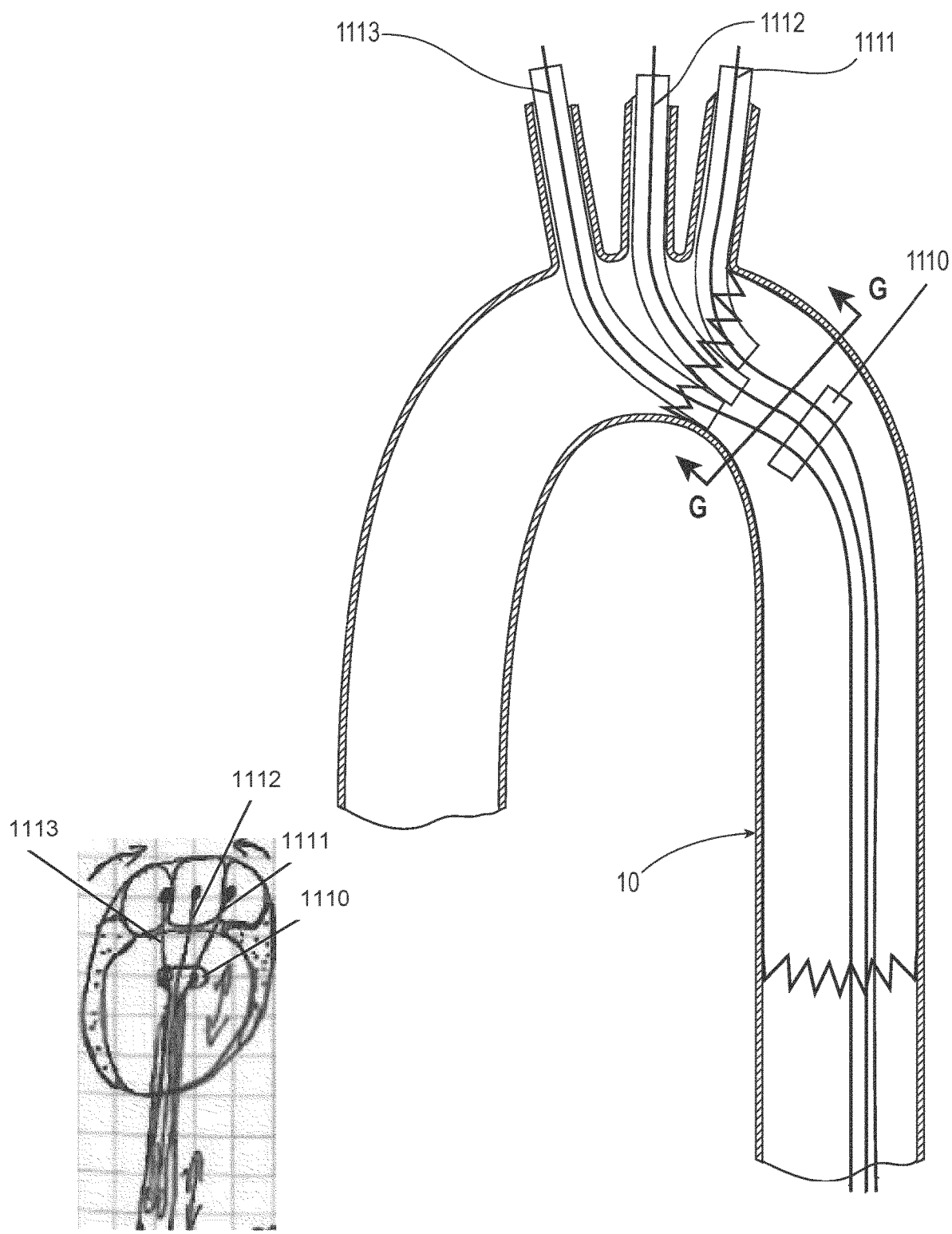
FIG. 11A shows accessories for deployment efficiency of an endovascular system in an aortic arch in accordance with an arrangement.
FIG. 11B shows a view of the accessories of FIG. 11A.
Figure 11C:
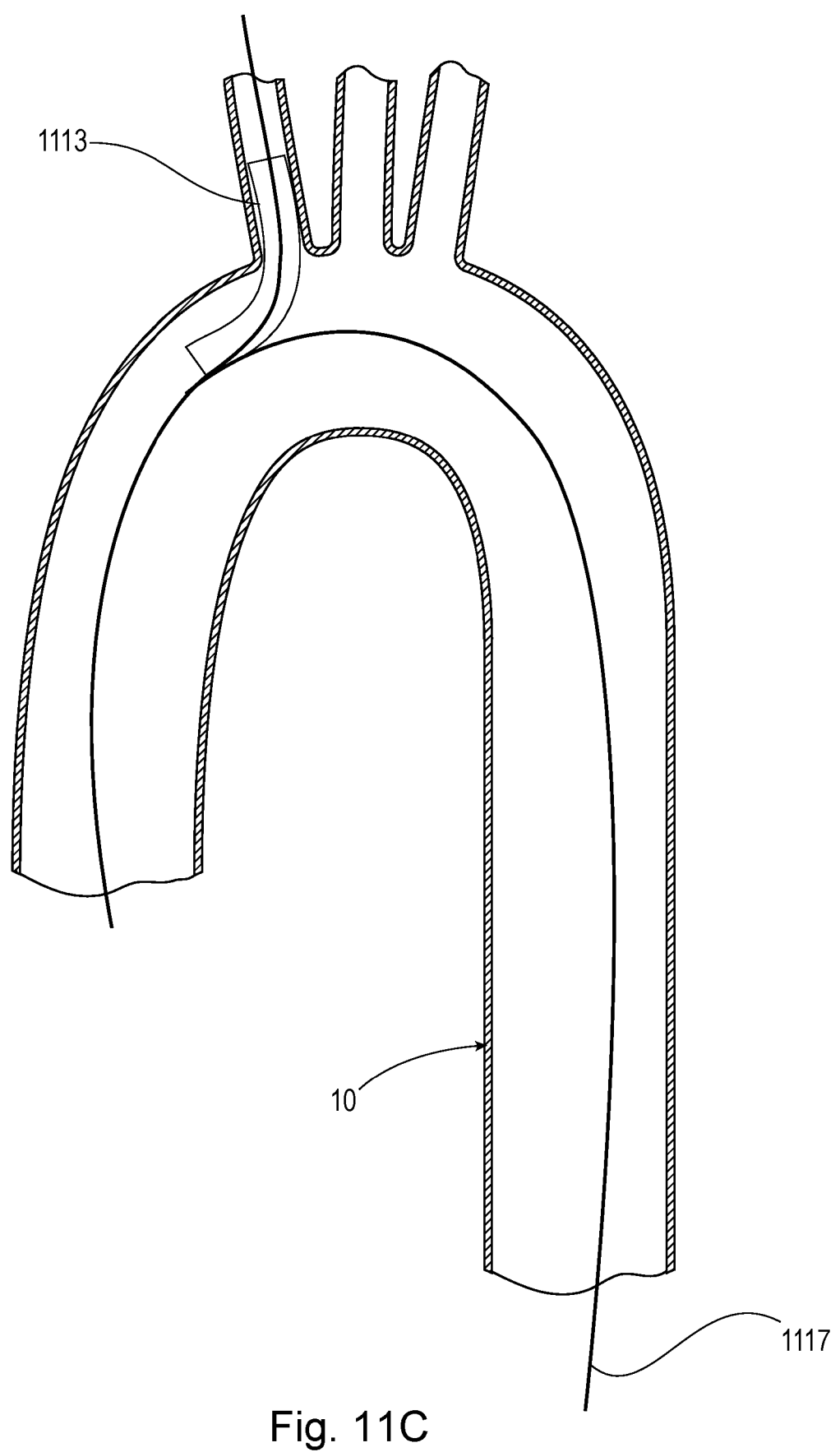
FIG. 11C shows accessories for deployment efficiency of an endovascular system in an aortic arch in accordance with an arrangement.

FIGS. 11A, 11B, and 11C show additional accessories for deployment of endovascular systems in accordance with various arrangements. With reference to FIGS. 11A and 11B, in various arrangements a wire holding device 1110 is deployed in an aorta 10 and is configured to hold and keep wires 1111, 1112, and 1113 close together during sealing or curing process. The wire holding device 1110 has one or more holes and each of the wires 1111, 1112, 1113 passes through a corresponding hole in the wire holding device 1110. In some arrangements, all of the wires 1111, 1112, and 1113 pass through a same hole in the wire holding device 1110. In some arrangements, each of the wires 1111, 1112, and 1113 pass through their own corresponding hole in the wire holding device 1110. In various arrangements, the wire holding device 1110 is configured to be positioned within the descending aorta or in the aortic arch and each of the wires 1111, 1112, and 1113 passes through the wire holding device 1110 to a corresponding aortic arch vessel. In various arrangements, the wire holding device 1110 is slidable to adjust wire nesting and make endografts flush. FIG. 11C shows an arrangement in which wires 1117 and 1113 are deployed to make it possible to perform retrograde cannulation and deployment for ascending aorta. This configuration for deployment is also useful for hypogastric access. In various arrangements, a retrograde deployment access technique allows for antegrade flow of one or more aortic arch vessels.

Various arrangements include accessories for deployment efficiency. A slidable component, such as the wire holding device 1110 in FIGS. 11A and 11B in accordance with various arrangements is used as an aid in minimizing gutters and keeping the proximal ends of parallel stents flush with each other. In various arrangements, the slidable component is configured to pull the wires of arch devices together during a polymer fill stage. In some arrangements, the slidable component is a slidable multi-lumen that accommodates all of the wires from the arch devices.

In some arrangements, a tubular graft body comprises a graft material and further includes annular rings. In some arrangements, a tubular graft body comprises one or more laser cut stents. In some arrangements, a tubular graft body is formed of a material having a property of self-expandability. In some arrangements, a tubular graft body comprises a material having a property of balloon expandability. In various arrangements, a tubular graft body includes a stent formed of Nitinol. In various arrangements, radiopaque markers are placed on a tubular graft body and/or other components of an endovascular system to assist in positioning the components.

Various arrangements provide for thoracic arch branch graft systems. Some arrangements have a "life jacket" or "window" design. Some arrangements provide for a retrograde patch.

Figure 12A:
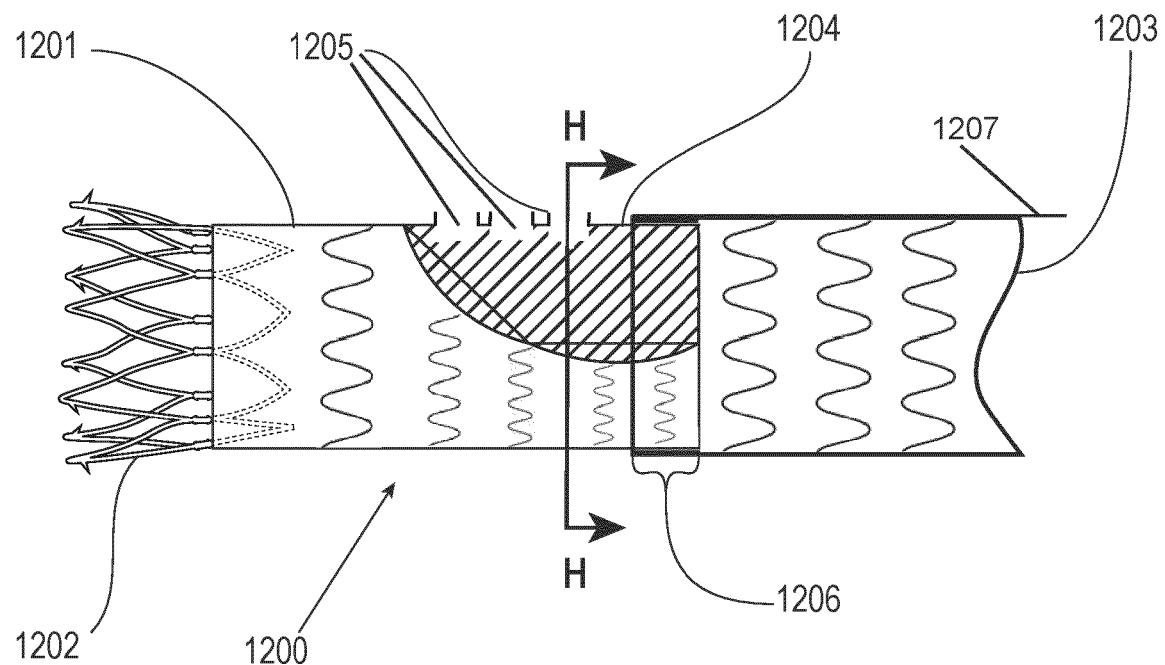
FIG. 12A shows an endovascular system in accordance with an arrangement.
Figure 12B:
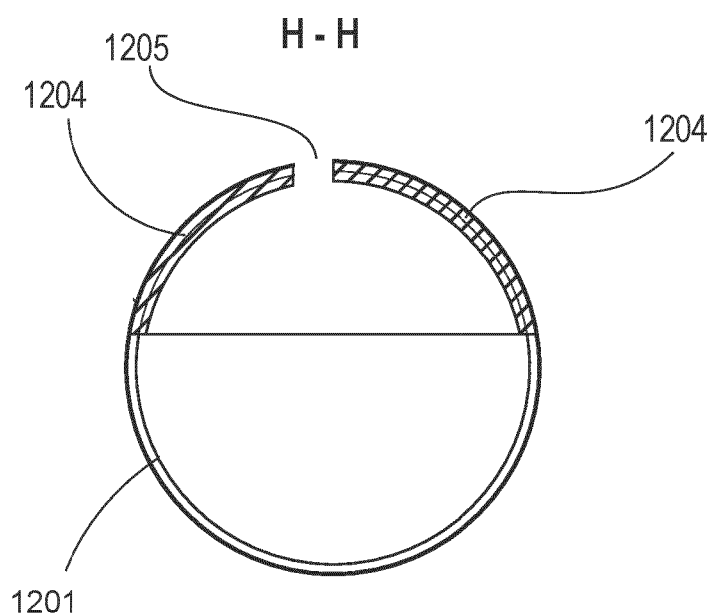
FIG. 12B is a cross-sectional view of a section of FIG. 12A.
Figure 12C:
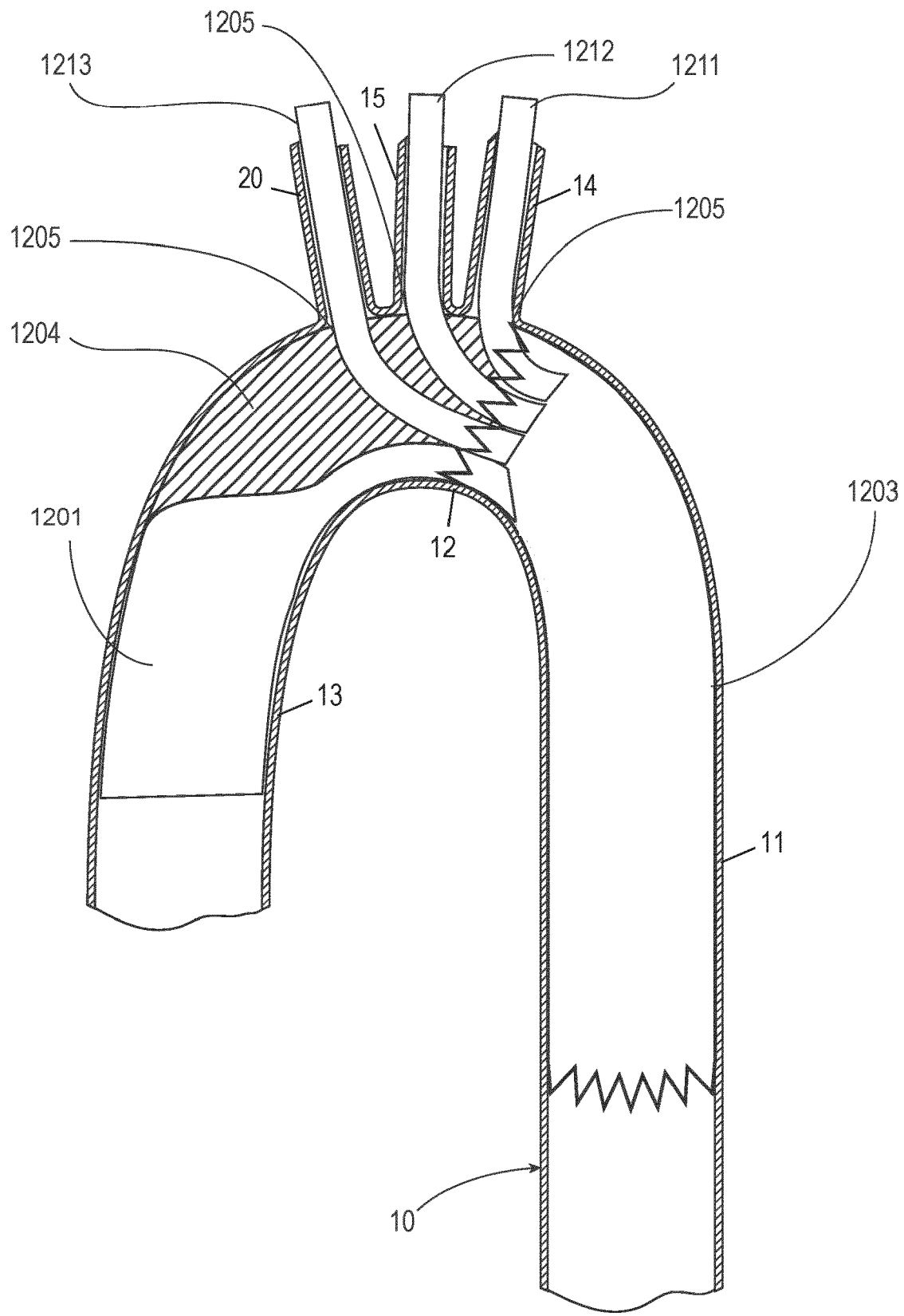
FIG. 12C shows an endovascular system in accordance with an arrangement deployed in an aortic arch.

FIGS. 12A, 12B, and 12C show an endovascular system in accordance with an arrangement. The endovascular system of FIGS. 12A, 12B, and 12C includes a main tubular graft body 1200 which includes a distal stent graft segment 1203 connected to and in fluid connection with a proximal stent graft segment 1201. The proximal stent graft segment 1201 and the distal stent graft segment 1203 have suitable stent structures and walls. The endovascular system of FIGS. 12A, 12B, and 12C also includes a fillable bag 1204 having one or more splits or slots 1205 in the bag configured to allow branch tubular graft bodies 1211, 1212, and 1213 to connect to and be in fluid connection with the main tubular graft body 1200. In some arrangements, the distal stent graft segment 1203, the proximal stent graft segment 1201, and the fillable bag 1204 are welded together at a portion 1206.

FIG. 12A shows a side view of the endovascular system, which can be used as a retrograde patch. In various arrangements, the retrograde patch includes the proximal stent graft segment 1201, the distal stent graft segment 1203, and the fillable bag 1204. The fillable bag 1204 may be a polymer fillable bag. In some arrangements, the proximal stent graft segment 1201, the distal stent graft segment 1203, and the fillable bag 1204 are all welded together at the portion 1206. With reference to FIG. 12C, the proximal stent graft segment 1201 is insertable into the ascending aorta portion 13 and in various arrangements decreases in diameter to allow space for retrograde filling chimney style grafts (such as but not limited to, the branch tubular graft bodies 1211, 1212, and 1213). The distal stent graft segment 1203 is insertable into the descending aorta portion 11 or provides a length of stent graft to extend from the descending aorta portion 11. The fillable bag 1204 is used to seal around chimney grafts (such as but not limited to, the branch tubular graft bodies 1211, 1212, and 1213). As shown in FIG. 12A, a portion of a tubular shape of the proximal stent graft segment 1201 appears to be cut out. In some arrangements, the cutout portion corresponds to an area where the fillable bag 1204 is welded. Similarly, a portion of a tubular shape of the distal stent graft segment 1203 appears to be cut out. In some arrangements, the cutout portion corresponds to an area where the fillable bag 1204 is welded. In some arrangements the endovascular system includes a stent 1202 with fixation elements, functioning as anchor elements. The cutout portion is configured to be disposed at and face the greater arch vessels 14, 15, 20. The stent 1202 is attached or fixed to the proximal stent graft segment 1201.

FIG. 12B shows a cross sectional view of the prosthesis at section H-H. FIG. 12C shows a section of the implant (e.g., the endovascular system as described) including the retrograde patch in the aorta 10. With reference to FIGS. 12A and 12C, the distal stent graft segment 1203 is configured to be deployed in the descending aorta portion 11. An end of the distal stent graft segment 1203 is adjacent to or at the left subclavian artery 14. The proximal stent graft segment 1201 is configured to be deployed in the ascending aorta portion 13 and the aortic arch portion 12. The portion 1206 is adjacent to or at the left subclavian artery 14 when the main tubular graft body 1200 is deployed. The branch tubular graft bodies 1211, 1212, and 1213 extends from the portion 1206 to the aortic arch portion 12 to a respective one of the innominate artery 20, the left common carotid artery 15, and the left subclavian artery 14.

The branch tubular graft bodies 1211, 1212, and 1213 each pass through a slot of the one or more slots 1205 in the fillable bag 1204. The branch tubular graft bodies 1211, 1212, and 1213 may form a friction fit with the one or more slots 1205 as the branch tubular graft bodies 1211, 1212, and 1213 are passed through the one or more slots 1205, in some examples. In that regard, the dimensions of the one or more slots 1205 may be smaller than corresponding dimensions of the branch tubular graft bodies 1211, 1212, and 1213, such that the one or more slots 1205 may be stretched as the branch tubular graft bodies 1211, 1212, and 1213 are inserted through the one or more slots 1205. The fillable bag 1204 can then be filled through a fill line 1207 to provide a polymer seal around the branch tubular graft bodies 1211, 1212, and 1213. In some examples, the polymer seal further improves the friction-fit seal. In other examples, the friction fit may not be needed, as the polymer seal is implemented.

Figure 13A:
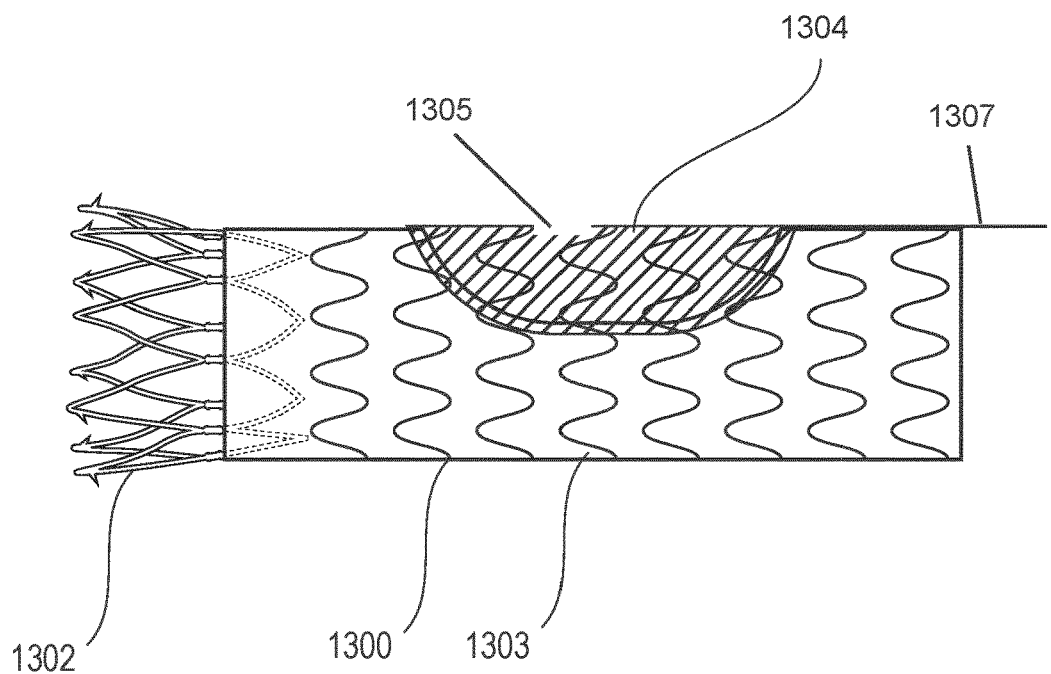
FIG. 13A shows a side view of an endovascular system in accordance with an arrangement.
Figure 13B:
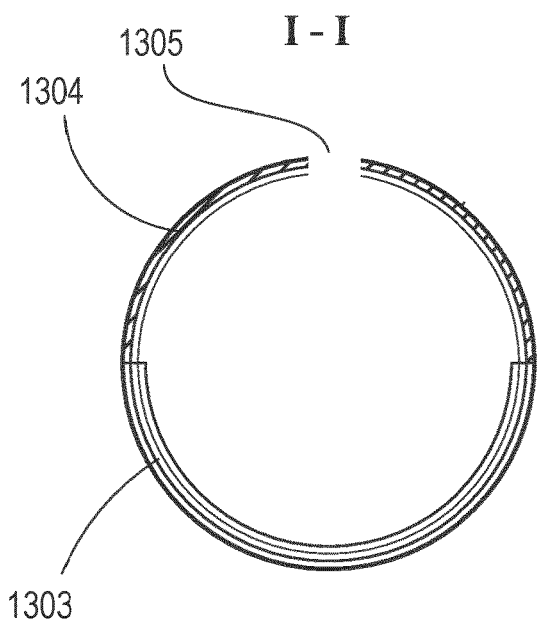
FIG. 13B is a cross-sectional view of the endovascular system of FIG. 13A.
Figure 13C:
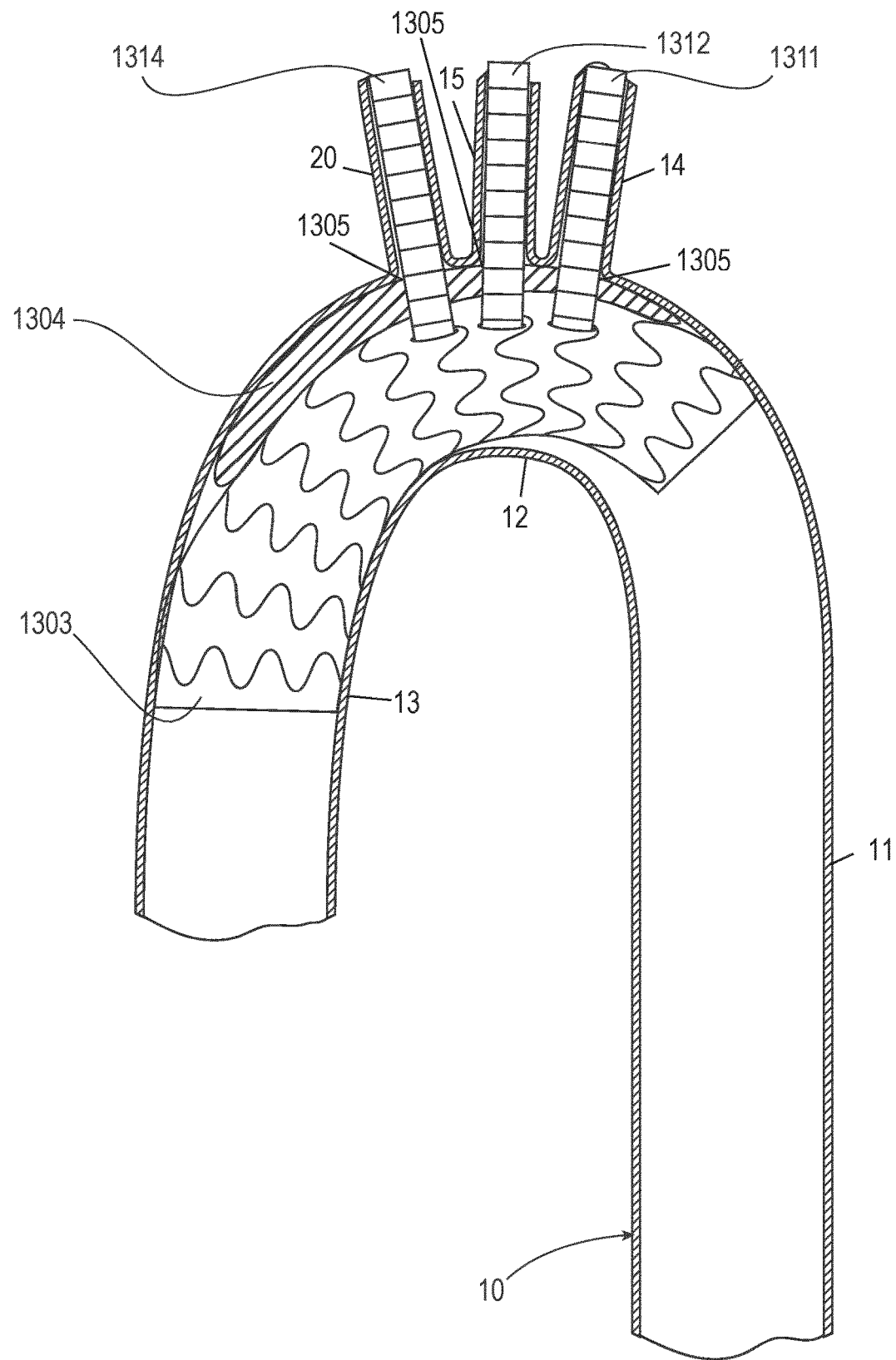
FIG. 13C shows an endovascular system in accordance with an arrangement deployed in an aortic arch.

FIGS. 13A, 13B, and 13C show an endovascular system in accordance with an arrangement. The endovascular system of FIGS. 13A, 13B, and 13C includes a main tubular graft body 1300 having a stent graft segment 1303. The stent graft segment 1303 has suitable stent structures and walls. The stent graft segment 1303 (e.g., a wall thereof) includes at least one fenestration configured to allow for fluid connection between the main tubular graft body 1300 and branch graft bodies 1311, 1312, and 1314. The system also includes a fillable bag 1304 welded to the stent graft segment 1303 and having at least one split or slot 1305 configured to allow access of the branch graft bodies 1311, 1312, and 1314 to the main tubular graft body 1300. The at least one slot 1305 is located at the at least one fenestration (e.g., the location of the at least one split 1305 corresponds to the location of the at least one fenestration). The fillable bag 1304 can then be filled through a fill line 1307 to provide a polymer seal around the branch graft bodies 1311, 1312, and 1314. In some arrangements the endovascular system includes a stent 1302 with fixation elements. When deployed in the aorta, the at least one split 1305 and the at least one fenestration is configured to be disposed at and face the greater arch vessels.

Various arrangements provide for a direct flow patch. FIG. 13A shows a side view of an endovascular system that provides for a direct flow patch. With reference to FIGS. 13A and 13C, in various arrangements, the direct flow patch includes the stent graft segment 1303 and a fillable bag 1304 that are welded together. The branch tubular graft bodies 1311, 1312, and 1314 may form a friction fit with the at least one slot 1305 as the branch tubular graft bodies 1311, 1312, and 1314 are passed through the at least one slot 1305, in some examples. In that regard, the dimensions of the at least one slot 1305 may be smaller than corresponding dimensions of the branch tubular graft bodies 1311, 1312, and 1314, such that the at least one slot 1305 may be stretched as the branch tubular graft bodies 1311, 1312, and 1314 are inserted through the at least one slot 1305. The fillable bag 1304 when filled is configured to expand toward an aorta wall in a portion of the ascending aorta portion 13, the aortic arch portion 12, and a portion of the descending aorta portion 11 that is adjacent to or at the left subclavian artery 14. The fillable bag 1304 when filled is configured to be disposed at and face the greater arch vessels 14, 15, 20.

In some arrangements, the stent graft segment 1303 is insertable into both the ascending aorta portion 13 and the descending aorta portion 11 and provides a length of stent graft to extend from the fillable bag 1304 to seal around chimney grafts (such as but not limited to, the branch graft bodies 1311, 1312, and 1314) that extend directly into the flow lumen of the main tubular graft body 1300. FIG. 13C shows three slots 1305 and three corresponding fenestrations, each slot/fenestration allows a respective one of the branch graft bodies 1311, 1312, and 1314 to extend to a respective one of the left subclavian artery 14, the left common carotid artery 15, and the innominate artery 20.

FIG. 13B shows a cross sectional view of the endovascular system of FIG. 13A. FIG. 13C shows a section of an implant (e.g., the endovascular system as described) including the direct flow patch in the aorta 10. In various arrangements, the direct flow patch includes an integrated filling window where adequate seal is provided around the stent wire frame.

Figure 14A:
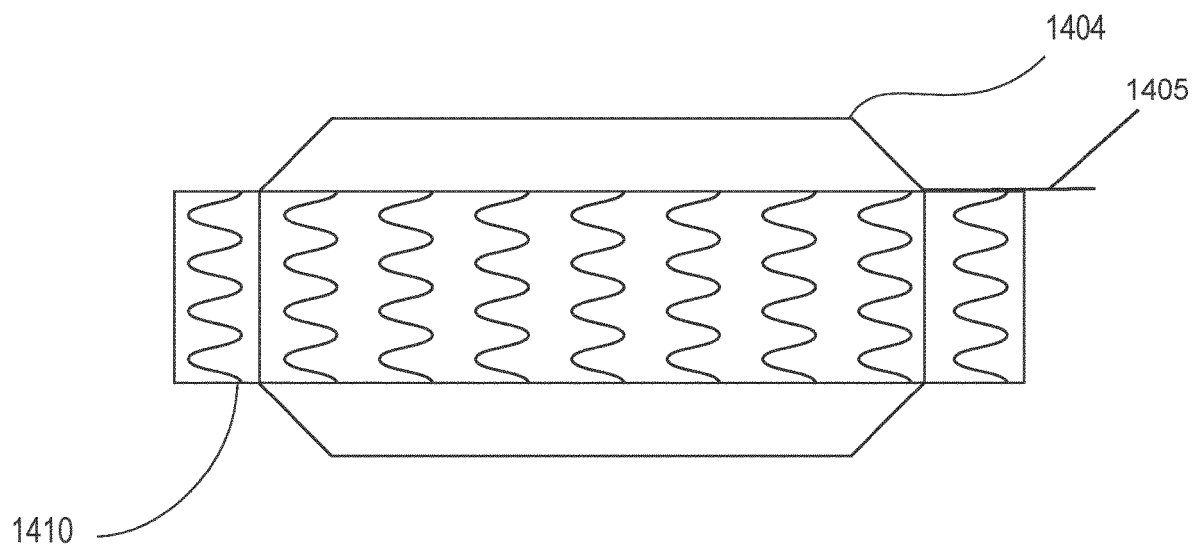
FIG. 14A shows an endovascular system in accordance with an arrangement.
Figure 14B:
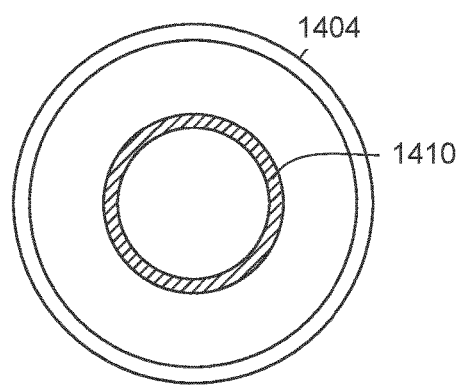
FIG. 14B shows a cross-section view of the endovascular system of FIG. 14A.

FIGS. 14A and 14B show an endovascular system in accordance with an arrangement. The endovascular system of FIGS. 14A and 14B includes a branch stent graft 1410 connected to a fillable bag 1404. In various arrangements, the fillable bag 1404 is connected to a fill line 1405.

Figure 15A:
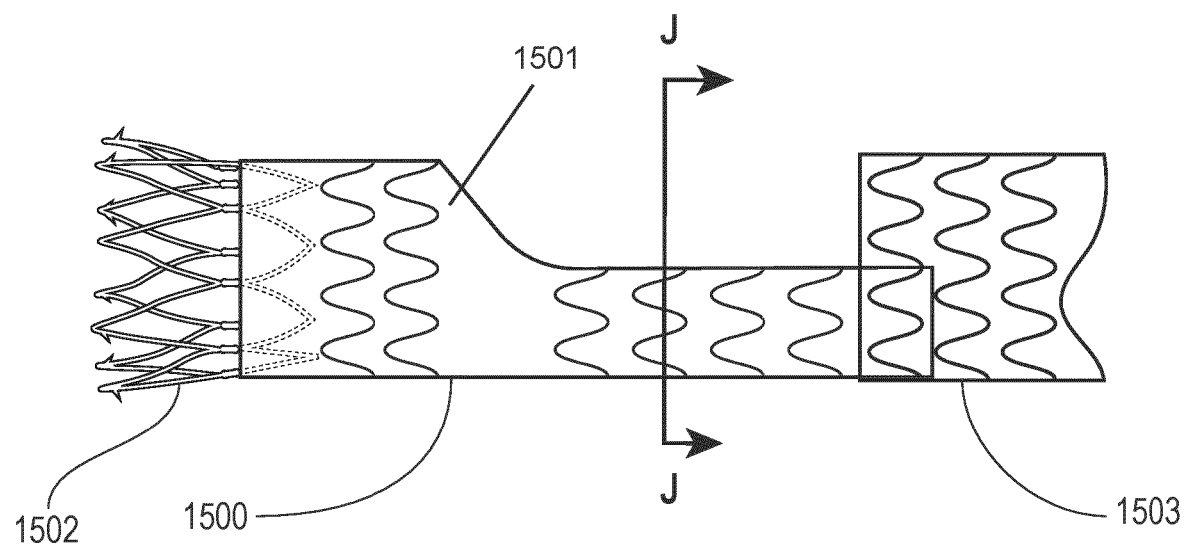
FIG. 15A shows a side view of an endovascular system in accordance with an arrangement.
Figure 15B:
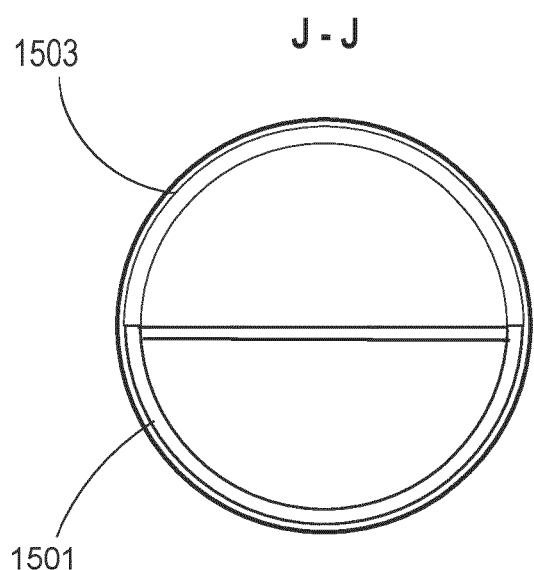
FIG. 15B is a cross-sectional view of a section of FIG. 15A.
Figure 15C:
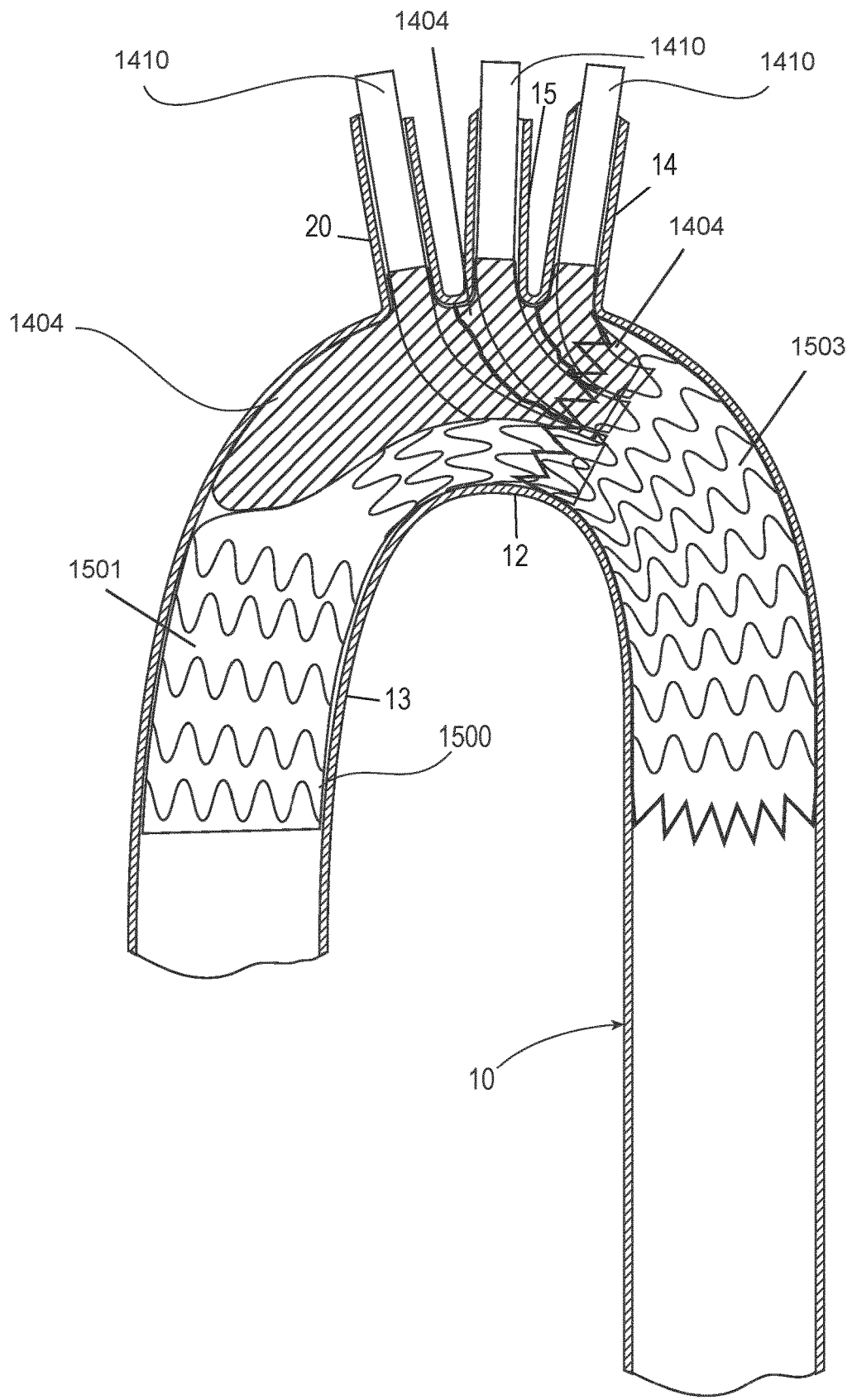
FIG. 15C shows an endovascular system in accordance with an arrangement deployed in an aortic arch.

FIGS. 15A, 15B, and 15C show an endovascular system in accordance with an arrangement. The endovascular system of FIGS. 15A, 15B, and 15C includes a main tubular graft body 1500 which includes a proximal stent graft segment 1501 and a distal stent graft segment 1503 that are placed as modules (not bonded). The proximal stent graft segment 1501 and the distal stent graft segment 1503 have suitable stent structures and walls. The main tubular graft body 1500 also includes one or more anchor members 1502 attached to a proximal end of proximal stent graft segment 1501. The proximal stent graft segment 1501 has a decreasing diameter over at least a portion of a length of segment 1500 (decreasing in a direction toward the distal stent graft segment 1503). The decreasing diameter appears to form a cutout from the proximal stent graft segment 1501, creating a space configured to allow for space for branch graft bodies 1410 to connect to and be in fluid connection with the distal stent graft segment 1503. One or more fillable bags 1404 are configured to fill space around the branch graft bodies 1410.

In various arrangements, each branch graft body 1410 for each branch vessel has a structure as shown in the arrangement of FIG. 14A with the branch stent graft 1410 connected to the fillable bag 1404. FIG. 15C shows three of the systems (e.g., three branch graft bodes 1410, each with the fillable bag 1404) of FIG. 14A used in the three branch vessels 14, 15, and 20, respectively, and connected to be in fluid flow with the distal stent graft segment 1503. Each of the fillable bags 1404 can then be inflated with a fill medium to fill spaces around each of the branch stent grafts 1410. For example, the fillable bags 1404 when filled are configured to fill a space in the aortic arch portion 12 and the ascending aorta portion 13.

Various arrangements provide for modular grafts. Some arrangements provide for retrograde branch grafts with endobags. FIG. 14A shows a side view and FIG. 14B shows an end view of the branch stent graft 1410 with an endobag (the fillable bag 1404). FIG. 15A shows a side view of a main lumen thoracic stent graft as described. In various arrangements, the proximal stent graft segment 1501 of the thoracic graft is used to seal in the ascending aorta portion and decreases in diameter to allow space for retrograde filling chimney style endobag covered grafts, such as the endobag covered graft of FIG. 14A. In various arrangements, the distal stent graft segment 1503 is used to seal in the descending aorta portion or provide a length of stent graft to extend from, and the endobag covered branch grafts are polymer filled to seal the space between the proximal and distal stent graft segments 1501 and 1503 and the branch grafts, such as the branch stent grafts 1410, as shown in FIG. 15C. FIG. 15B shows a cross sectional view of the main lumen prosthesis (including the proximal stent graft segment 1501 and the distal stent graft segment 1503) of FIG. 15A at section J-J. FIG. 15C shows a section of the implant in the aorta 10.

FIGS. 16A, 16B, 16C, and 16D show an endovascular system in accordance with an arrangement. The endovascular system of FIGS. 16A, 16B, 16C, and 16D includes a distal stent graft segment 1603 connected to a fillable bag 1604 and configured to form a distal end of the system when deployed in the aorta 10 of a person. The distal stent graft segment 1603 is configured to be arranged in the descending aorta portion 11. The fillable bag 1604 when filled is configured to expand to contact walls of the descending aorta portion 11.

The endovascular system also includes a proximal stent graft segment 1600 having anchor members 1602 attached to a proximal end of the proximal stent graft segment 1600. The proximal stent graft segment 1600 and the distal stent graft segment 1603 have suitable stent structures and walls. The proximal stent graft segment 1600 is configured to be disposed in the aortic arch portion 12 and the ascending aorta portion 13. The anchor members 1602 are configured to anchor the proximal stent graft segment 1600 in the ascending aorta 13. The proximal stent graft segment 1600 is also connected to a fillable bag 1608. The proximal stent graft segment 1600 has a decreasing diameter over at least a portion of its length (decreasing in a direction toward the distal stent graft segment 1603). The decreasing diameter appears to form a cutout from the proximal stent graft segment 1600, creating a space configured allow for space for branch grafts, such as but not limited to, branch grafts 1611, 1612, and 1613 to connect with and be in fluid connection with the distal stent graft segment 1603 when an end of the proximal stent graft segment 1600 is within the distal stent graft segment 1603. The fillable bag 1604 is fillable through a fill tube 1607 to seal a space around the distal stent graft segment 1603. The fillable bag 1608 is fillable through a fill tube 1609 to seal a space around the proximal stent graft segment 1600.

Figures 16A, 16B:
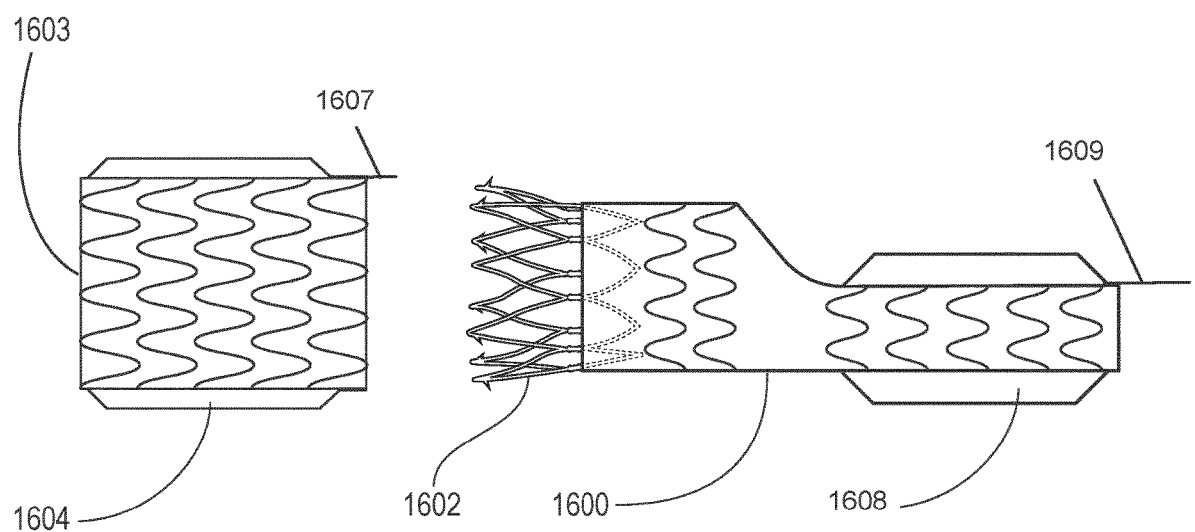
FIG. 16A shows a side view of a distal graft segment of an endovascular system in accordance with an arrangement.
FIG. 16B shows a side view of a proximal graft segment of an endovascular system in accordance with an arrangement.
Figure 16C:
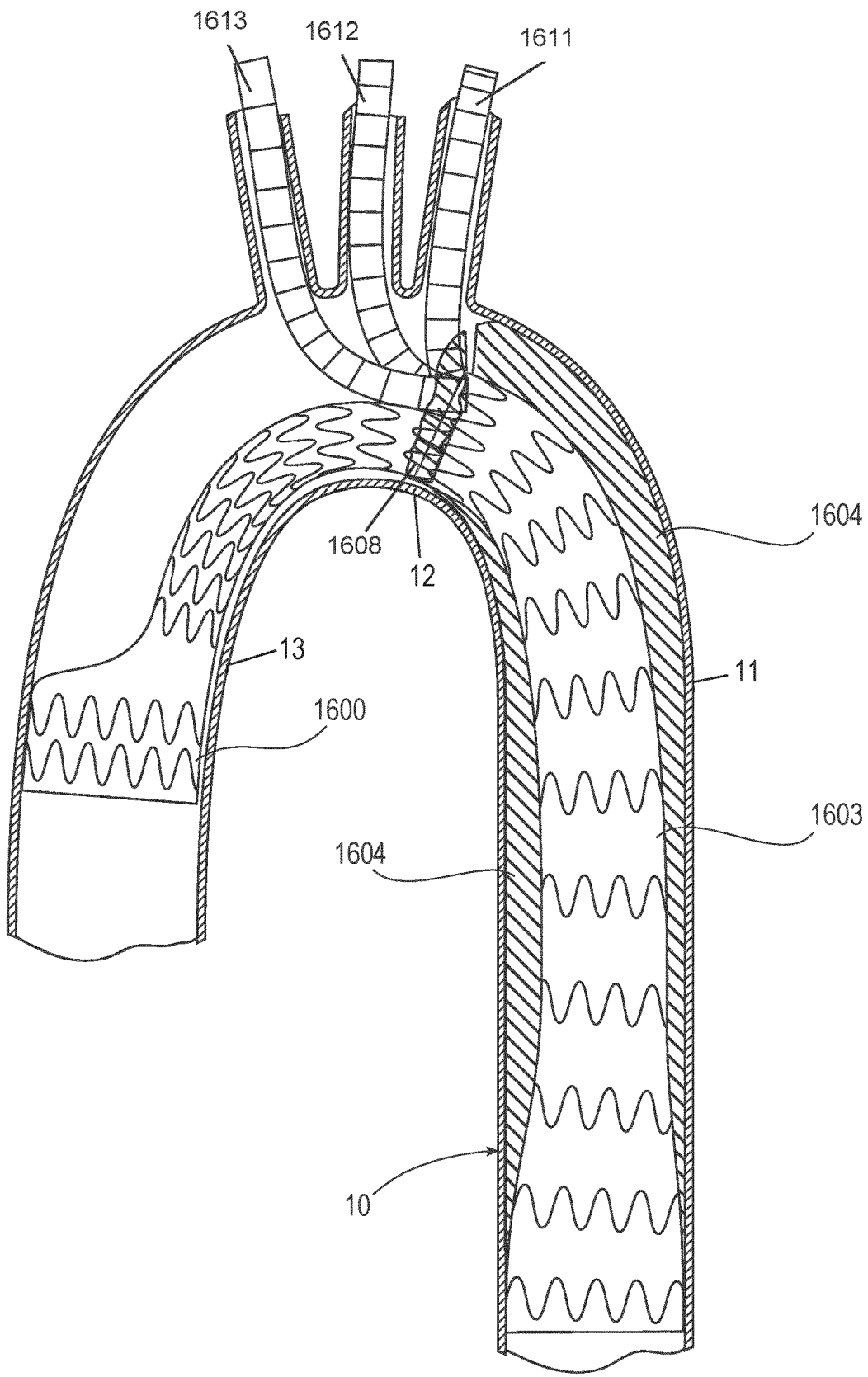
FIG. 16C shows an endovascular system including a distal graft segment and a proximal graft segment in accordance with an arrangement.
Figure 16D:
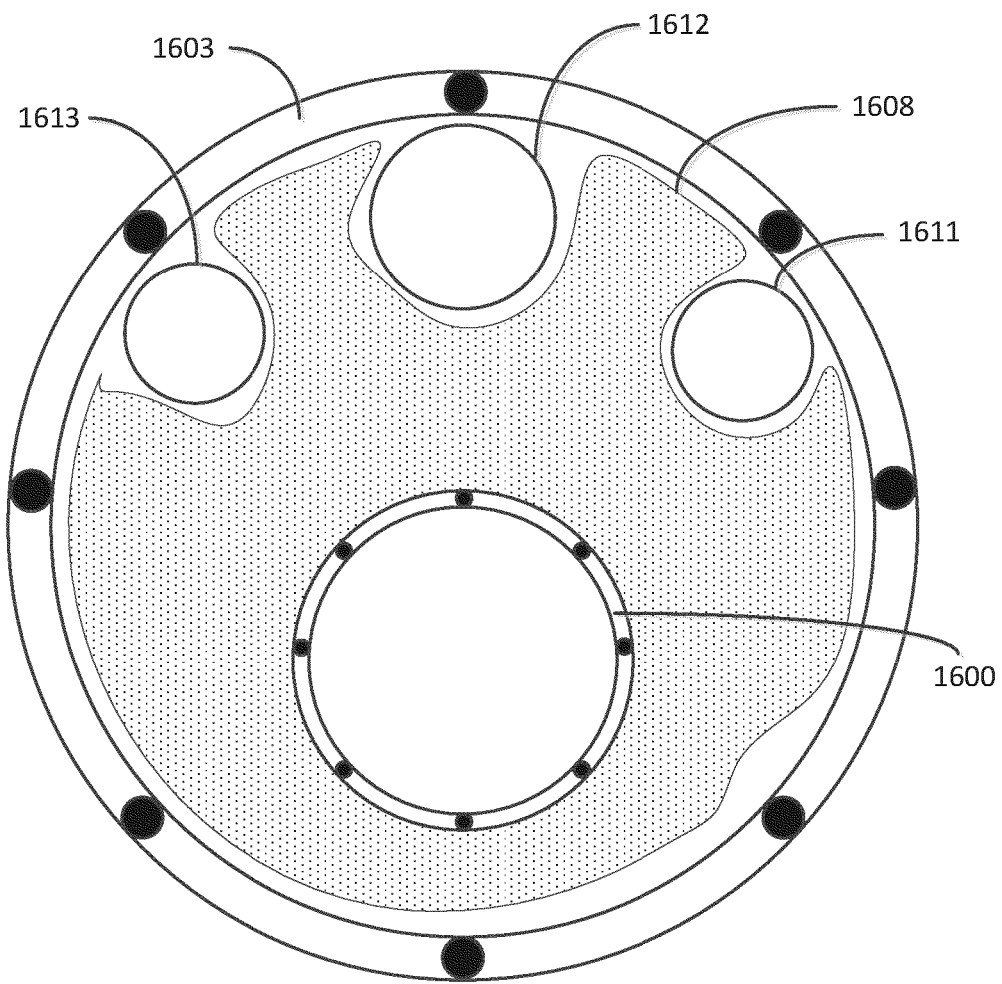
FIG. 16D shows a view of the endovascular system of FIG. 16C.

Various arrangements provide for retrograde branch grafts with fully modular endobag covered arch and descending grafts. FIG. 16A shows a side view of the distal stent graft segment 1603 with an endobag (e.g., the fillable bag 1604). FIG. 16B shows a side view of the proximal stent graft segment 1600 with an endobag (e.g., the fillable bag 1608). With reference to FIG. 16C, in various arrangements, the distal stent graft segment 1603 is placed first, achieving seal in the distal aorta (the descending aorta portion 11) just distal of the left subclavian artery 14. In various arrangements, the proximal stent graft segment 1600 of the thoracic graft is placed in the ascending aorta portion 13 and docks with the distal stent graft segment 1603, as the proximal stent graft segment 1600 and the distal stent graft segment 1603 are modular. In some arrangements, the proximal stent graft segment 1600 also decreases in diameter to allow space for retrograde filling chimney style covered grafts 1611, 1612, and 1613 and has an integrated endobag over its most distal aspect to seal around the chimney grafts and the distal stent graft segment 1603. FIG. 16C shows a section of the implant in the aorta 10. FIG. 16D shows that the fillable bag 1608 around the proximal stent graft segment 1600 is fillable to fill a space within an end of the distal stent graft segment 1603 and around the branch grafts 1611, 1612, and 1613.

Various arrangements provide a user with the ability to access the brachiocephalic, left carotid, and left subclavian arteries (great vessels) in the aortic arch from a femoral approach and the ability to perfuse them. Some arrangements are deployed in a bottom up approach, starting with the descending aorta first followed by an ascending and arch graft and great vessel stent grafts. Some arrangements provide a modular system with access for cannulation of great vessels with endobag designs. Some arrangements utilize a modular endobag covered graft to perform a procedure with the branch grafts facing the ascending aorta in an antigrade direction, and utilizing the endobag to seal around the branch grafts and aorta.

Figure 17A:
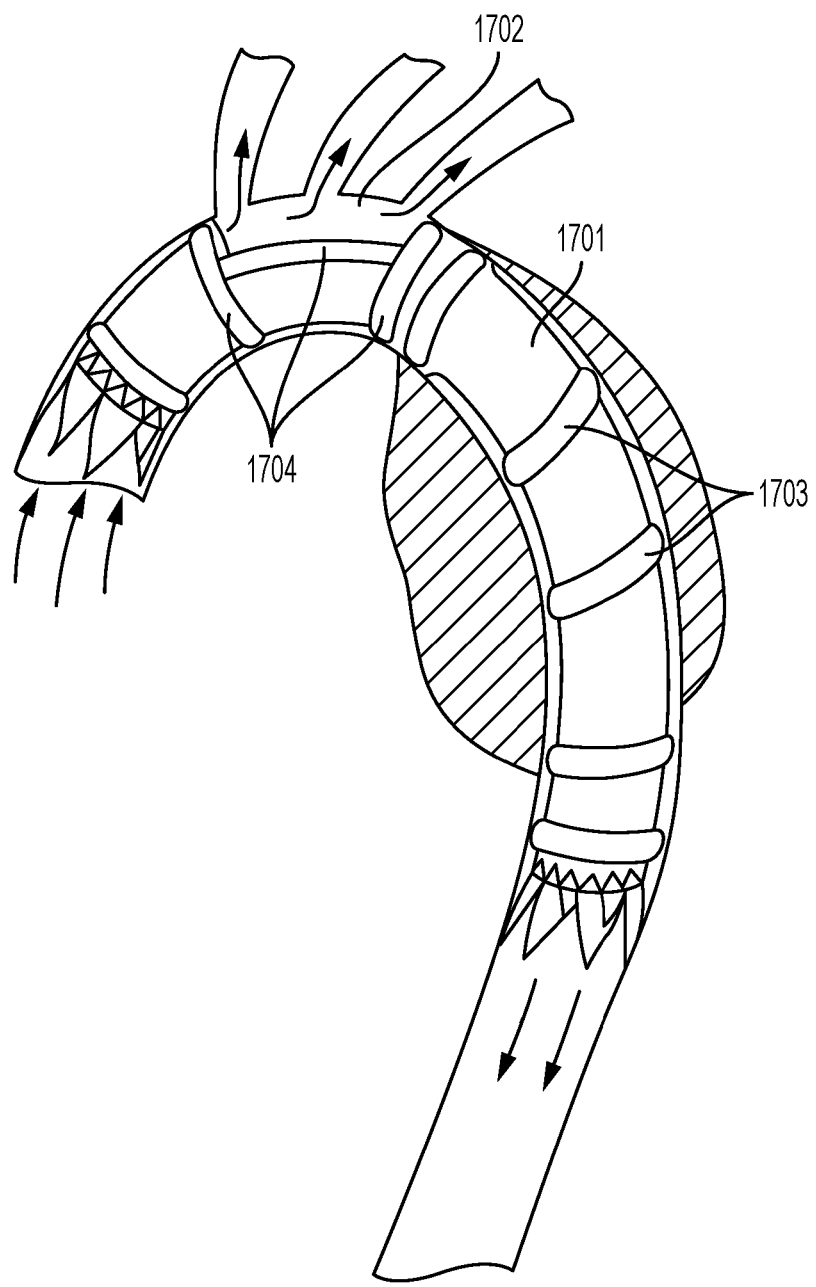
FIG. 17A shows an endovascular system in accordance with an arrangement.
Figure 17B:
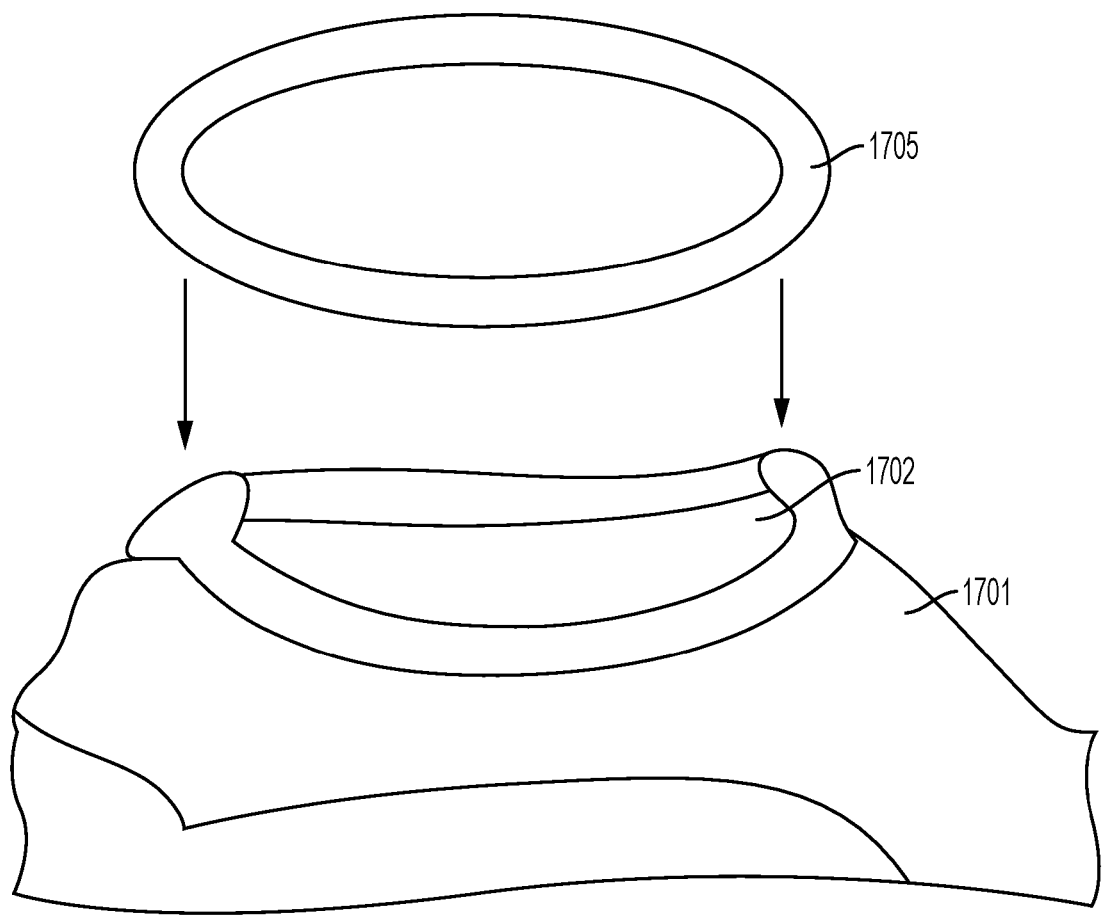
FIG. 17B shows a portion of an endovascular system in accordance with an arrangement.

FIG. 17A illustrates an arrangement of an endovascular system that has a large fenestration 1702 in a stent graft 1701 with polymer sealing rings 1703. The fenestration 1702 may be bounded by polymer channels 1704 for axial support as well as radial support. In some arrangements, the top fenestration 1702 includes an elliptically shaped arch fenestration as illustrated in FIG. 17B. In various arrangements, the large fenestration 1702 is sized to be inclusive to the arch vessels and has radiopaque markers made from suitable materials (i.e. platinum, gold, etc.) indicating the location of the fenestration position both axially and rotationally with respect to the aortic arch vessels. The large fenestration 1702 allows for blood flow to the supra-arch vessels. As shown in FIG. 17B, in various arrangement separate channels or tubes 1705 are welded onto a graft of the stent graft 1701.

Figure 18A:
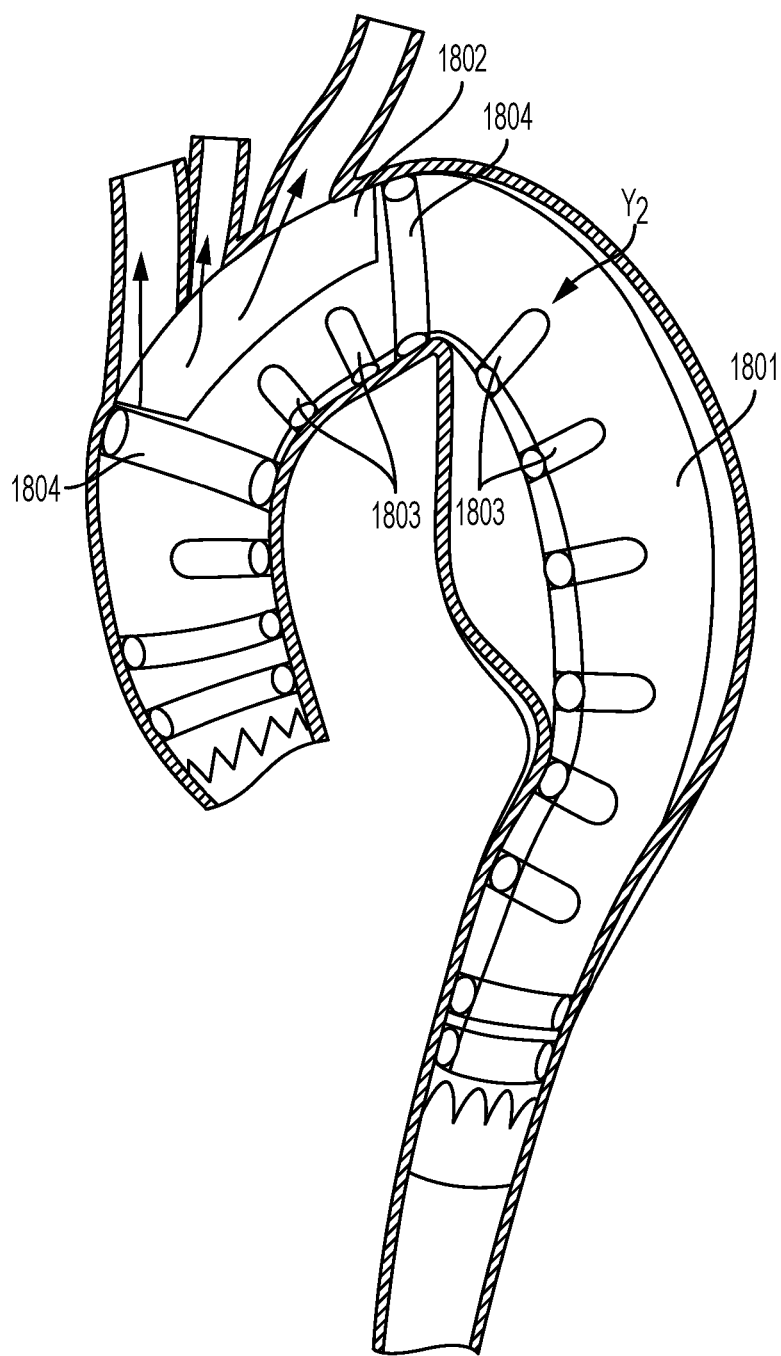
FIG. 18A shows an endovascular system in accordance with an arrangement.
Figure 18B:
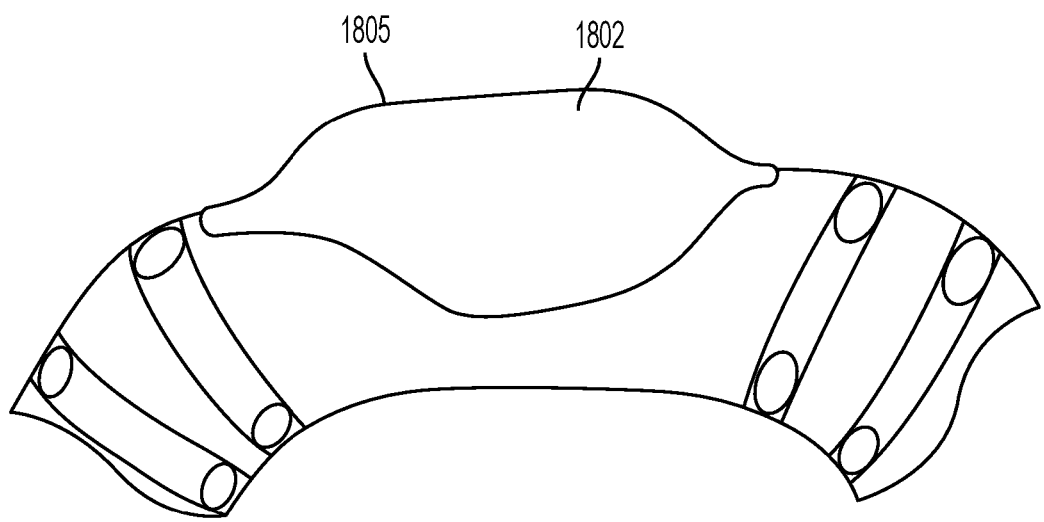
FIG. 18B shows a portion of an endovascular system in accordance with an arrangement.

FIG. 18A illustrates an arrangement of an endovascular system that has a large fenestration 1802 in a stent graft 1801 with polymer sealing rings 1803 and 1804. The polymer sealing rings 1803 are half-rings and the polymer sealing rings 1804 are full rings. In various arrangements, the fenestration 1802 has polymer ½ ring channels 1803 for radial support and flexibility in the fenestrated region and along a length of the stent graft 1801. The open fenestration 1802 allows for perfusion to branch vessels in the arch region. In some arrangements, the stent graft 1801 is modular with a distal wire wound component. In some arrangements, half rings 1803 under the fenestration 1802 provide support while full sealing rings 1804 on the proximal and distal sides of the fenestration 1802 provide sealing. In various arrangements, a pre-fill is performed to allow for visualizing ring orientation and sealing. In some arrangements, the top fenestration 1802 includes a shaped arch fenestration/aperture fabricated from nitinol wire 1805 or laser cut as illustrated in FIG. 18B.

Figure 19A:
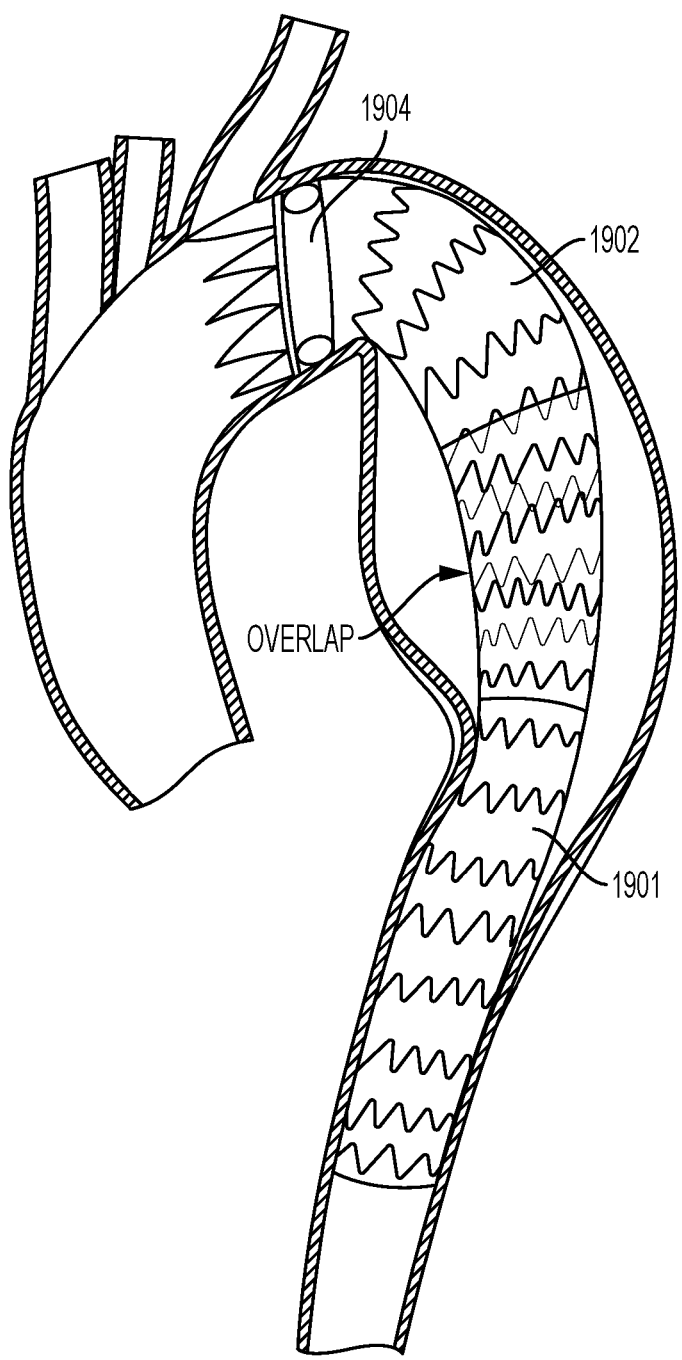
FIG. 19A shows an endovascular system in accordance with an arrangement.
Figure 19B:
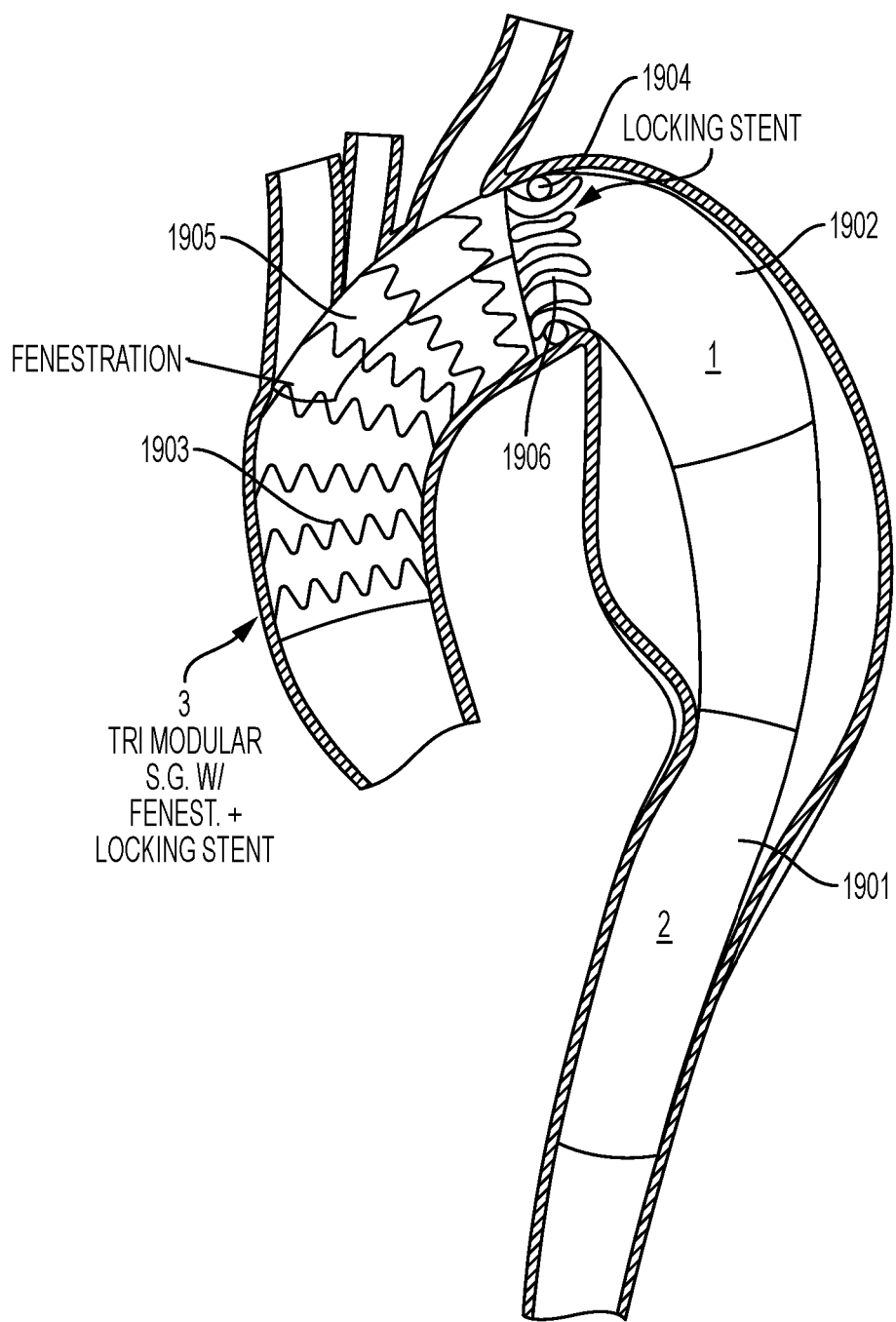
FIG. 19B shows an endovascular system in accordance with an arrangement.

FIGS. 19A and 19B illustrate a trimodular device in accordance with an arrangement. The trimodular device includes a distal modular component 1901 and a proximal component 1902 with sealing ring 1904. In some embodiments, the device further includes an arch component 1903 with a fenestration 1905 and a distal locking stent 1906. In various arrangements, each of the distal modular component 1901, the proximal component 1902, and the arch component 1903 comprises a stent graft. In various arrangements the proximal component 1902 is deployed with the sealing ring 1904 and the distal modular component 1901 is deployed to partially overlap an end of the proximal component 1902. In various arrangements, the arch component 1903 with the fenestration 1905 and distal locking stent 1906 is deployed with the distal locking stent 1906 flared at crown tips to conform to the sealing ring 1904. In some arrangements, the locking stent 1906 is deployed after positioning the arch component 1903. In various arrangements, the arch component 1903 is produced with the fenestration 1905 suitable for perfusing the arch vessels and is configured to dock into the descending thoracic stent graft components, such as the proximal component 1902. An advantage of this approach would be to treat patients if the disease date progressed into the arch or ascending aorta after having been previously treated with a descending thoracic device. In some arrangements, the trimodular device is built from the bottom up.

Figure 20A:
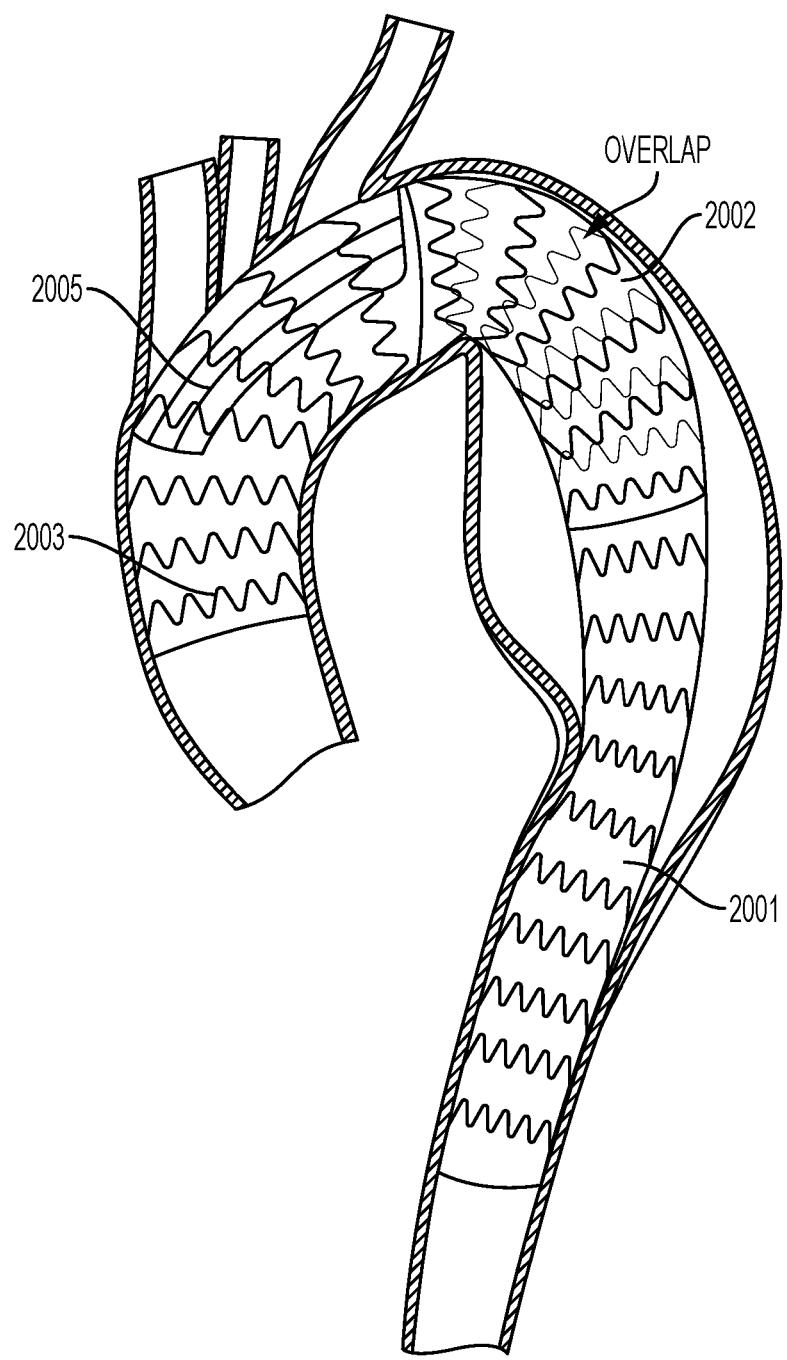
FIG. 20A shows an endovascular system in accordance with an arrangement.
Figure 20B:
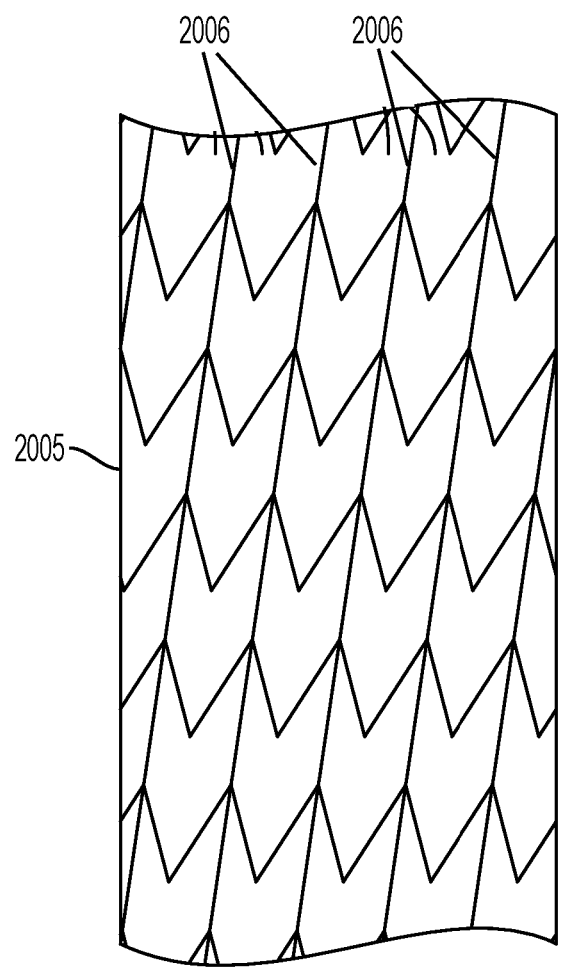
FIG. 20B shows a portion of a system in accordance with an arrangement.
Figure 20C:
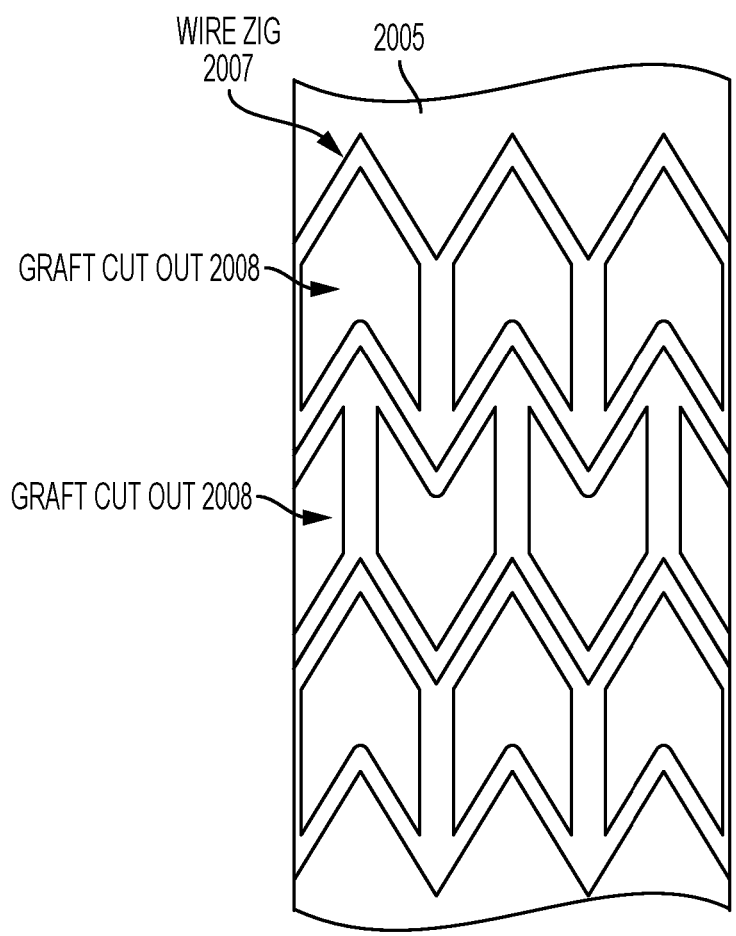
FIG. 20C shows a portion of a system in accordance with an arrangement.

FIGS. 20A, 20B, and 20C show arrangements of systems with respect to fenestration alternatives where PTFE thread, nitinol wire, or cutouts of previously laminated graft material are used to stabilize the stent structure. FIG. 20A shows a trimodular device that includes a distal modular component 2001, a proximal component 2002, and an arch component 2003 with an open wire fenestration 2005. In various arrangements, each of the distal modular component 2001, the proximal component 2002, and the arch component 2003 comprises a stent graft. As shown in FIG. 20B, in various arrangements the open wire fenestration 2005 includes a stabilizing structure of PTFE thread loops 2006. As shown in FIG. 20C, in various arrangements the open wire fenestration 2005 is cut out of graft to expose a portion of the wire but some of the graft material is allowed to remain for stabilizing the wire. In various arrangements, the open wire fenestration 2005 includes the wire zigs 2007 with graft cut outs 2008.

Figure 21A:
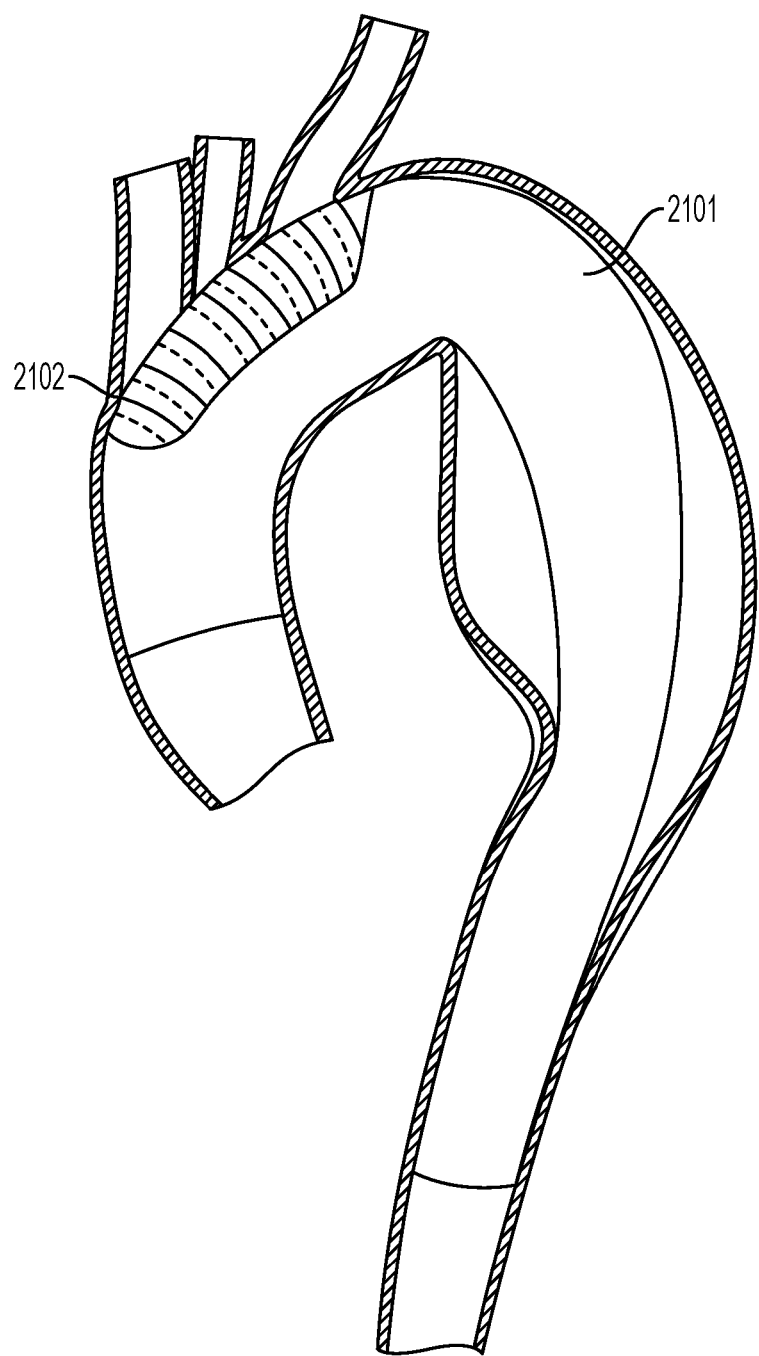
FIG. 21A shows an endovascular system in accordance with an arrangement.
Figure 21B:
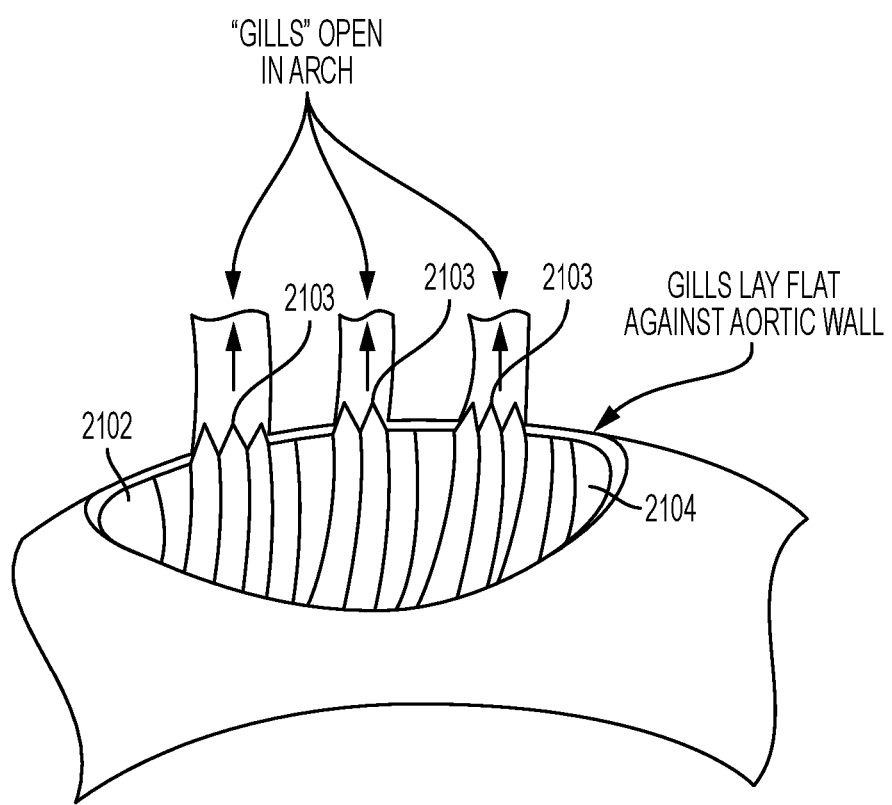
FIG. 21B shows a portion of a system in accordance with an arrangement.

FIG. 21A shows a system in accordance with an arrangement. The system includes a stent graft 2101 with a top arch section 2102. In various arrangements, the top arch section 2102 includes overlapping graft strips that act like gills to enable profusion to arch vessels where they are not in apposition to the aortic wall. FIG. 21B shows the top arch section 2102 of FIG. 21A in accordance with an arrangement with gills 2103 that are open in the arch to perfuse branch vessels and gills 2104 that lay flat against the aortic wall to remain closed.

Figure 22A:
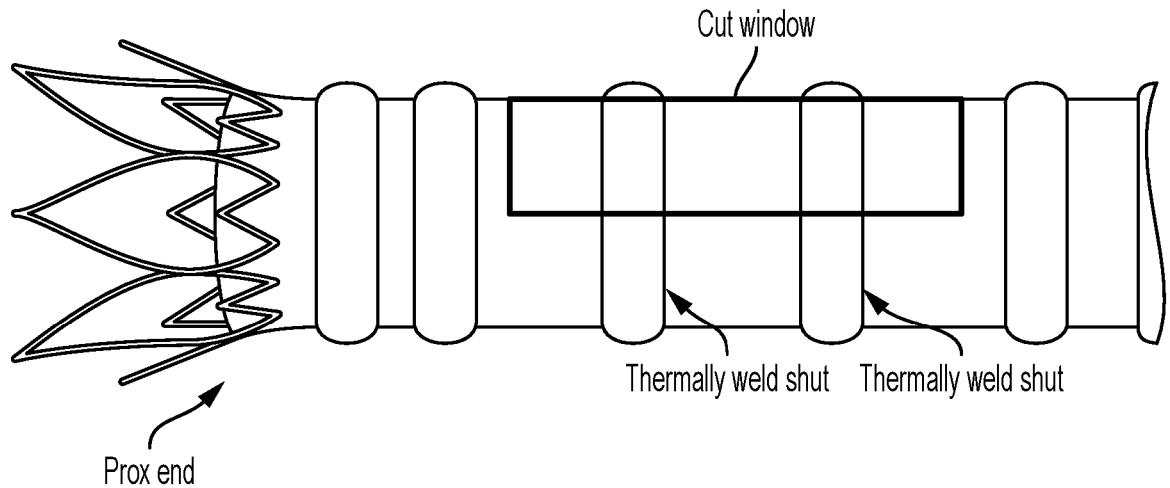
FIG. 22A shows a device with a cut window to be cut out in accordance with an arrangement.
Figure 22B:
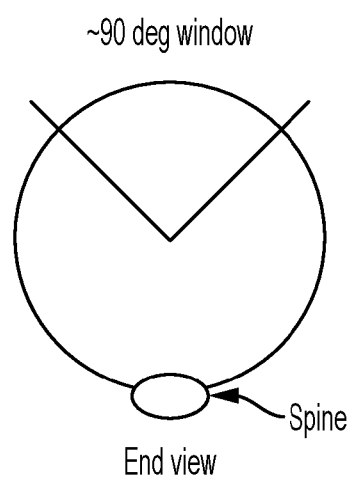
FIG. 22B shows a diagram for the cut window in accordance with an arrangement.
Figure 22C:
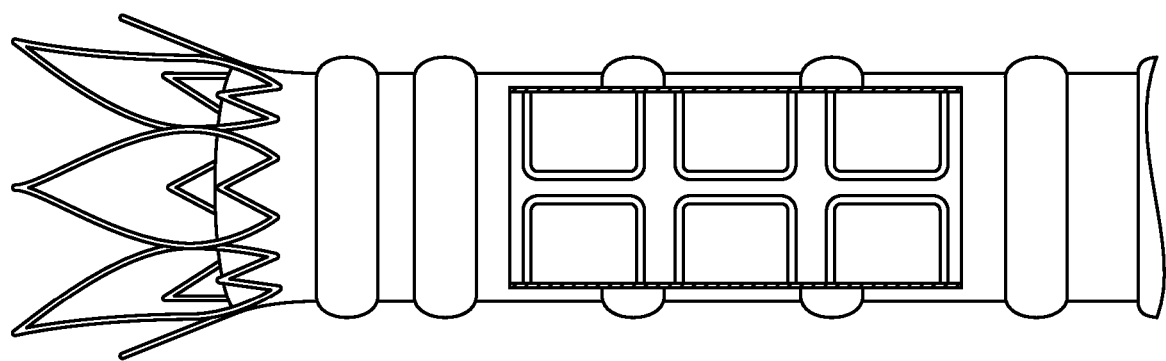
FIG. 22C shows a device in accordance with an arrangement.
Figure 22D:
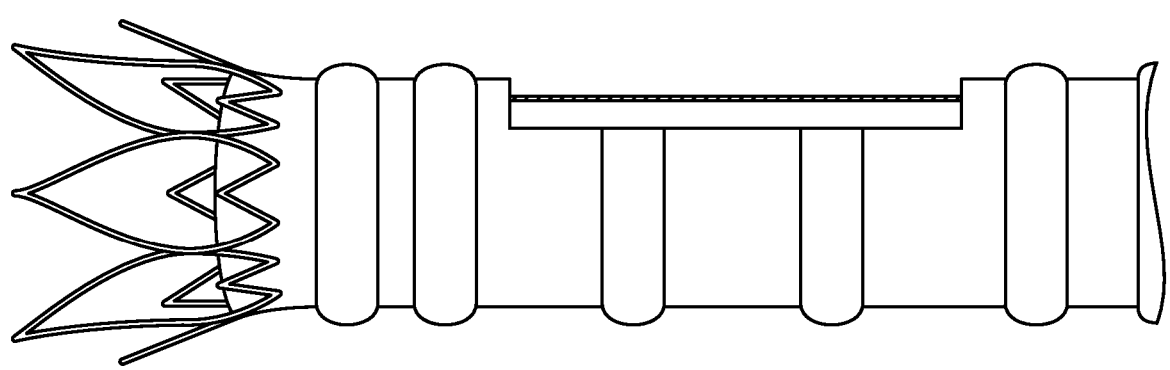
FIG. 22D shows a device in accordance with an arrangement.

FIG. 22A shows a stent graft system in accordance with an arrangement with a cut window to be cut for a large fenestration for arch vessels. FIG. 22B shows an example in which the cut window is 90 degrees. FIGS. 22C and 22D show views of the stent graft system of FIG. 22A after the cut window has been cut as indicated by the diagram of FIG. 22B.

Various embodiments include methods for using or deploying an endovascular system according to the various arrangements disclosed above. Such methods include a method for inserting an endovascular system into a main artery of a person that includes the steps of positioning a balloon in an aorta to create space, positioning an endovascular system into an ascending portion of the main artery, injecting a polymer to seal the main artery and create a channel for a branch artery, curing the polymer, deflating the balloon, and removing the balloon from the main artery. In one aspect of the method, the balloon is a compliant balloon. In one aspect of the method, the balloon is a non-compliant balloon. In one aspect, the method includes the step of re-sheathing before the step of removing the balloon from the aorta. In one aspect, the method includes the step of actively fixating the endovascular system.

According to a further method, a method for inserting an endovascular system in a main artery of a person includes the steps of deploying an endovascular system into a main artery, gaining wire access of at least one branch artery, deploying chimney grafts into each of the at least one branch artery, and positioning an endovascular system such that there is an axial overlap between the endovascular system and the branch grafts. In one aspect of the method, the step of gaining wire access of at least one branch artery is performed using at least two wires. In one aspect of the method, the step of gaining wire access of at least one branch artery is performed using three wires. In one aspect of the method, the branch stent grafts comprise bare stents.

While various arrangements of the present disclosure are specifically illustrated and/or described herein, it will be appreciated that modifications and variations of the present disclosure may be effected by those skilled in the art without departing from the spirit and intended scope of the disclosure. Further, any of the arrangements or aspects of the disclosure as described in the claims or in the specification may be used with one and another without limitation.

What is claimed is:

1. An endovascular system, comprising:
    a main tubular graft body configured to be deployable within a main artery, wherein the main tubular graft body comprises a tubular graft wall;
    a plurality of inflatable channels disposed along the main tubular graft body; and
    a plurality of stent rings disposed along the tubular graft wall of the main tubular graft body,
    wherein the plurality of inflatable channels are configured to be inflated with an inflation medium, and
    a first graft wall portion disposed between a first inflatable channel and a second inflatable channel, said first and said second inflatable channels being adjacent to each other;
    wherein more than one of the plurality of stent rings are disposed on a surface of the first graft wall portion.

2. The endovascular system according to claim 1, further comprising a second graft wall portion disposed between a third inflatable channel and a fourth inflatable channel, said third and said fourth inflatable channels being adjacent to each other, and the more than one of the plurality of stent rings is disposed on a surface of the second graft wall portion.

3. The endovascular system according to claim 2, wherein the main tubular graft body has at least one fenestration disposed on the second graft wall portion.

4. The endovascular system according to claim 1, wherein the plurality of stent rings comprises a continuous wire wound stent.

5. The endovascular system according to claim 1, wherein the main tubular graft body has at least one fenestration disposed on the first graft wall portion and configured to be in fluid contact with at least one branch artery branched from the main artery.

6. The endovascular system according to claim 5, wherein the fenestration is covered by a stent mesh.

7. The endovascular system according to claim 5, wherein the fenestration is bounded by the two or more adjacent inflatable channels and the more than one of the plurality of stent rings.

8. An endovascular system, comprising:
    a main tubular graft body configured to be deployable within a main artery, wherein the main tubular graft body comprises a tubular graft wall;
    an inflatable channel helically disposed along the main tubular graft body, wherein the inflatable channel is configured to be inflated with an inflation medium;
    a plurality of stent rings disposed along the tubular graft wall of the main tubular graft body; and
    a first graft wall portion disposed between a first portion of the inflatable channel and a second portion of the inflatable channel along an axial length of the main tubular graft body,
    wherein more than one of the plurality of stent rings are disposed on a surface of the first graft wall portion.

* * * * *